US012281332B2

(12) United States Patent
Homan et al.

(10) Patent No.: US 12,281,332 B2
(45) Date of Patent: Apr. 22, 2025

(54) METHODS OF ENHANCING DEVELOPMENT OF RENAL ORGANOIDS AND METHODS OF USING THE SAME

(71) Applicants: President and Fellows of Harvard College, Cambridge, MA (US); The Brigham And Women's Hospital, Inc., Boston, MA (US)

(72) Inventors: Kimberly A. Homan, Somerville, MA (US); Navin R. Gupta, Brighton, MA (US); Katharina T. Kroll, Boston, MA (US); David B. Kolesky, Cambridge, MA (US); Mark Skylar-Scott, Brookline, MA (US); Michael T. Valerius, Belmont, MA (US); Joseph Bonventre, Wayland, MA (US); Ryuji Morizane, Brookline, MA (US); Jennifer Lewis, Cambridge, MA (US)

(73) Assignees: PRESIDENT AND FELLOWS OF HARVARD COLLEGE, Cambridge, MA (US); THE BRIGHAM AND WOMEN'S HOSPITAL, INC., Boston, MA (US)

(*) Notice: Subject to any disclaimer, the term of this patent is extended or adjusted under 35 U.S.C. 154(b) by 527 days.

(21) Appl. No.: 16/620,225

(22) PCT Filed: Jun. 8, 2018

(86) PCT No.: PCT/US2018/036677
§ 371 (c)(1),
(2) Date: Dec. 6, 2019

(87) PCT Pub. No.: WO2018/227101
PCT Pub. Date: Dec. 13, 2018

(65) Prior Publication Data
US 2020/0248147 A1  Aug. 6, 2020

Related U.S. Application Data

(60) Provisional application No. 62/517,536, filed on Jun. 9, 2017.

(51) Int. Cl.
*C12N 5/071* (2010.01)
*A61K 35/22* (2015.01)
*G01N 33/50* (2006.01)

(52) U.S. Cl.
CPC ............ *C12N 5/0686* (2013.01); *A61K 35/22* (2013.01); *G01N 33/5082* (2013.01); *C12N 2500/00* (2013.01); *C12N 2501/119* (2013.01); *C12N 2503/04* (2013.01); *C12N 2506/02* (2013.01); *C12N 2506/45* (2013.01); *C12N 2513/00* (2013.01); *C12N 2521/00* (2013.01); *C12N 2533/52* (2013.01); *C12N 2533/54* (2013.01); *C12N 2533/56* (2013.01); *C12N 2533/90* (2013.01); *G01N 2500/10* (2013.01)

(58) Field of Classification Search
CPC ............. C12N 5/0686; C12N 2500/00; C12N 2501/119; C12N 2503/04; C12N 2506/02; C12N 2506/45; C12N 2513/00; C12N 2521/00; C12N 2533/52; C12N 2533/54; C12N 2533/56; C12N 2533/90; A61K 35/22; G01N 33/5082; G01N 2500/10
See application file for complete search history.

(56) References Cited

U.S. PATENT DOCUMENTS

| 6,150,164 A | 11/2000 | Humes |
| 10,117,968 B2 | 11/2018 | Lewis et al. |
| 2006/0286078 A1 | 12/2006 | Humes |
| 2013/0236879 A1* | 9/2013 | Berry ................. G01N 33/5064 435/395 |
| 2014/0074007 A1 | 3/2014 | McNeil |
| 2015/0076066 A1 | 3/2015 | Zink et al. |
| 2015/0253309 A1* | 9/2015 | Marx ..................... C12M 23/16 435/284.1 |
| 2018/0030409 A1 | 2/2018 | Lewis et al. |
| 2018/0110901 A1 | 4/2018 | Lewis et al. |
| 2019/0022283 A1 | 1/2019 | Lewis et al. |
| 2019/0224370 A1 | 7/2019 | Kolesky et al. |

FOREIGN PATENT DOCUMENTS

| CN | 104490489 A | 4/2015 |
| CN | 106163581 A | 11/2016 |
| WO | WO 2015/057261 A1 | 4/2015 |
| WO | WO 2015/069619 A1 | 5/2015 |
| WO | WO 2016/094948 A1 | 6/2016 |
| WO | WO 2016/141137 A1 | 9/2016 |
| WO | WO 2016/179242 A1 | 11/2016 |
| WO | WO 2017/041041 A1 | 3/2017 |

(Continued)

OTHER PUBLICATIONS

Carroll et al ("Wnt9b Plays a Central Role in the Regulation of Mesenchymal to Epithelial Transitions Underlying Organogenesis of the Mammalian Urogenital System," Developmental Cell, vol. 9, 283-292, Aug. 2005) (Year: 2005).*
Lacueva-Aparicio et al ("Role of extracellular matrix components and structure in new renal models in vitro," Front. Physiol., Dec. 7, 2022 Sec. Renal Physiology and Pathophysiology vol. 13—2022) (Year: 2022).*
Takasato, M. and Little, M., "A strategy for generating kidney organoids: recapitulating the development in human pluripotent stem cells," Dev Biol., 420(2):210-220 (2016).
Takasato, M. et al., "Kidney organoids from human iPS cells contain multiple lineages and model human neehrogenesis," Nature, 526:564-568 (2015).
Wu, H., et al., "Comparative analysis of kidney organoid and adult human kidney single cell and single nucleus transcriptomes," bioRxiv, doi:10.1101/232561 (2017).

(Continued)

Primary Examiner — Emily A Cordas
(74) Attorney, Agent, or Firm — Crowell & Moring LLP

(57) ABSTRACT

Described are methods of enhancing development of renal organoids, methods of using the same, and kits.

15 Claims, 32 Drawing Sheets
(21 of 32 Drawing Sheet(s) Filed in Color)
Specification includes a Sequence Listing.

(56) References Cited

FOREIGN PATENT DOCUMENTS

| WO | WO 2017/049243 A1 | 3/2017 |
| WO | WO 2018/048900 A1 | 3/2018 |

OTHER PUBLICATIONS

Camp, J., et al., "Multilineage communication regulates human liver bud development from pluripotency," *Nature*, 000:1-22 (2017).
Morizane, et al. "Generation of nephron progenitor cells and kidney organoids from human pluripotent stem cells," *Nat Protoc.*, 12(1):195-207 (Jan. 2017).
Morizane, R. et al., "Nephron organoids derived from human pluripotent stem cells model kidney development and injury," *Nat Biotechnol.*, 33(11):1193-1200 (Nov. 2015).
Zudaire, E., "A Computational Tool for Quantitative Analysis of Vascular Networks," *PLOS ONE*, 6(11):e27385, pp. 1-12 (Nov. 2011).
Munro, D. et al., "Cycles of vascular plexus formation within the nephrogenic zone of the developing mouse kidney," *Scientific Reports*, 7:3273, pp. 1-13 (Jun. 12, 2017).
Daniel, E. et al., "Spatiotemporal heterogeneity and patterning of developing renal blood vessels," *Angiogenesis*, 21:617-634 (2018).
Robert, B., et al., "Direct visualization of renal vascular morphogenesis in Flk1 heterozygous mutant mice," *Am. J. of Physiol.*, 275(*Renal Physiol*. 44):F164-F172 (1998).
McMahon, A., "Development of the Mammalian Kidney," *Curr Top Dev Biol.*, 117:31-54 (2016).
Abrahamson, D., "Development of kidney glomerular endothelial cells and their role in basement membrane assembly," *Organogenesis*, 5(1):275-287 (2009).
Scheppke, L., et al., "Notch promotes vascular maturation by inducing integrin-mediated smooth muscle cell adhesion to the endothelial basement membrane," *Blood*, 119(9):2149-2158 (Mar. 1, 2012).
Van den Berg, C., et al., "Renal Subcapsular Transplantation of PSC-Derived Kidney Organoids Induces Neo-vasculogenesis and Significant Glomerular and Tubular Maturation In Vivo," *Stem Cell Reports*, 10:751-765 (Mar. 13, 2018).
Notification of Transmittal of the International Search Report and The Written Opinion of the International Searching Authority and the International Search Report and Written Opinion dated Aug. 6, 2018 received in PCT Application No. PCT/US18/36677.
Notification Concerning Transmittal Of International Preliminary Report On Patentability and the International Preliminary Report On Patentability for PCT/US18/36677 issued Dec. 10, 2019.
Jang, K-J., et al., "Human Kidney Proximal tubule-on-a-Chip for Drug Transport and Nephrotoxicity Assessment," *Integrative Biology*, 5(9):1089-1198 (Sep. 2013).
Vasilyev, A., et al., "Collective Cell Migration Drives Morphogenesis of the Kidney Nephron," *PLOS Biology*, 7(1): 0101-0114 (Jan. 2009).
First Office Action received in Chinese Patent Application No. 201780068154.6 dated Feb. 26, 2021 (in Chinese and including English translation of the First Office Action), including the Search Report.
First Office Action received in Chinese Patent Application No. 201880038158.4 dated Aug. 2, 2021 (in Chinese and including English translation).
Second Office Action received in corresponding Chinese Patent Application No. 201880038158.4 dated Feb. 25, 2022 (in Chinese and including English translation of the Second Office Action).
Extended European Search Report dated Feb. 8, 2021 including the supplementary European search report received in European Patent Application No. 18813736.8.
Musah, S. et al., "Mature induced-pluripotent-stem-cell-derived human podocytes reconstitute kidney glomerular-capillary-wall function on a chip," *Nature Biomedical Engineering*, 1(5):12 pgs. (2017).
Homan, K., et al., "Fluidic shear stress induces vascular and glomerular develoement in kidney organoids," *J Am Soc Nephrol*, 28:62-63 (2017).
Homan, K.A., et al., "Flow-enhanced vascularization and maturation of kidney organoids in vitro," *Nature Methods*, 16(3):255-262 (2019).
Notification of The Decision Of Final Rejection received in corresponding Chinese Patent Application No. 201880038158.4, dated Jul. 5, 2022 (in Chinese and including English translation).
Examination Report No. 1 for standard patent application received in Australian Patent Application No. 2018279738 dated Aug. 2, 2022 (3 pages), and email from Australian agent mailed Nov. 17, 2022 reporting the Examination Report No. 1 (3 pages).
First Office Action received in the European Patent Application No. 18813736.8 dated Jan. 2, 2024 (4 pages).

\* cited by examiner

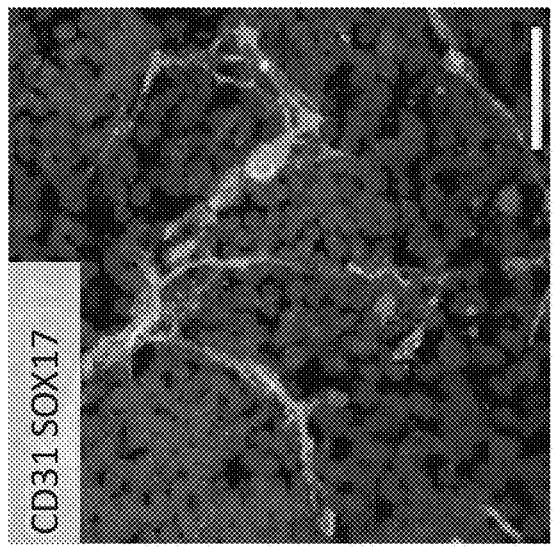
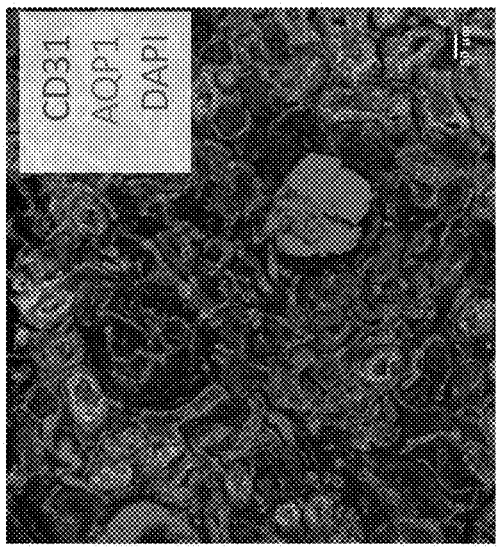
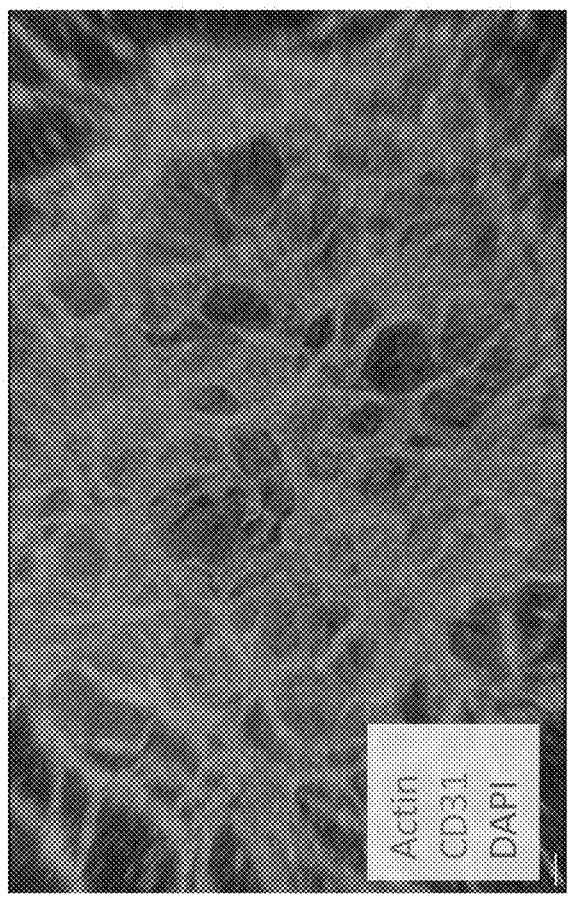
Figure 5B
Figure 5C
Figure 5A

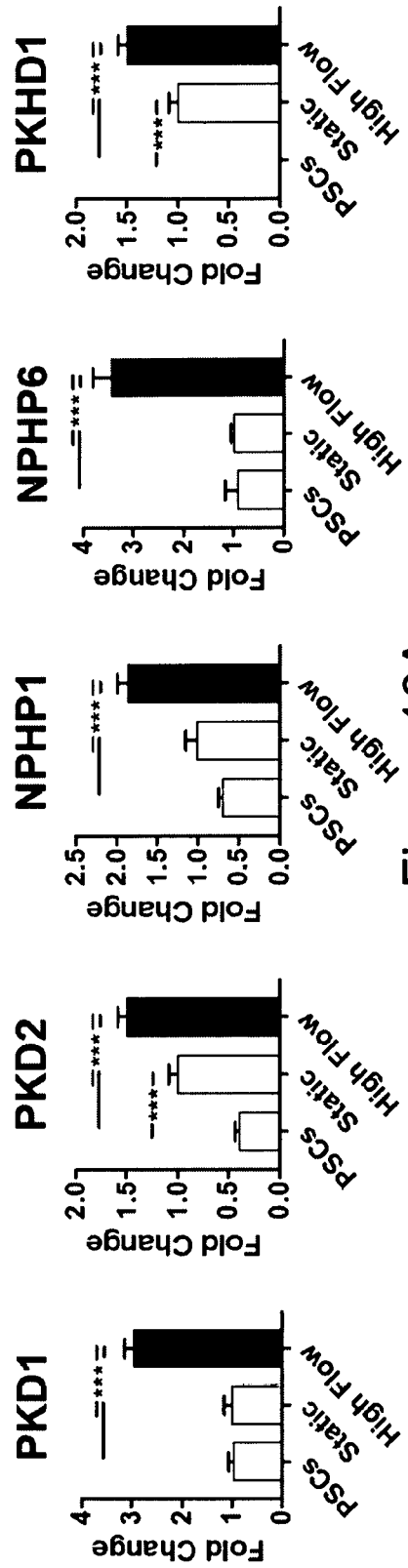
Figure 16A
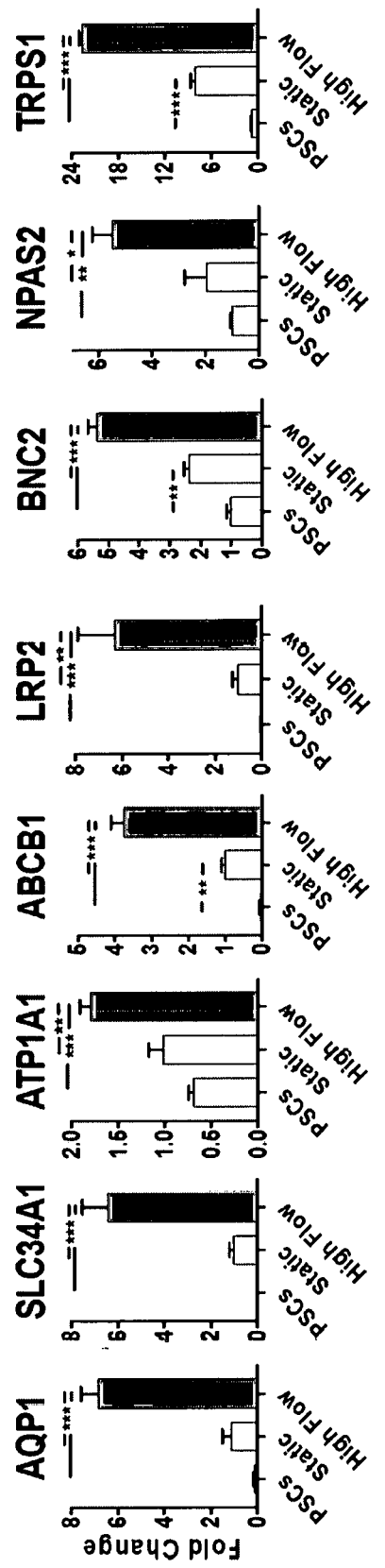
Figure 16B
Figure 16C

SEQUENCE LISTING

<160> NUMBER OF SEQ ID NOS: 58

<210> SEQ ID NO 1
<211> LENGTH: 20
<212> TYPE: DNA
<213> ORGANISM: Artificial Sequence
<220> FEATURE:
<223> OTHER INFORMATION: Forward primer for ABCB1 gene

<400> SEQUENCE: 1
ccatgctcag acaggatgtg                                          20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for ABCB1 gene

<400> SEQUENCE: 2
ttcctgtccc aagatttgct                                          20

<210> SEQ ID NO 3
<211> LENGTH: 20
<212> TYPE: DNA
<213> ORGANISM: Artificial Sequence
<220> FEATURE:
<223> OTHER INFORMATION: Forward primer for AQP1 gene

<400> SEQUENCE: 3
gtccaggaca acgtgaaggt                                          20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for AQP1 gene

<400> SEQUENCE: 4
gaggaggtga tgcctgagag                                          20

<210> SEQ ID NO 5
<211> LENGTH: 20

-continued

```
<212> TYPE: DNA
<213> ORGANISM: Artificial Sequence
<220> FEATURE:
<223> OTHER INFORMATION: Forward primer for ATP1A1 gene

<400> SEQUENCE: 5
ccaattgtgt tgaaggcacc                                              20

<210> SEQ ID NO 6
<211> LENGTH: 23
<212> TYPE: DNA
<213> ORGANISM: Artificial Sequence
<220> FEATURE:
<223> OTHER INFORMATION: Reverse primer for ATP1A1 gene

<400> SEQUENCE: 6
ccgtgatgat gtggataaaa tgt                                          23

<210> SEQ ID NO 7
<211> LENGTH: 21
<212> TYPE: DNA
<213> ORGANISM: Artificial Sequence
<220> FEATURE:
<223> OTHER INFORMATION: Forward primer for BNC2 gene

<400> SEQUENCE: 7
ctatgttcta gcccagaccc c                                            21

<210> SEQ ID NO 8
<211> LENGTH: 22
<212> TYPE: DNA
<213> ORGANISM: Artificial Sequence
<220> FEATURE:
<223> OTHER INFORMATION: Reverse primer for BNC2 gene

<400> SEQUENCE: 8
tatgttggca ctgtgtctgt ct                                           22

<210> SEQ ID NO 9
<211> LENGTH: 20
<212> TYPE: DNA
<213> ORGANISM: Artificial Sequence
<220> FEATURE:
<223> OTHER INFORMATION: Forward primer for CASZ1 gene

<400> SEQUENCE: 9
cactgtcaag aacggactgc                                              20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for CASZ1 gene

<400> SEQUENCE: 10
acgtcctgct tactcgtgaa                                              20

<210> SEQ ID NO 11
<211> LENGTH: 25
<212> TYPE: DNA
<213> ORGANISM: Artificial Sequence
<220> FEATURE:
<223> OTHER INFORMATION: Forward primer for CUX1 gene

<400> SEQUENCE: 11
```

```
gctgaagtga aaaatcaaga ggtta                                         25

<210> SEQ ID NO 12
<211> LENGTH: 20
<212> TYPE: DNA
<213> ORGANISM: Artificial Sequence
<220> FEATURE:
<223> OTHER INFORMATION: Reverse primer for CUX1 gene

<400> SEQUENCE: 12
gctttgaggt ggtggacatc                                               20

<210> SEQ ID NO 13
<211> LENGTH: 20
<212> TYPE: DNA
<213> ORGANISM: Artificial Sequence
<220> FEATURE:
<223> OTHER INFORMATION: Forward primer for GAPDH gene

<400> SEQUENCE: 13
caatgacccc ttcattgacc                                               20

<210> SEQ ID NO 14
<211> LENGTH: 20
<212> TYPE: DNA
<213> ORGANISM: Artificial Sequence
<220> FEATURE:
<223> OTHER INFORMATION: Reverse primer for GAPDH gene

<400> SEQUENCE: 14
gacaagcttc ccgttctcag                                               20

<210> SEQ ID NO 15
<211> LENGTH: 22
<212> TYPE: DNA
<213> ORGANISM: Artificial Sequence
<220> FEATURE:
<223> OTHER INFORMATION: Forward primer for KDR gene

<400> SEQUENCE: 15
aggacttcca gggaggaaat aa                                            22

<210> SEQ ID NO 16
<211> LENGTH: 22
<212> TYPE: DNA
<213> ORGANISM: Artificial Sequence
<220> FEATURE:
<223> OTHER INFORMATION: Reverse primer for KDR gene

<400> SEQUENCE: 16
aaagtaattt caggacccct gg                                            22

<210> SEQ ID NO 17
<211> LENGTH: 20
<212> TYPE: DNA
<213> ORGANISM: Artificial Sequence
<220> FEATURE:
<223> OTHER INFORMATION: Forward primer for LRP2 gene

<400> SEQUENCE: 17
tgtgatgcag ccatcgaact                                               20

<210> SEQ ID NO 18
<211> LENGTH: 20
<212> TYPE: DNA
<213> ORGANISM: Artificial Sequence
```

```
<220> FEATURE:
<223> OTHER INFORMATION: Reverse primer for LRP2 gene

<400> SEQUENCE: 18
tgcatttggg gaggtcagtc                                               20

<210> SEQ ID NO 19
<211> LENGTH: 21
<212> TYPE: DNA
<213> ORGANISM: Artificial Sequence
<220> FEATURE:
<223> OTHER INFORMATION: Forward primer for MCAM gene

<400> SEQUENCE: 19
cgtctcgtaa gagcgaactt g                                             21

<210> SEQ ID NO 20
<211> LENGTH: 22
<212> TYPE: DNA
<213> ORGANISM: Artificial Sequence
<220> FEATURE:
<223> OTHER INFORMATION: Reverse primer for MCAM gene

<400> SEQUENCE: 20
cgatgtattt ctctccctgg tc                                            22

<210> SEQ ID NO 21
<211> LENGTH: 20
<212> TYPE: DNA
<213> ORGANISM: Artificial Sequence
<220> FEATURE:
<223> OTHER INFORMATION: Forward primer for NFIA gene

<400> SEQUENCE: 21
acaggtgggg ttcctcaatc                                               20

<210> SEQ ID NO 22
<211> LENGTH: 19
<212> TYPE: DNA
<213> ORGANISM: Artificial Sequence
<220> FEATURE:
<223> OTHER INFORMATION: Reverse primer for NFIA gene

<400> SEQUENCE: 22
tgggtgtcga gtaggttgg                                                19

<210> SEQ ID NO 23
<211> LENGTH: 23
<212> TYPE: DNA
<213> ORGANISM: Artificial Sequence
<220> FEATURE:
<223> OTHER INFORMATION: Forward primer for NPAS2 gene

<400> SEQUENCE: 23
ttttgcagaa acacaatgaa gtc                                           23

<210> SEQ ID NO 24
<211> LENGTH: 19
<212> TYPE: DNA
<213> ORGANISM: Artificial Sequence
<220> FEATURE:
<223> OTHER INFORMATION: Reverse primer for NPAS2 gene

<400> SEQUENCE: 24
ccaaggagag gcgtgatac                                                19
```

```
<210> SEQ ID NO 25
<211> LENGTH: 21
<212> TYPE: DNA
<213> ORGANISM: Artificial Sequence
<220> FEATURE:
<223> OTHER INFORMATION: Forward primer for NPHP1 gene

<400> SEQUENCE: 25
accggtgaag aatacatcgc t                                                  21

<210> SEQ ID NO 26
<211> LENGTH: 25
<212> TYPE: DNA
<213> ORGANISM: Artificial Sequence
<220> FEATURE:
<223> OTHER INFORMATION: Reverse primer for NPHP1 gene

<400> SEQUENCE: 26
tataaggctc taggtaggtt ctggg                                              25

<210> SEQ ID NO 27
<211> LENGTH: 20
<212> TYPE: DNA
<213> ORGANISM: Artificial Sequence
<220> FEATURE:
<223> OTHER INFORMATION: Forward primer for NPHP6 gene

<400> SEQUENCE: 27
aggataccaa aggagcccaa                                                    20

<210> SEQ ID NO 28
<211> LENGTH: 23
<212> TYPE: DNA
<213> ORGANISM: Artificial Sequence
<220> FEATURE:
<223> OTHER INFORMATION: Reverse primer for NPHP6 gene

<400> SEQUENCE: 28
tcttcaagac tgctgattgt acg                                                23

<210> SEQ ID NO 29
<211> LENGTH: 20
<212> TYPE: DNA
<213> ORGANISM: Artificial Sequence
<220> FEATURE:
<223> OTHER INFORMATION: Forward primer for NPHS1 gene

<400> SEQUENCE: 29
gacccagctt cccatcacta                                                    20

<210> SEQ ID NO 30
<211> LENGTH: 20
<212> TYPE: DNA
<213> ORGANISM: Artificial Sequence
<220> FEATURE:
<223> OTHER INFORMATION: Reverse primer for NPHS1 gene

<400> SEQUENCE: 30
gcattggaga ggagcagaag                                                    20

<210> SEQ ID NO 31
<211> LENGTH: 21
<212> TYPE: DNA
<213> ORGANISM: Artificial Sequence
<220> FEATURE:
<223> OTHER INFORMATION: Forward primer for PECAM1 gene
```

```
<400> SEQUENCE: 31
tcattacggt cacaatgacg a                                              21

<210> SEQ ID NO 32
<211> LENGTH: 20
<212> TYPE: DNA
<213> ORGANISM: Artificial Sequence
<220> FEATURE:
<223> OTHER INFORMATION: Reverse primer for PECAM1 gene

<400> SEQUENCE: 32
gagtatctgc tttccacggc                                                20

<210> SEQ ID NO 33
<211> LENGTH: 20
<212> TYPE: DNA
<213> ORGANISM: Artificial Sequence
<220> FEATURE:
<223> OTHER INFORMATION: Forward primer for PDGFR-Beta gene

<400> SEQUENCE: 33 ataccccgc aaagaaagtg                                                 20

<210> SEQ ID NO 34
<211> LENGTH: 20
<212> TYPE: DNA
<213> ORGANISM: Artificial Sequence
<220> FEATURE:
<223> OTHER INFORMATION: Reverse primer for PDGFR-Beta gene

<400> SEQUENCE: 34
cactctccgt cacattgcag                                                20

<210> SEQ ID NO 35
<211> LENGTH: 20
<212> TYPE: DNA
<213> ORGANISM: Artificial Sequence
<220> FEATURE:
<223> OTHER INFORMATION: Forward primer for PKD1 gene

<400> SEQUENCE: 35
aacaagtctt tggccatcac                                                20

<210> SEQ ID NO 36
<211> LENGTH: 20
<212> TYPE: DNA
<213> ORGANISM: Artificial Sequence
<220> FEATURE:
<223> OTHER INFORMATION: Reverse primer for PKD1 gene

<400> SEQUENCE: 36
tactcgttca gcacggtgac                                                20

<210> SEQ ID NO 37
<211> LENGTH: 20
<212> TYPE: DNA
<213> ORGANISM: Artificial Sequence
<220> FEATURE:
<223> OTHER INFORMATION: Forward primer for PKD2 gene

<400> SEQUENCE: 37
tcttggcaat ttcagccttt                                                20

<210> SEQ ID NO 38
```

<211> LENGTH: 20
<212> TYPE: DNA
<213> ORGANISM: Artificial Sequence
<220> FEATURE:
<223> OTHER INFORMATION: Reverse primer for PKD2 gene

<400> SEQUENCE: 38
gcacaacgat cacaacatcc                                         20

<210> SEQ ID NO 39
<211> LENGTH: 20
<212> TYPE: DNA
<213> ORGANISM: Artificial Sequence
<220> FEATURE:
<223> OTHER INFORMATION: Forward primer for PKHD1 gene

<400> SEQUENCE: 39
ccattctctg ccaggttagc                                         20

<210> SEQ ID NO 40
<211> LENGTH: 20
<212> TYPE: DNA
<213> ORGANISM: Artificial Sequence
<220> FEATURE:
<223> OTHER INFORMATION: Reverse primer for PKHD1 gene

<400> SEQUENCE: 40
acccctaatc agcacagtgg                                         20

<210> SEQ ID NO 41
<211> LENGTH: 23
<212> TYPE: DNA
<213> ORGANISM: Artificial Sequence
<220> FEATURE:
<223> OTHER INFORMATION: Forward primer for SLC2A2 gene

<400> SEQUENCE: 41
gctgctgaat aagttctctt gga                                     23

<210> SEQ ID NO 42
<211> LENGTH: 20
<212> TYPE: DNA
<213> ORGANISM: Artificial Sequence
<220> FEATURE:
<223> OTHER INFORMATION: Reverse primer for SLC2A2 gene

<400> SEQUENCE: 42
ctaaagcagc aggacgtggt                                         20

<210> SEQ ID NO 43
<211> LENGTH: 20
<212> TYPE: DNA
<213> ORGANISM: Artificial Sequence
<220> FEATURE:
<223> OTHER INFORMATION: Forward primer for SLC6A19 gene

<400> SEQUENCE: 43
acaactgcga gaaggactcg                                         20

<210> SEQ ID NO 44
<211> LENGTH: 20
<212> TYPE: DNA
<213> ORGANISM: Artificial Sequence
<220> FEATURE:
<223> OTHER INFORMATION: Reverse primer for SLC6A19 gene

<400> SEQUENCE: 44

-continued gtgctgaagc agtcgtcgta                                              20

<210> SEQ ID NO 45
<211> LENGTH: 21
<212> TYPE: DNA
<213> ORGANISM: Artificial Sequence
<220> FEATURE:
<223> OTHER INFORMATION: Forward primer for SLC9A3 gene

<400> SEQUENCE: 45
ggcaggagta caagcatctg t                                            21

<210> SEQ ID NO 46
<211> LENGTH: 19
<212> TYPE: DNA
<213> ORGANISM: Artificial Sequence
<220> FEATURE:
<223> OTHER INFORMATION: Reverse primer for SLC9A3 gene

<400> SEQUENCE: 46
cccggtcctg tttctcgtc                                               19

<210> SEQ ID NO 47
<211> LENGTH: 20
<212> TYPE: DNA
<213> ORGANISM: Artificial Sequence
<220> FEATURE:
<223> OTHER INFORMATION: Forward primer for SLC34A1 gene

<400> SEQUENCE: 47
tcacgaagct catcatccag                                              20

<210> SEQ ID NO 48
<211> LENGTH: 20
<212> TYPE: DNA
<213> ORGANISM: Artificial Sequence
<220> FEATURE:
<223> OTHER INFORMATION: Reverse primer for SLC34A1 gene

<400> SEQUENCE: 48
ttcctcaggg actcatcacc                                              20

<210> SEQ ID NO 49
<211> LENGTH: 20
<212> TYPE: DNA
<213> ORGANISM: Artificial Sequence
<220> FEATURE:
<223> OTHER INFORMATION: Forward primer for SYNPO gene

<400> SEQUENCE: 49
gccgcaaatc catgtttact                                              20

<210> SEQ ID NO 50
<211> LENGTH: 20
<212> TYPE: DNA
<213> ORGANISM: Artificial Sequence
<220> FEATURE:
<223> OTHER INFORMATION: Reverse primer for SYNPO gene

<400> SEQUENCE: 50
ctcatccgct gtctgtacca                                              20

<210> SEQ ID NO 51
<211> LENGTH: 19
<212> TYPE: DNA

```
<213> ORGANISM: Artificial Sequence
<220> FEATURE:
<223> OTHER INFORMATION: Forward primer for TEAD1 gene

<400> SEQUENCE: 51
caaggtttga gaatggccg                                                   19

<210> SEQ ID NO 52
<211> LENGTH: 21
<212> TYPE: DNA
<213> ORGANISM: Artificial Sequence
<220> FEATURE:
<223> OTHER INFORMATION: Reverse primer for TEAD1 gene

<400> SEQUENCE: 52
tccctgtttg ttaccaccaa t                                                21

<210> SEQ ID NO 53
<211> LENGTH: 21
<212> TYPE: DNA
<213> ORGANISM: Artificial Sequence
<220> FEATURE:
<223> OTHER INFORMATION: Forward primer for TRPS1 gene

<400> SEQUENCE: 53
tttcccgaca ctacaggaga g                                                21

<210> SEQ ID NO 54
<211> LENGTH: 20
<212> TYPE: DNA
<213> ORGANISM: Artificial Sequence
<220> FEATURE:
<223> OTHER INFORMATION: Reverse primer for TRPS1 gene

<400> SEQUENCE: 54
ccgttggctg tagtgatgtc                                                  20

<210> SEQ ID NO 55
<211> LENGTH: 23
<212> TYPE: DNA
<213> ORGANISM: Artificial Sequence
<220> FEATURE:
<223> OTHER INFORMATION: Forward primer for VEGFA gene

<400> SEQUENCE: 55
gtccaacatc accatgcaga tta                                              23

<210> SEQ ID NO 56
<211> LENGTH: 21
<212> TYPE: DNA
<213> ORGANISM: Artificial Sequence
<220> FEATURE:
<223> OTHER INFORMATION: Reverse primer for VEGFA gene

<400> SEQUENCE: 56
gctgtaggaa gctcatctct c                                                21

<210> SEQ ID NO 57
<211> LENGTH: 20
<212> TYPE: DNA
<213> ORGANISM: Artificial Sequence
<220> FEATURE:
<223> OTHER INFORMATION: Forward primer for WT1 gene

<400> SEQUENCE: 57
gggtacgaga gcgataacca                                                  20
```

```
<210> SEQ ID NO 58
<211> LENGTH: 20
<212> TYPE: DNA
<213> ORGANISM: Artificial Sequence
<220> FEATURE:
<223> OTHER INFORMATION: Reverse primer for WT1 gene

<400> SEQUENCE: 58
tctcaccagt gtgcttcctg                                              20
```

METHODS OF ENHANCING DEVELOPMENT OF RENAL ORGANOIDS AND METHODS OF USING THE SAME

RELATED APPLICATIONS

The present patent document is a § 371 filing based on PCT Application Serial No. PCT/US2018/036677, filed Jun. 8, 2018, which claims the benefit of the filing date under 35 U.S.C. § 119(e) of Provisional U.S. Patent Application Ser. No. 62/517,536, filed Jun. 9, 2017, which is hereby incorporated by reference.

FEDERALLY SPONSORED RESEARCH OR DEVELOPMENT

This invention was made with Government support under contract numbers DK007527, U01DK107350, DK039773, and TR002155 awarded by the National Institutes of Health (NIH); contract number U01DK107350, awarded by the NIH (Re)Building a Kidney Consortium; contract number N000141612823, awarded by the Office of Naval Research Vannevar Bush Faculty Fellowship Program; and contract number P30 DK079333, awarded by the NIH supporting The Washington University KTRC.

REFERENCE TO SEQUENCE LISTING SUBMITTED VIA EFS-WEB

This application is being filed electronically via EFS-Web and includes an electronically submitted Sequence Listing in .txt format. The .txt file contains a sequence listing "HU6909SequenceListing" created on Jun. 7, 2018 and is 12,000 bytes in size. The sequence listing contained in this .txt file is part of the specification and is hereby incorporated by reference in its entirety.

BACKGROUND

Described are methods of enhancing development of renal organoids, and methods of using the same.

Chronic Kidney Disease (CKD) affects over 19 million people in the United States and is frequently a consequence of metabolic disorders involving obesity, diabetes, and hypertension. The rate of increase is due to the development of renal failure secondary to hypertension and non-insulin dependent diabetes mellitus. For example, one out of three people with diabetes develops kidney disease.

Over 2 million people now require renal replacement therapy to sustain life worldwide, but this likely represents less than 10% of those who need it. Another 112 countries, with a combined population of over 600 million people, cannot afford renal replacement at all, resulting in the death of over 1 million people annually from untreated kidney failure.

Chronic renal failure is prevalent in humans and some domesticated animals. Patients with renal failure experience not only the loss of kidney function (uremia), but also develop anemia due to the inability of the bone marrow to produce a sufficient number of red blood cells (RBCs) via erythropoiesis.

To date, clinical approaches to the treatment of chronic renal failure involved dialysis and kidney transplantation for restoration of renal filtration and urine production, and the systemic delivery of recombinant erythropoietin (EPO) or EPO analogs to restore erythroid mass. Dialysis offers survival benefit to patients in mid-to-late stage renal failure, but causes significant quality of life issues. Kidney transplant is a highly desired (and often the only) option for patients in the later stages of renal failure, however, the supply of high-quality donor kidneys does not meet the demand of the renal failure population. For example, there are currently over 100 thousand people waiting for kidney transplant in the U.S.

Renal organoids, derived from, e.g., human pluripotent stem cells (hPSCs), provide a novel platform to study basic kidney development, drug toxicity, and disease modeling. Further, they can be used as building block to create larger kidney tissues and new kidney regenerative therapies, both from autologous and allogeneic sources. The cellular heterogeneity and tubular architectures recapitulated in these systems are noteworthy, and recent studies demonstrated that vascularized glomeruli can be formed with host endothelial cells upon transplantation of organoid-derived podocytes to SCID mice. However, in the current organoid systems in vitro, glomerular development is imperfect and vasculature is neither perfusable nor remains viable longitudinally, limiting both the degree of relevant applications, and their translatability to human physiology in vivo.

As such, there still exists a need for methods to enhance kidney organoids and overcome these limitations. Enhanced kidney organoids with a perfusable vascular networks which better mimic in vivo development could be used in a wide array of applications including but not limited to kidney disease modeling, glomerular disease modeling, drug toxicology studies, models for drug screening, living dialysis devices, dialysis assist devices, and regenerative applications where these constructs could be implanted to replace some or all kidney functions.

SUMMARY

Certain embodiments relate to a method of generating a vascularized renal tissue construct, an organoid, or an organoid in a construct, comprising culturing a population of cells in a cell culture medium to produce a developing organoid, and exposing the developing organoid to fluid perfusion to impart wall shear or in other words, fluidic shear stress (FSS). Imparting FSS induces vascular development and tubular and glomerular maturation in the renal organoid, thereby producing a vascularized renal tissue construct, organoid, or the organoid in the construct. The population of cells can include at least one of pluripotent stem cells, multipotent stem cells, progenitor cells, terminally differentiated cells, endothelial cells, endothelial progenitor cells, nephron progenitor cells, immortalized cell lines, or primary cells. The population of cells comprises at least one of human embryonic stem cells (hESCs) or induced pluripotent stem cells (hiPSCs). In the method, the culturing is while imparting the FSS. In the method, the culturing takes place on a perfusable chip or rocking dish with a substrate or by using a spinning bioreactor. The underlying substrate may be plastic, acrylic, quartz, or glass. The underlying substrate may be plasma-treated or coated with a layer of at least one of a solubilized basement membrane matrix secreted by Engelbreth-Holm-Swarm (EHS) mouse sarcoma cells (Matrigel™), poly L-lysine, reduced growth factor basement membrane matrix (Geltrex™), gelatin, nitrogen, fibronectin, collagen I, collagen IV, fibrinogen, gelatin methacrylate, fibrin, silk, pegylated gels, collagen methacrylate, basement membrane proteins, or any other biomaterial. The substrate may be any combination of gelatin, fibrin, or collagen I, or any other basement membrane proteins. In the method, the culturing while imparting FSS is for at least 1 day to a maximum of 200 days. The method may further comprise embedding the developing organoid in an extracellular matrix material (ECM) or substrate, wherein embedding comprises at least one of placing the developing organoid on top of the ECM or embedding the developing organoid within the ECM. The extracellular matrix material may be at least one of Matrigel™, poly L-lysine, Geltrex™, gelatin, nitrogen, fibronectin, collagen I, collagen IV, fibrinogen, gelatin methacrylate, fibrin, silk, pegylated gels, collagen methacrylate, basement membrane proteins, or any other biomaterial, or a combination thereof. The cell culture medium may comprise at least one of base media, fetal bovine serum (FBS), FGF9, CH1R, dorsomorphin, Activin A, or retinoic acid. The concentration of the FBS may be in the range from about 0.1% to about 10% FBS. The concentration of the FBS may be in the range from about 1% to about 2% FBS. The concentration of the FBS may be about 1.5% FBS. In the method, the fluid perfusion is at FSS from about 0.001 dyn/cm$^2$ to about 50 dyn/cm$^2$; alternatively, the perfusion is at FSS from about 0.01 dyn/cm$^2$ to about 10 dyn/cm$^2$. In the method, the exposing step comprises a continuous or constant imparting of the FSS anywhere from 1 to 200 days. In the method, the FSS may be pulsed to mimic blood pressure changes during regular heartbeats. The method may further comprise exposing the developing organoid to one or more biological agents, a biological agent gradient, a pressure, and/or an oxygen tension gradient, thereby inducing angiogenesis, vasculugenesis, or tubulogensis of capillary vessels to and/or from the renal organoid. The one or more biological agents, the biological agent gradient, the pressure, and/or the oxygen tension gradient may further direct development, differentiation, and/or functioning of the developing organoid. The method may further comprise embedding the developing organoid in the tissue construct, wherein the embedding the developing organoid in the tissue construct comprises: depositing one or more sacrificial filaments on the substrate to form a vascular pattern, each of the sacrificial filaments comprising a fugitive ink; depositing or printing the developing organoid within the vascular pattern; at least partially surrounding the vascular pattern and/or the developing organoid with an extracellular matrix composition; and removing the fugitive ink, thereby forming the tissue construct comprising the developing organoid embedded or partially embedded therein.

Certain further embodiments relate to a vascularized renal tissue construct, an organ, or a living device produced by the methods described herein.

Certain further embodiments relate to a use of the vascularized renal tissue construct, organoid, an organoid in a construct, organ, or a living device produced by the methods described herein in glomerular disease modeling, tubule disease modeling, vascular disease modeling, immune reaction modeling, fibrosis modeling, drug toxicity studies, drug screening applications, living dialysis devices, reabsorption devices, and/or as kidney tissue for replacement of kidneys (regenerative medicine).

Certain additional embodiments relate to a kit comprising a vascularized renal tissue construct or organoid produced by the method described herein, and an enclosure with a single inlet and single outlet for media. The kit may also comprise media and/or a perfusion pump, and/or instructions for using the kit.

Certain further embodiments relate to a kit comprising a vascularized renal tissue construct or organoid produced by the methods described herein and an enclosure with a single inlet and two outlets. The kit may also comprise media, and/or a perfusion pump, and/or instructions for using the kit.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5A depicts exemplary organoids produced by the methods described herein as compared to the prior art organoids shown in FIG. 5B (Takasato, M., Little, M. H., Dev. Biol. (2016)) and human adult kidney tissue in FIG. 5C.

FIGS. 16A, 16B, 16C and 16D further show that tubular epithelia mature and undergo morphogenesis to become a polarized, ciliated compartment in contact with vasculature in response to the high flow condition on chip: (A-C) qPCR of ciliary markers, solute transporters, drug transporters, and adult transcription factors showing upregulation under high flow on day 21, compared to static conditions on chip and undifferentiated hPSCs; (D) whole organoid 3D confocal imaging stacks (di, all scale bars=50 μm) of a representative high flow sample are used to demonstrate the analysis method for the association of tubules with vasculature in Imaris 3D surface rendering ($d_{ii}$ and $d_{iii}$) and distance transformation software ($d_{iv}$ and $d_v$) to find in (FIG. 17(c)) that the percent of vasculature surface area overlapping with LTL+ tubules within one voxel is significantly increased under high flow than in static conditions. Further, that tight vasculotubular association can be negated by dosing high amounts of VEGF or adding VEGF inhibitor in the media.

DETAILED DESCRIPTION OF THE DRAWINGS AND THE PRESENTLY PREFERRED EMBODIMENTS

Figure 1:
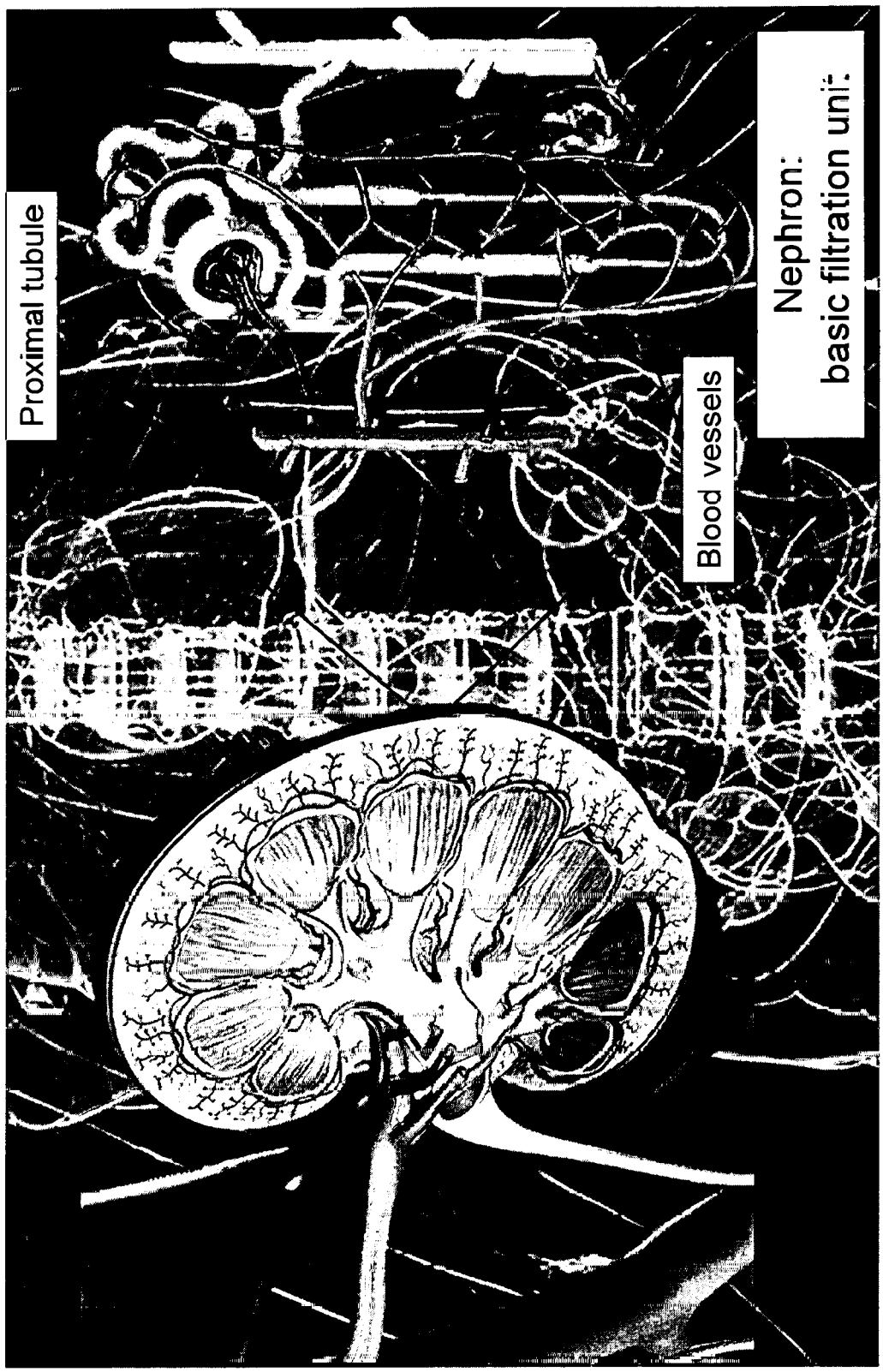
FIG. 1 is a schematic illustration of the kidney and its basic filtration unit, the nephron.

International Patent Application No. PCT/US2014/063810, filed on Nov. 4, 2014; International Patent Application No. PCT/US2016/20601, filed Mar. 3, 2016; International Patent Application No. PCT/US2016/30710, filed May 4, 2016; U.S. Provisional Patent Application No. 61/900,029, filed on Nov. 5, 2013; U.S. Provisional Patent Application No. 62/127,549, filed Mar. 3, 2015; and U.S. Provisional Patent Application No. 62/250,338, filed on Nov. 3, 2015; Provisional U.S. Patent Application Ser. No. 62/157,286, filed May 5, 2015; Provisional U.S. Patent Application Ser. No. 62/383,928, filed Sep. 6, 2016, all are hereby incorporated by reference in their entirety.

Also, PCT Publication No. WO 2015/057261 and Morizane et al. Nature Biotechnology (2015), are incorporated by reference herein in their entirety.

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

To date, renal organoids were found to lack a robust vasculature and glomerular development. Further limitations of previously developed organoids are that vasculature develops naturally, then dies; capillary loops in glomeruli do not form properly in vitro; and these organoids have limited internal perfusion through tubular and vascular structures.

Kidney organoids in static culture exhibit immature vascularization and gene expression compared to human adult kidneys (Takasato, M. et al., "Kidney organoids from human iPS cells contain multiple lineages and model human nephrogenesis," Nature 526, 564-568 (2015); and Wu, H., et al., "Comparative analysis of kidney organoid and adult human kidney single cell and single nucleus transcriptomes," bioRxiv, doi:10.1101/232561 (2017)). Given that multilineage communication with vasculature is implicated in epithelial maturation in vivo (Camp, J. G., et al., "Multilineage communication regulates human liver bud development from pluripotency," Nature 546, 533-538 (2017)), it was hypothesized that enhanced vascularization and maturation may be promoted in hPSC-derived human kidney tissue in vitro when subject to environmental cues. To test our hypothesis, a fluidic culture system was developed to probe the effects of myriad compositions of extracellular matrices (ECM) and media, variable fluidic shear stress (FSS), and co-culture with human endothelial cells in developing kidney organoids.

First, to tease out the variables, several questions were considered, including: does incorporation of GMECs matter, what effect do the chemical additives have on the development of the organoids, does the age of the RV matter, what is the effect of perfusion (direct or indirect), and what is the effect of the underlying substrate.

Surprisingly, it was discovered presently that when FSS is applied to developing organoids, vascular density is increased, including vascular integration in the glomerulus and vasculature associating with tubules.

Figure 3:
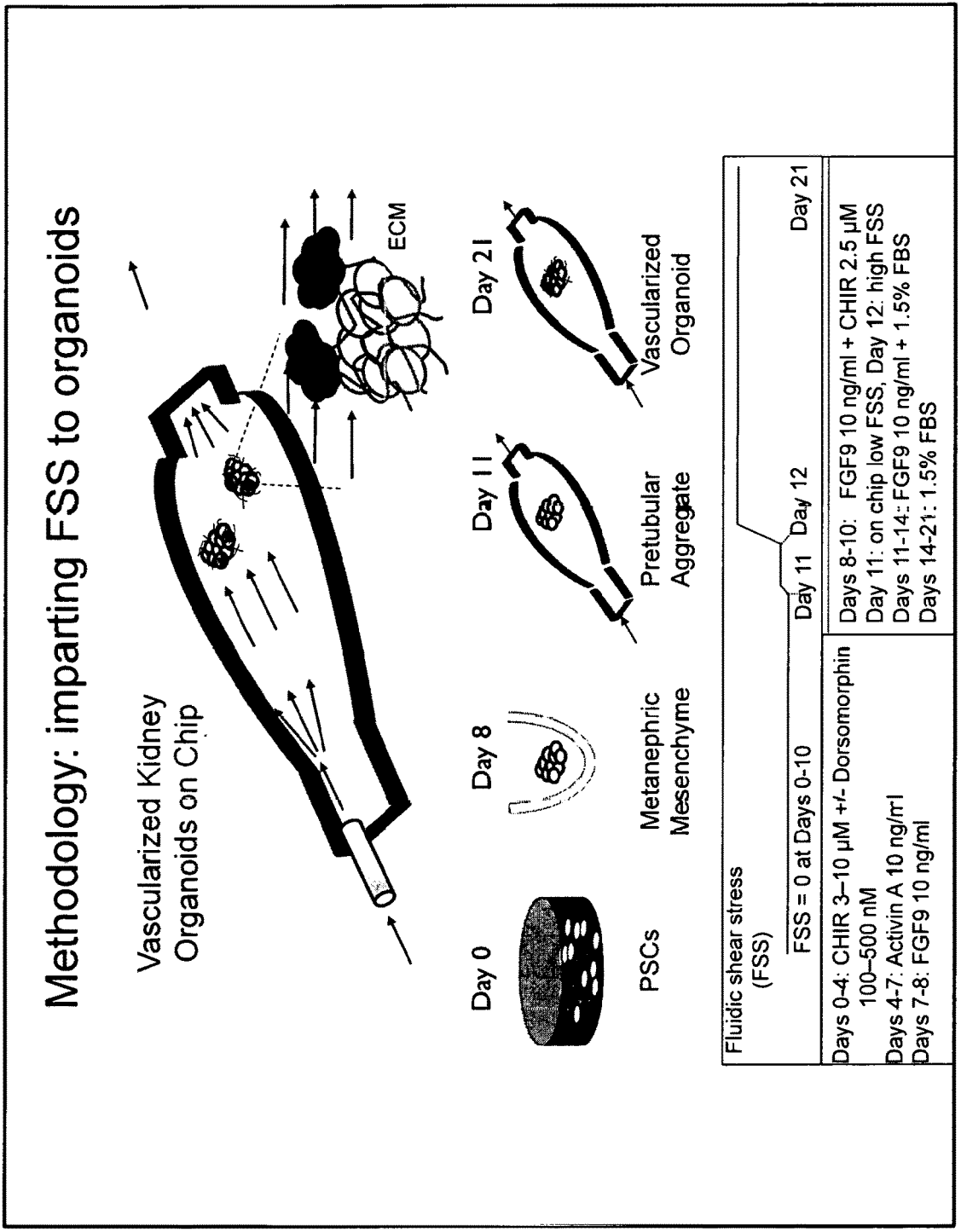
FIG. 3 depicts a schematic illustration of the described methodology of imparting fluidic shear stress (FSS) to developing organoids or organoids during the differentiation and maturation process.

Described herein are methods for producing vascularized renal organoids of enhanced glomerular and tubular maturity or renal tissue constructs made of organoids of enhanced maturity, using FSS. FIG. 3 depicts an exemplary schematic illustration of the present methodology of imparting FSS to developing organoids to produce vascularized renal organoids of enhanced glomerular and tubular maturity or renal tissue constructs made of organoids of enhanced maturity. The method includes culturing a population of cells in a cell culture medium to produce a developing organoid, and exposing the developing organoid to fluid perfusion to impart FSS to induce vascular development and tubular and glomerular maturation in the organoid, thereby producing the vascularized renal tissue constructs or organoids.

In certain embodiments, the developing renal organoids are placed on an engineered extracellular matrix (ECM), housed within a customized perfusion chip, and subjected to controlled flow and FSS. See FIGS. 3 and 4.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, compositions, devices and materials are described herein.

As used herein and in the appended claims, the singular forms "a," "and," and "the" include plural referents unless the context clearly dictates otherwise. Thus, for example, reference to "a protein" includes a plurality of such proteins and reference to "the progenitor cell" includes reference to one or more progenitor cells known to those skilled in the art, and so forth.

The terms "renal tissue construct," "renal organoid," "developing organoid" or "pretubular aggregate" can be used interchangeably and refer to a three-dimensional tissue culture created or synthesized by culturing one or several types of cells, e.g., human pluripotent or multipotent stem cells on, e.g., a substrate that have undergone a degree of differentiation. Renal tissue constructs or renal organoids are formed into a three-dimensional sphere, spheroid, or other three dimensional shape. As the cells undergo differentiation, the renal organoid proceeds through several stages of development to form a vascularized renal organoids of enhanced glomerular and tubular maturity, or renal tissue constructs made of organoids of enhanced maturity. The term "renal tissue construct" also encompassed renal organoids embedded or printed into a tissue construct. Renal tissue constructs that contain organoids or organoids themselves have anatomical features that resemble mammalian kidneys, such as tubule structures (FIG. 1) as well as the same or similar, or partial functional features as the mammalian kidneys.

The term "vascularized organoid of enhanced glomerular and tubular maturity" refer to the renal tissue construct produced or synthesized by the methods described herein that includes anatomical features, including a vascular network that resembles mammalian kidneys.

An organoid is created by culturing at least one of pluripotent stem cells, multipotent stem cells, nephron progenitor cells, progenitor cells, terminally differentiated cells, endothelial cells, endothelial progenitor cells, immortalized cell lines, or primary cells, as described in detail below.

The term "embedding" in reference to "embedding the developing organoid in an extracellular matrix material (ECM)" refers to either placing the developing organoid(s) or organoids on top of the ECM or embedding them within the ECM or printing them into the ECM.

The term "embedding" in reference to "embedding an organoid into a tissue construct" refers to either placing the developing organoid(s) on top of the tissue construct, or embedding them within the tissue construct, or printing them into the tissue construct.

In one embodiment, a method of generating a vascularized renal tissue constructs or organoids includes the steps of culturing a population of cells in a cell culture medium to produce a developing organoid, and exposing the developing organoid to fluid perfusion to impart FSS to induce vascularization and enhanced glomerular and tubular development in the developing organoid, thereby producing the vascularized renal tissue construct or organoid.

Fluid flow is an essential feature of every microsystem involving cell handling, culture or sorting. Flows inevitably generates FSS. "Fluid shear stress" of "FSS" refer to the stress coplanar component along with a cross section of a material, also known as wall shear stress. This occurs due to the component's force vector that is analogous to the cross section. It is in contradiction to normal stress that arises from force vectors that are perpendicular to the material's cross section, where it acts.

The developing organoid is exposed to fluid perfusion to impart FSS to induce vascularization and enhanced glomerular and tubular development in the developing organoid.

The fluid perfusion may be at FSS anywhere from about 0.000001 dyn/cm$^2$ to about 100 dyn/cm$^2$; alternatively, the fluid perfusion may be at FSS from about 0.01 dyn/cm$^2$ to about 50 dyn/cm$^2$; alternatively, the fluid perfusion may be at FSS from about 0.01 dyn/cm$^2$ to about 10 dyn/cm$^2$; the fluid perfusion may be at FSS from about 0.01 dyn/cm$^2$ to about 5 dyn/cm$^2$; the fluid perfusion may be at FSS from about 0.01 dyn/cm$^2$ to about 1 dyn/cm$^2$ The exposure to FSS may be constant, continuous, or intermittent and can be for anywhere from 1 day to 200 days. In certain alternative embodiments, shear stress may also be pulsed to mimic blood pressure changes during regular heartbeats. In certain further embodiments, the FSS may be intermittent. The terms "constant" and "continuous" can be used interchangeably and refer to an uninterrupted and/or steady exposure to FSS for a specified and extended period of time (e.g., from 1 to 200 days). The term "intermittent" refers to an interrupted or unsteady exposure to FSS. In reference to the intermittent exposure, the developing organoid can be exposed to FSS in regular intervals, e.g., every 5 seconds, every 10 seconds, or every 15 seconds, etc., for a specified amount of time of exposure, e.g., for 1 second, for 2 seconds, for 3 seconds, for 4 seconds, for 5 seconds, etc., for a specified time period (e.g., from 1 to 200 days). Alternatively, in reference to the intermittent exposure, the developing organoids can be exposed to FSS in irregular intervals. The type of exposure to the FSS can be pre-programmed.

In certain embodiments, the step of culturing a population of cells may be while simultaneously imparting the FSS.

In certain embodiments, the culturing step takes place on a perfusable chip with an underlying substrate, or by using a spinning bioreactor, or a substrate in a rocking device such as an orbital shaker or rocker or similar devices.

The underlying substrate may be plastic, acrylic, quartz, or glass. The underlying substrate may be plasma-treated or coated with a layer of at least one of Matrigel™, poly L-lysine, Geltrex™, gelatin, nitrogen, fibronectin, collagen I, collagen IV, fibrinogen, gelatin methacrylate, fibrin, silk, pegylated gels, collagen methacrylate, basement membrane proteins, or any other biomaterial. The substrate may be any combination of gelatin, fibrin, or collagen I, or any other basement membrane proteins.

The population of cells may be at least one of: pluripotent stem cells, multipotent stem cells, progenitor cells, nephron progenitor cells, terminally differentiated cells, endothelial cells, endothelial progenitor cells, immortalized cell lines, or primary cells. In certain embodiments, the population of cells comprises at least one of human embryonic stem cells (hESCs) or induced pluripotent stem cells (hiPSCs).

The cells may be cultured for at least 1 day and can be cultured indefinitely, and until the culturing is no longer desired. In some embodiments, cultures of cells can be grown for 30 days or longer, e.g., the cells may be cultured for 2 months, 3 months, 6 months, 9 months, 12 months, 24 months, 30 months, 36 months, 42 months, etc. Any time periods in between the mentioned time periods for culturing the cells are also contemplated. For example, in certain embodiments, the cells may be cultured for at least 2 days, at least 3 days, at least 4 days, at least 5 days, at least 6 days, at least 7 days, at least 8 days, at least 9 days, at least 10 days, at least 11 days; at least 12 days; at least 13 days; at least 14 days; at least 15 days; at least 16 days; at least 17 days; at least 18 days; at least 19 days; at least 20 days; at least 21 days; at least 22 days; at least 23 days; at least 24 days; at least 25 days; at least 26 days; at least 27 days; at least 28 days; at least 29 days; at least 30 days; or at least 31 days; or longer.

In certain further embodiments, the methods may also include a step of embedding the developing organoid in an extracellular matrix material or ECM. "Embedding" may be by placing the developing organoid on top of the ECM, or embedding the developing organoid within the ECM, or both.

The ECM may be or may include at least one of Matrigel™, poly L-lysine, Geltrex™, gelatin, nitrogen, fibronectin, collagen I, collagen IV, fibrinogen, gelatin methacrylate, fibrin, silk, pegylated gels, collagen methacrylate, basement membrane proteins, or any other biomaterial, or a combination thereof.

The step of culturing a population of cells may be in a cell culture medium. The term "culture medium" has the common meanings understood by one of ordinary skill in the art. The cell culture medium may comprise at least one of base media, fetal bovine serum (FBS), FGF9, CH1R, dorsomorphin, Activin A, or retinoic acid. Exemplary culture mediums include for example, but are not limited to, Dulbecco's modified eagle medium (DMEM), Hank's balanced salt medium, Glasgow minimum essential medium, Ames medium, Click's medium, nutrient mixtures HAM F-10 and HAM F-12, Advanced RPMI, Apel, DMEM:F12. The terms "culture medium" and "culture media" are equivalent and can be used interchangeably. The exemplary cell culture medium for use in the described methods includes at least one of base media, fetal bovine serum (FBS), or FGF9.

In certain embodiments, the concentration of the FBS may be in the range from about 0. % to about 10% FBS. In other embodiments, the concentration of the FBS may be in the range from about 1% to about 2% FBS. In further embodiments, the concentration of the FBS may be about 1.5% FBS.

The PCT Publication WO 2017/049243 A1, which is incorporated herein in its entirety, provides exemplary concentrations of different media components that may be included in the media used in the methods described herein.

In certain additional embodiments, the method of generating a vascularized organoid or enhanced/vascularized renal tissue construct may also include a step of exposing the developing organoid to one or more biological agents, a biological agent gradient, a pressure, and/or an oxygen tension gradient, thereby inducing angiogenesis of capillary vessels to and/or from the renal organoid. The one or more biological agents, the biological agent gradient, the pressure, and/or the oxygen tension gradient further direct development, differentiation, and/or functioning of the developing organoid.

Exemplary biological agents may include vascular endothelial growth factor (VEGF) or PMA, FBS, or other proangiogenic stimulants.

In certain embodiments, the method of generating a vascularized organoid or enhanced/vascularized renal tissue construct may also include a step of exposing the developing organoid to a biological agent gradient. The term "biological agent gradient" refers to creating a gradient of distribution of growth factors in the tissue construct, which may impart chemoattractive properties for vasculature or tubules or both.

In certain embodiments, the method of generating a vascularized organoid or enhanced/vascularized renal tissue construct may also include a step of exposing the developing organoid to a pressure gradient across its width, thus causing the organoid to pattern expression of key subcomponents along the pressure gradient.

In certain embodiments, the method of generating a vascularized organoid or enhanced/vascularized renal tissue construct may also include a step of exposing the developing organoid to an oxygen tension gradient, or a tissue construct with areas of varying oxygen concentration.

In certain further embodiments, the method of generating a vascularized renal tissue construct may also include embedding the developing organoid in the tissue construct. This includes: depositing one or more sacrificial filaments on the substrate to form a vascular pattern, each of the sacrificial filaments comprising a fugitive ink; depositing or printing the developing organoid within the vascular pattern; at least partially surrounding the vascular pattern and/or the developing organoid with an extracellular matrix composition; and removing the fugitive ink, thereby forming the tissue construct comprising the developing organoid embedded therein. A filament "deposited on a substrate" may be understood to be deposited directly on the substrate or directly on another filament, channel or portion previously deposited or formed on the substrate.

The term "internal plexus" refers to an interconnected network of vascular endothelial cells that resides inside of, and/or on the surface of a developing organoid or organoid.

In one exemplary embodiment, referring to FIG. 3, ESC or iPSCs are cultured on regular tissue culture plastic for 8 days. During that time, the cells are given media as outlined in FIG. 3. Then, the cells are collected, pelleted and cultured in non-adherent U wells for 2 days. Then on Day 11, or Days 12, 13 or 14, the cells are transferred to perfusable chip with an underlying substrate and FSS is applied. Note, the cells may be either embedded in the ECM or sitting on top of it. Also, note that the method works if the embedding day is in the range from Day 11-14 (for vascularized glomeruli+ robust vasculature to form) or Day 15-18 (for vasculature largely without the vascularized glomerulus).

Certain further embodiments relate to a vascularized renal tissue construct or organoid produced by the methods described herein.

Specifically, the vascularized renal tissue construct or organoid comprises at least a single organoid that is vascularized through the help of FSS using the methods described herein. The renal tissue construct could include multiple organoids embedded in ECM whose vasculature is lumenally connected to the vascular patterns or channels which are made using printing. The vascularized renal tissue construct or organoid produced by the methods described herein may have use in glomerular disease modeling (e.g., FSGS, or study damage to glomeruli using drugs such as doxorubicin), tubular disease modeling (e.g., PKD), vascular disease modeling (e.g., hyperglycemia or the effects of fibrosis), drug toxicity studies (e.g., study the mechanistic safety of any antibody, small molecule, RNA, or other therapy on chip and determine specifically which compartment of the kidney is effected and how much it is damaged and where drugs are trafficked), drug screening applications (produce tissues with monogenic diseases and then study gene therapy solutions on chip, screen for drugs that limit fibrosis on chip), living dialysis devices, and as kidney tissue for replacement of kidneys (regenerative medicine).

In certain embodiments, towards living dialysis devices, the vascularized renal constructs may be used to introduce whole blood in the printed pattern of the renal tissue construct to determine if the enhanced organoids are capable of filtering blood and creating a filtrate which would be necessary for building renal assist devices with living cellular components. Towards regenerative medicine applications, we want to build constructs which hook up the organoid to both afferent and efferent printed blood vessels nested in a collecting duct system for collecting urine. The respective parts of the vascularized organoid will hook into these connections and create working nephrons in vitro that could be matured and implanted to replace renal function.

Surprisingly, culturing renal organoids under fluidic shear stress has the potential to unlock new opportunities for glomerular disease modeling, podocyte/vascular maturation, and development of a glomerular filtration barrier in vitro.

Culturing renal organoids under fluidic shear stress also has the potential to unlock new opportunities in regenerative medicine and dialysis, given the potential to demonstrate a filtration barrier in vitro.

Specifically, in one embodiment, the pretubular aggregates (PA) are prepared according to the methods described in the Examples section below.

FIG. 5A shows the organoids produced by the methods described herein as compared to the prior art organoids in FIG. 5B and human adult kidney tissue in FIG. 5C. Clearly, the presently produced organoids closely resemble the adult kidney tissue, including a robust vasculature.

Figure 4:
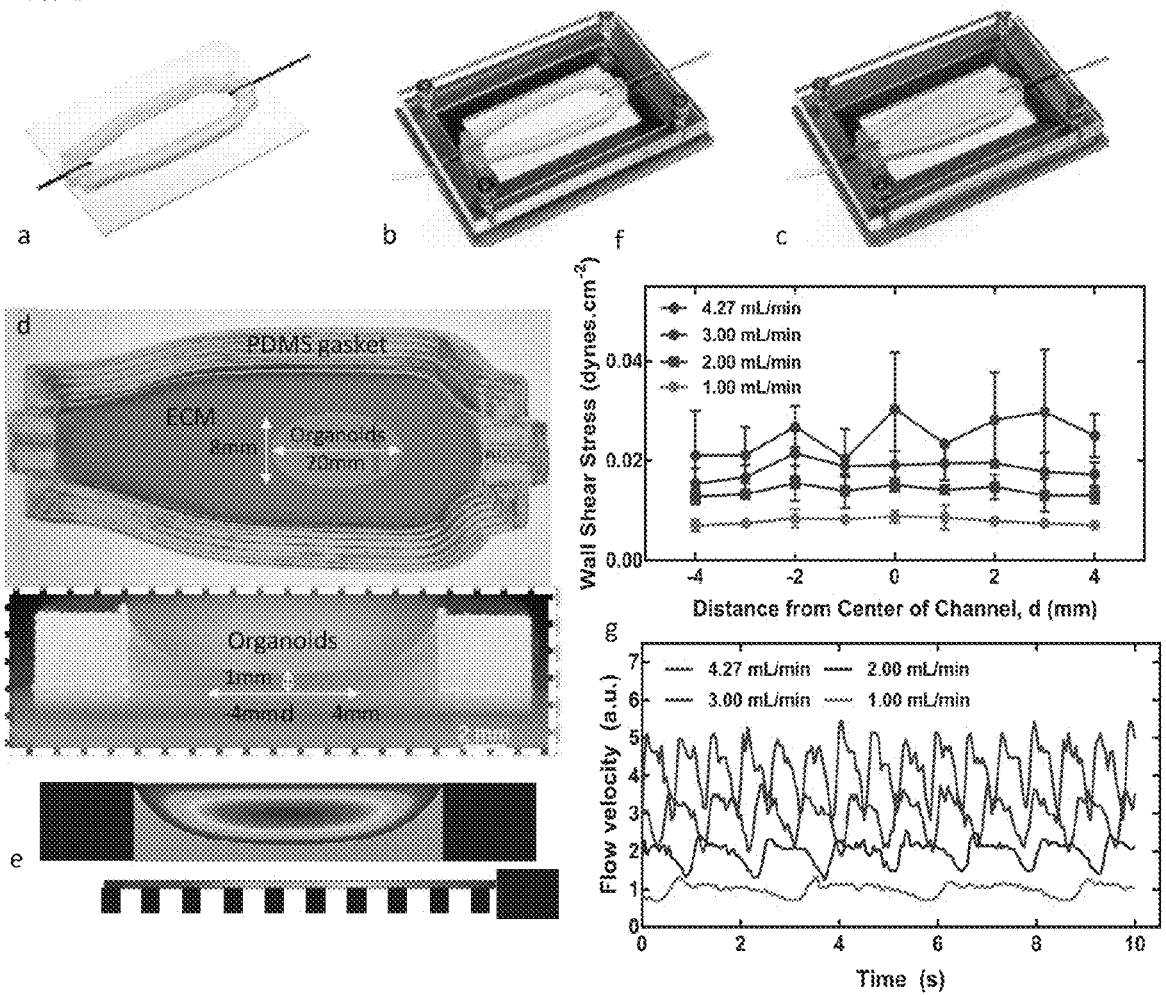
FIG. 4 depicts kidney organoid chip design and fabrication: (a) Customized polydimethylsiloxane (PDMS) gasket printed on a glass substrate with perfusion pins inserted on the left (inlet) and right (outlet) for media flow; (b) The printed gasket/substrate/pin assembly is housed within the kidney organoid chip, engineered ECM layer (gelbrin) is added on top of the glass substrate and cured, developing organoids (Days 11-14) are placed on top of the ECM layer and surrounded by steel casing and acrylic lid. Finally, external perfusion tubing is connected to the pins; (c) Media is perfused through the chip, which is placed in the incubator where media flows in a closed loop circuit using a peristaltic pump; (d) Photograph of the chip in top-down and cross-sectional views highlighting the location of ECM (pink) and organoids; (e) Simulated cross-sectional flow profile (from COMSOL) at a volumetric flow rate of 1 mL/min; (f) Shear stress calculated from experimental bead-flow measurements made adjacent to the gel surface at different positions across the channel. Error bars represent the 95% confidence interval of the velocity gradient derived from linear regression analysis; (g) Measurements of velocity as a function of time, recorded at the center of the channel, 80 μm above the gel surface, demonstrating pulsatile nature of our perfusion process at higher flow rates.

The described 3D printed fluidic chips have a simplistic design that enables organoids to be subjected to superfusion (flow over their top surface), and, hence, controlled wall shear, or FSS (FIGS. 3 and 4(a-g)).

In certain embodiments, a chip may be prepared by using a silicone-based ink to 3D print customized perfusion gaskets, in which developing kidney organoids may be placed. Any suitable silicone-based ink may be used. In certain embodiments, the ink may be composed of a two-part silicone elastomer (SE 1700, DOW Chemical) with a 10:1 base to catalyst (by weight) that was homogenized using a centrifugal mixer for 2 min (2000 rpm, AE-310, Thinky Corp, Japan).

In certain embodiments, the chips may be fabricated using a custom-designed, multimaterial 3D bioprinter equipped with four independently addressable printheads mounted onto a 3-axis, motion-controlled gantry with a build volume of 725 mm×650 mm×125 mm (AGB 10000, Aerotech Inc., Pittsburgh, PA USA). The ink may be extruded through deposition nozzles by applying air pressure (e.g., 800 Ultra dispensing system, EFD Inc., East Providence, RI, USA), ranging from e.g., 10-90 psi, corresponding to print speeds between, e.g., 1 mm/s and 5 cm/s.

After printing, the perfusion chip can be cured at 80° C. in an oven for >1 h, stored at room temperature, and autoclaved prior to use.

In certain embodiments, the gasket includes an organoid chamber, e.g., 15 mm wide by 3.6 mm high and 60 mm long.

In certain embodiments, the organoids, between 4 and 25 per chip, can be placed centrally in an area of 8 mm wide by 3.6 mm high and 20 mm long as shown in FIG. 4(d).

In certain additional embodiments, the method of producing a vascularize renal tissue constructs or organoids may further comprise embedding the developing organoid in the tissue construct. The embedding the developing organoid in the tissue construct can include depositing one or more sacrificial filaments on the substrate to form a vascular pattern, each of the sacrificial filaments comprising a fugitive ink; depositing or printing the developing organoid within the vascular pattern; at least partially surrounding the vascular pattern and/or the developing organoid with an extracellular matrix composition; and removing the fugitive ink, thereby forming the tissue construct comprising the developing organoid embedded therein.

Figure 7:
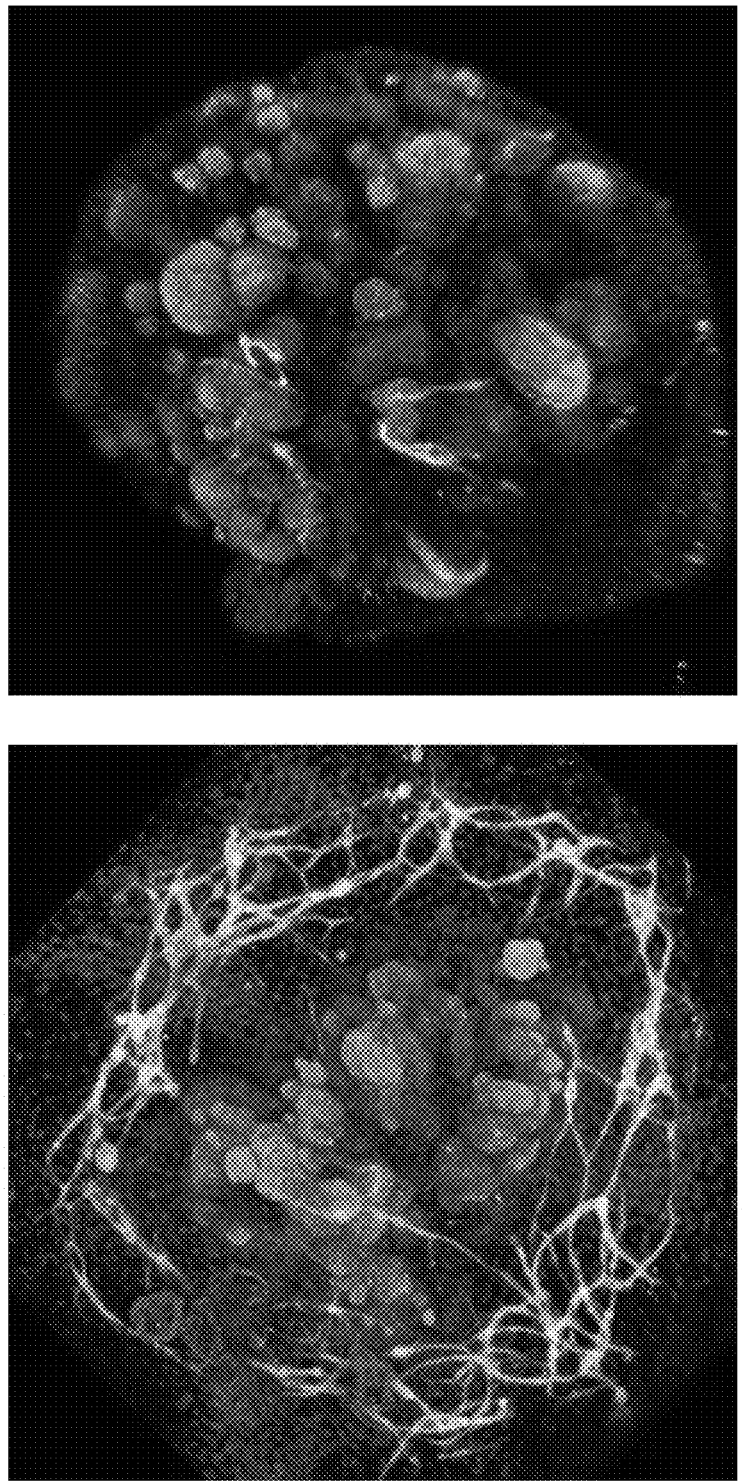
FIG. 7 shows enhanced peripheral vascular network formation in non-adherent versus adherent underlying ECMs, scale bars=100 μm.

It was surprisingly discovered that the developing kidney organoids are adherent and become partially embedded in a ~1 mm thick layer of gelatin-fibrin (gelbrin) ECM, which coats the bottom of the printed chip, permitting the application of FSS (FIG. 22). Interestingly, this adherent matrix leads to enhanced peripheral expression of vascular markers PECAM1 and its precursor, MCAM within 1 week in static conditions, compared to non-adherent matrices (e.g., glass, plastic, fibrin±collagen type 1) (FIG. 7). Several media compositions and co-culture with primary human endothelia+/−fibroblasts were tested; however, many of them inhibited nephron formation or failed to enhance vascularization. A low FBS concentration at 1.5%, generally used in endothelial culture media, permitted nephrogenesis and some vascular network formation in developing kidney organoids under static conditions.

In certain embodiments, to determine the effects of FSS, developing organoids may be placed on the gelbrin ECM layer and superfused overnight with basal organoid media in a closed-loop system at a minimum flow rate of 0.04 mL/min (low FSS, ~0.0001 dyn/cm$^2$). In certain embodiments, the media may be supplemented with 1.5% FBS. Organoids may then be subjected to varied flow rates (0.04-4.27 mL/min), while continuing the published differentiation protocol (FIG. 3 and FIG. 4) (Morizane, et al. "Generation of nephron progenitor cells and kidney organoids from human pluripotent stem cells," Nat Protoc 12, 195-207 (2017); and Morizane, R. et al., "Nephron organoids derived from human pluripotent stem cells model kidney development and injury," Nature biotechnology, doi: 10.1038/nbt.3392 (2015)). The high flow rate range (high FSS, e.g., 0.008-0.035 dyn/cm$^2$ correlating to flow rates of 1-4.27 mL/min) can enhance MCAM$^+$ PECAM1$^+$ vascular networks after 10 days of perfusion (Day 21 total), with nephrons forming over time (see, e.g., FIG. 6).

In certain embodiments, to quantify vascularization, a publicly available Angiotool plugin to ImageJ may be used to evaluate whole mount organoid images (Zudaire, E., Gambardella, L., Kurcz, C. & Vermeren, S. A Computational Tool for Quantitative Analysis of Vascular Networks. PLOS ONE 6, e27385, doi:10.1371/journal.pone.0027385 (2011)).

Figure 8:
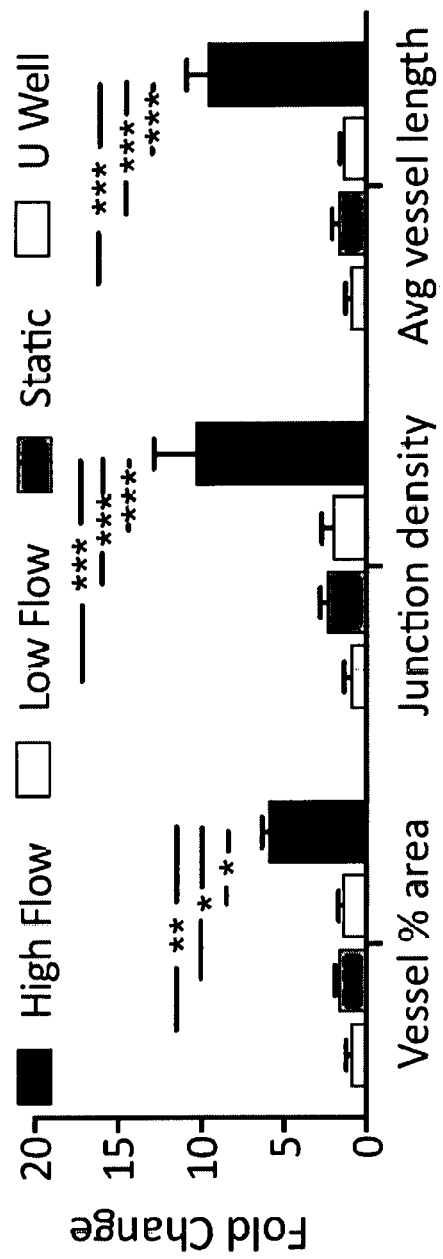
FIG. 8 shows angiotool output, which quantifies the abundance and character of vasculature in the various culture conditions, reported as a fold change relative to the U well condition: 6-11 biologic replicates were used per condition in each of 4 independent experiments, using both iPSC- and hESC-derived organoids where the whole organoid represents one replicate.
Figure 9:
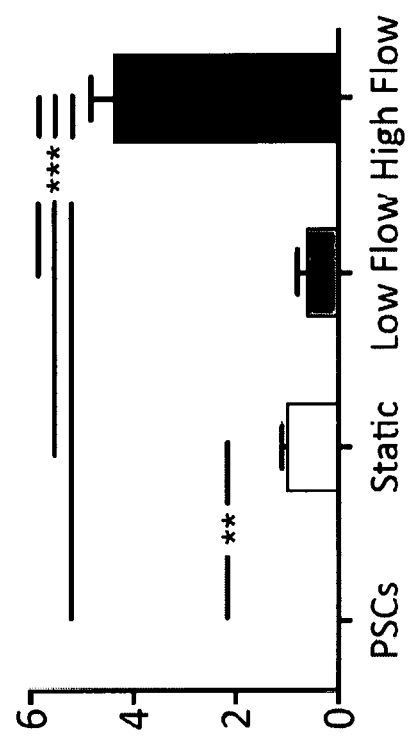
FIG. 9 shows results of qPCR depicting increased PECAM1 expression under high flow conditions, *p<0.05, p<0.01, *p<0.001.
Figure 23:
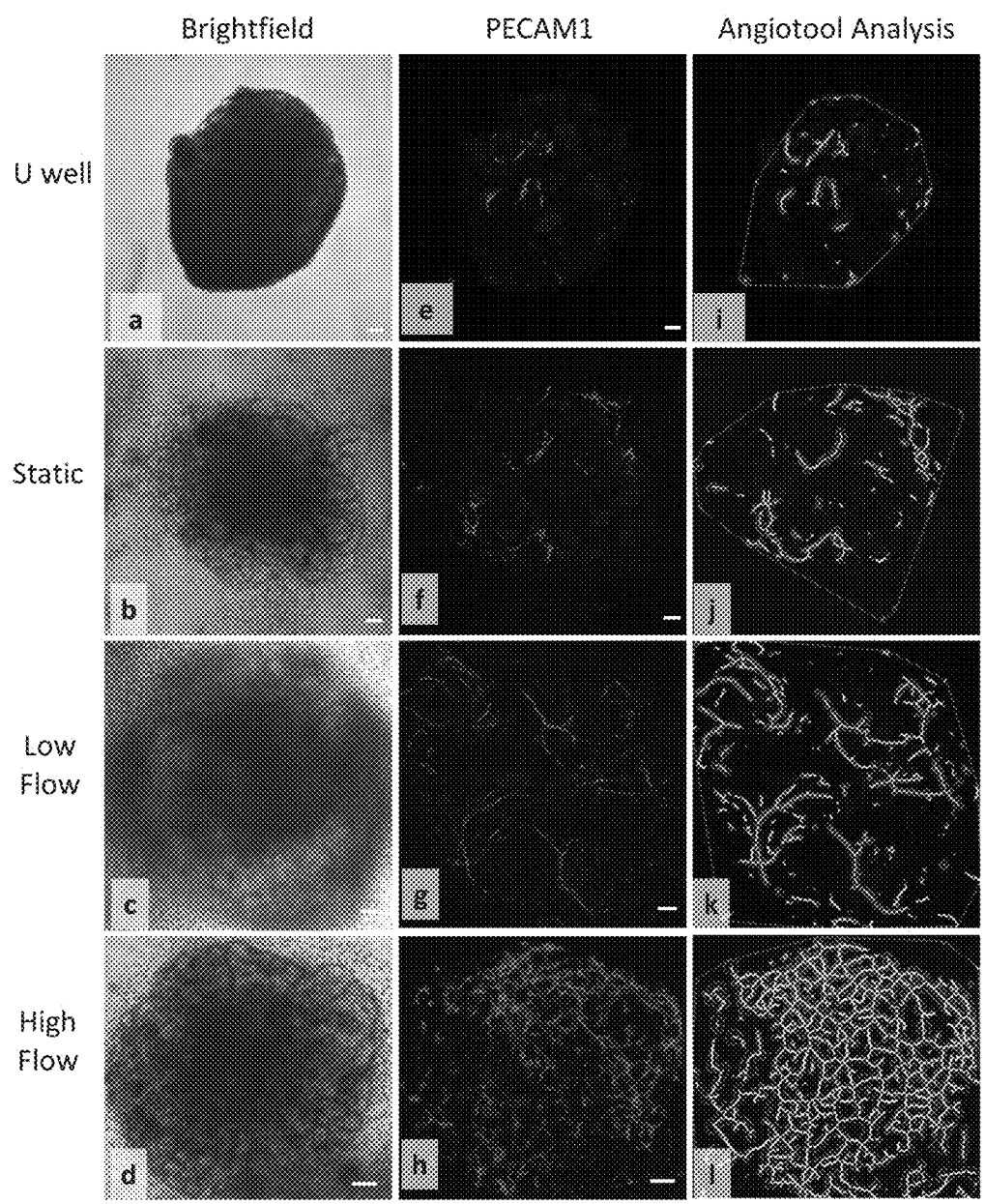
FIG. 23 shows quantification of fluid flow enhanced vascularization in renal organoids: (a-d) Brightfield images of organoids in non-adherent U well conditions, static on ECM, low flow, and high flow conditions where (e-h) are corresponding max intensity projections of z stacks of PECAM1 staining (red) taken whole mount, scale bars=100 µm; and (i-l) Angiotool analysis of the corresponding projections where the thick white lines represent vascular paths, the blue dots represent vascular junction points, the yellow lines highlight the outer edges of the vascular structures counted, and the thin white line around the outside circumscribes the entire area over which the organoid was analyzed for vascular structures, confirmed by Brightfield images. PECAM1: CD31.

In certain embodiments, the high FSS condition may induce PECAM1$^+$ vascular networks whose vessel % area is 5-fold higher than in the low FSS conditions (FIG. 8 and FIG. 23). Similarly, under high FSS, the resultant PECAM1$^+$ networks may exhibit a 10-fold increase in junctional density (i.e., branch points per unit area) and average vessel length (i.e. inter-junctional distance) compared to static and low FSS controls (FIG. 9). Concurrently, PECAM1 transcripts are 5-fold upregulated (FIG. 9). Notably, high flow samples subject to either 0.2 mL or 1 mL of total media per organoid in a closed-loop system lacked a statistically significant difference in vasculature (not shown), reflecting that variable nutrient supply in this range had no discernible effect on vascularization. Hence, it was concluded that, surprisingly, high FSS is the most important environmental factor tested in facilitating vascularization of kidney organoids in vitro.

Figure 10:
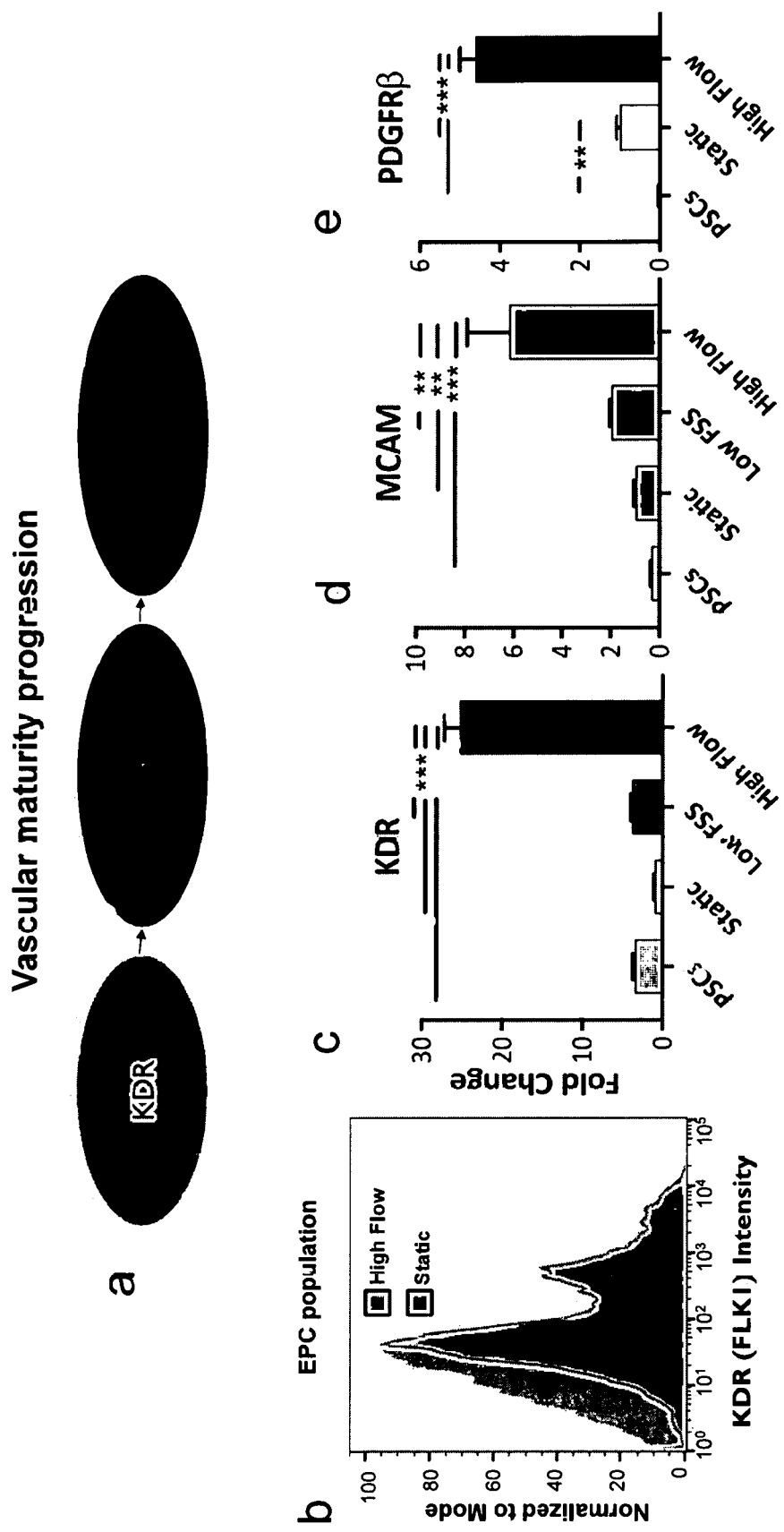
FIG. 10 demonstrates that culture under flow enhances the vascular potential of kidney organoids. (a) Diagram of endothelial maturation in developing kidneys, from progenitor cells to sustained terminal marker expression. (b) Flow cytometry of dissociated whole organoids depicting ~3-fold expansion of the endothelial progenitor cell (EPC) population in response to high flow, compared to static conditions on chip at Day 21. (c,d) qPCR of endothelial cell markers in developing organoids showing their upregulation following high flow conditions at Day 21. (e) A key stromal marker that is upregulated in high flow conditions, possibly due to mural cells associating with enhanced vasculature as shown in FIG. 11.
Figure 11:
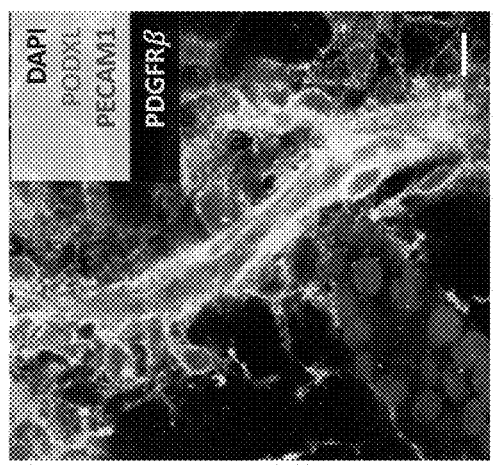
FIG. 11 shows vasculature wrapping a tubule with clear recruitment of stabilizing pericytes (PDGFRbeta cells), scale bar=15 μm.
Figure 12:
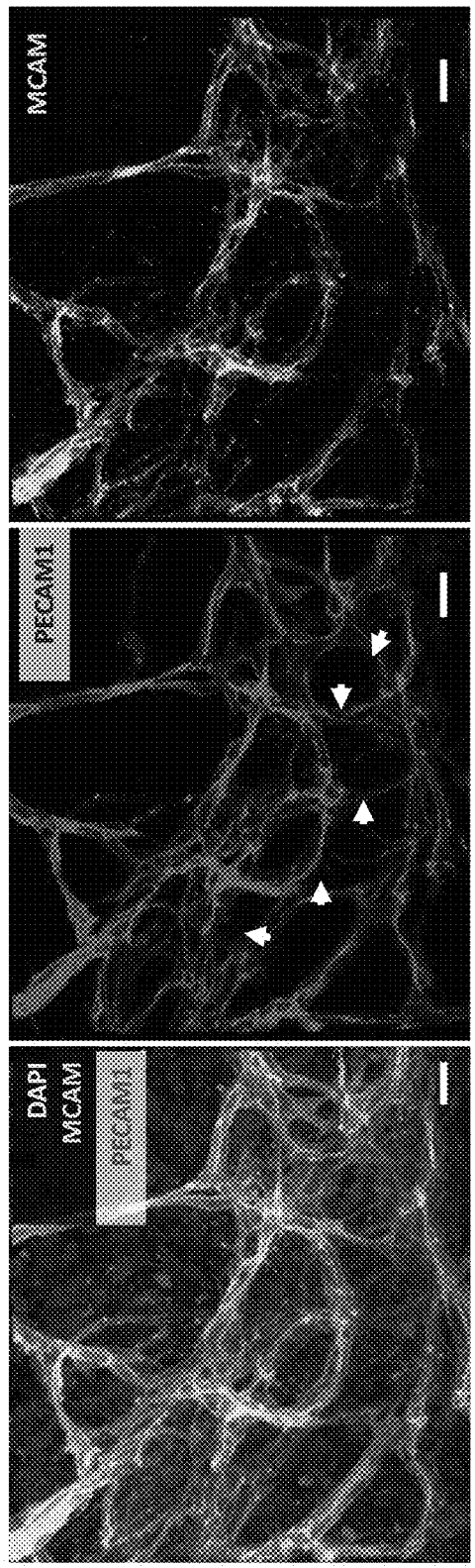
FIG. 12 shows whole mount confocal 3D renderings of vascular markers revealing that some areas of vasculature are best visualized in co-stained samples (left), as opposed to only mature (middle) and intermediate (right) markers, scale bars=30 μm. White arrows highlight areas that are PECAM1+MCAM−, showing the two markers are not always co-expressed.
Figure 24:
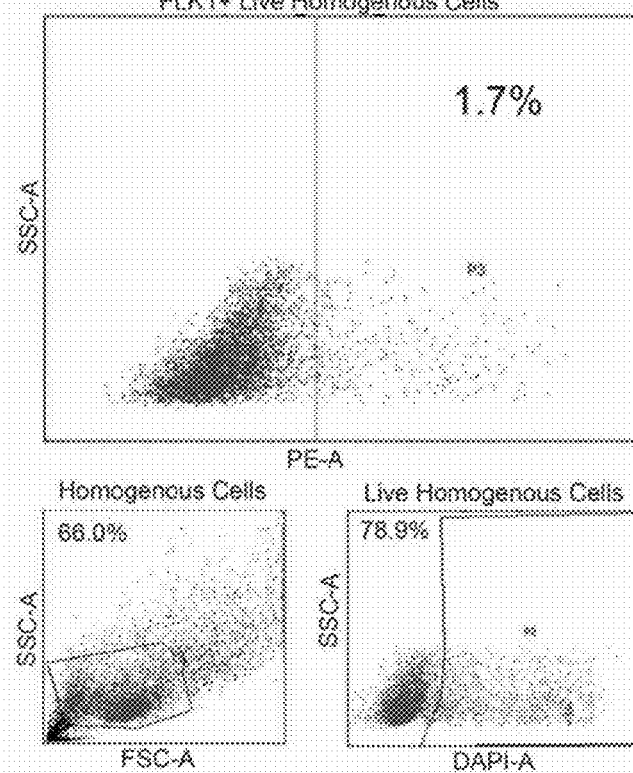
FIG. 24 shows the presence of vascular precursor cells KDR+(FLK1+) at Day 8 of differentiation. Flow cytometry data showing that FLK1+ cells represent 1.7% (a) of the gated cell population (based on homogenous, live cells as shown), in comparison to unstained live cellular controls (b).
Figure 24:
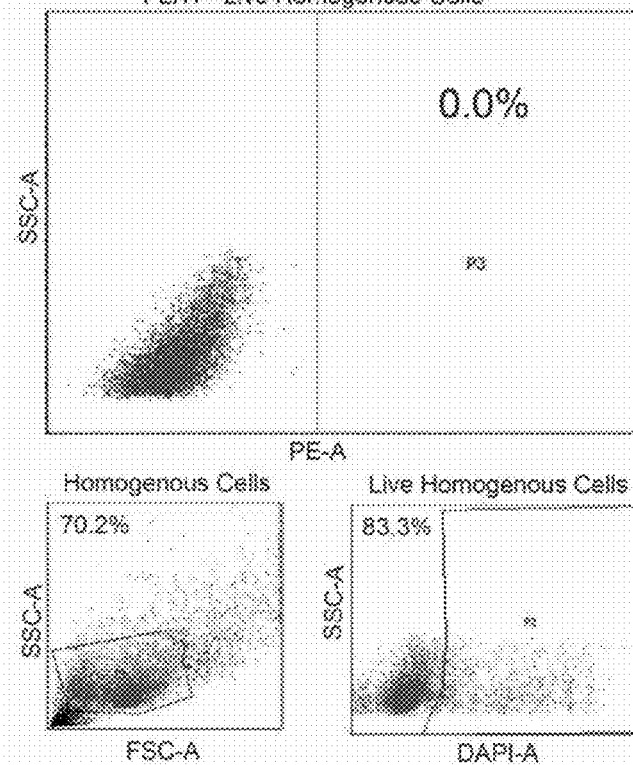

During kidney development, vascular development is believed to occur via a combination of vasculogenesis, the de novo formation of blood vessels through the differentiation and coalescence of endothelial progenitor cells (EPCs), and angiogenesis, the formation of new blood vessels sprouting from pre-existing vessels (Munro, D. A. D., et al., "Cycles of vascular plexus formation within the nephrogenic zone of the developing mouse kidney," Scientific Reports 7, 3273 (2017); and Daniel, E. et al., "Spatiotemporal heterogeneity and patterning of developing renal blood vessels," Angiogenesis, 1-18 (2018)). In the developing mammalian kidney in vivo, fate mapping shows that KDR+(FLK1) cells serve as EPCs to intermediate MCAM+ cells and ultimately PECAM1$^+$ mature endothelia (FIG. 10a) (Robert, B., et al., "Direct visualization of renal vascular morphogenesis in Flk1 heterozygous mutant mice," American Journal of Physiology—Renal Physiology 275, F164-F172 (1998); and McMahon, A. P., "Development of the Mammalian Kidney," Curr. Top. Dev. Biol. 117, 31-64 (2016)). Akin to metanephric mesenchyme (MM) in vivo (Abrahamson, D. R., "Development of kidney glomerular endothelial cells and their role in basement membrane assembly," Organogenesis 5, 275-287 (2009)), KDR$^+$ EPCs may be concurrently induced with SIX2$^+$PAX2$^+$SALL1$^+$ nephron progenitor cells (NPCs) (not shown), constituting 1.7% of MM cells (FIG. 24 (a-b)). High FSS expands KDR$^+$ EPCs to 11.2% of the cells in whole organoids as compared to 4.25% in static culture on chip (FIG. 10(b)). Further, transcripts for KDR and MCAM were upregulated by day 21 after 10 days of high flow (FIG. 10(c,d)), indicating that FSS is a critical environmental cue to expand vascular potential. Transcripts of PDGFR-β are also upregulated (FIG. 10(b)), a marker for pericytes which we find recruited to PECAM1$^+$ vessels in organoids under high FSS (FIG. 11) As the vascular networks evolve on chip, heterogenous expression of vascular precursor and mature markers was found, noting areas that are MCAM$^+$, PECAM1$^+$, or MCAM$^+$ PECAM1$^+$ at day 21 following 10 days of perfusion (FIG. 12). Bound by MCAM and PECAM1 positivity, open circular structures that lack nuclear contents (DAP1$^-$) (FIG. 13(a)), as well as analogous structures between hPSC-derived kidney organoids (FIG. 13(b,c)) and E14.5 embryonic mouse kidneys (FIG. 13(d)), depict lumen formation of variable diameter, suggesting hierarchical vessel formation. Time-lapsed live cell monitoring of the periphery of kidney organoids, stained with Ulex europaeus 1 lectin for vascular endothelium, confirmed luminal perfusion in a subset of endothelia with fluorescent beads (100 nm diameter, performed within minutes of starting bead perfusion) in a single-step method.

To visualize beads inside whole organoids is challenging due to tissue scattering and thus a two-step method may be employed. First, beads may be superfused in the media for 2-3 hours allowing them to build up within the organoid. Next, z-stack confocal images can be taken live at the base of the organoid that is embedded in ECM. The organoids can then fixed, immunostained for PECAM1, and co-registered with fiduciary markers. Notably, beads are present in locations where larger PECAM1$^+$ vessels are found, several hundred micrometers from the superfused bead media surface (FIG. 13(e,f) and FIG. 25(a-c)). Interestingly, branched PECAM1$^+$ networks contain terminal sprout-like structures that lack a PDGFR-β$^+$ cell lining and may represent new vessel growth from existing vessels, suggestive of angiogenesis (FIG. 26(a,b)). Surprisingly, kidney organoids can fuse in as little as 24 h in culture and the vasculature that develops between adjacent organoids on chip is robust and interconnected (FIG. 13(g)). Additionally, the association of PECAM1$^+$ networks with ACTA2$^+$ smooth muscle-like cells suggests the maturation of arterial lineage cells (Scheppke, L., et al., "Notch promotes vascular maturation by inducing integrin-mediated smooth muscle cell adhesion to the endothelial basement membrane," Blood 119, 2149-2158, doi:10.1182/blood-2011-04-348706 (2012)), while the venous marker, EMCN, stains presumptive venous lineage cells (FIG. 26(c,d)). Taken together, surprisingly, it was found that culturing organoids on chip enhances the vascular potential of developing kidney organoids which ultimately form increasingly mature and perfusable vascular networks of varying caliber and lineage.

Figure 14:
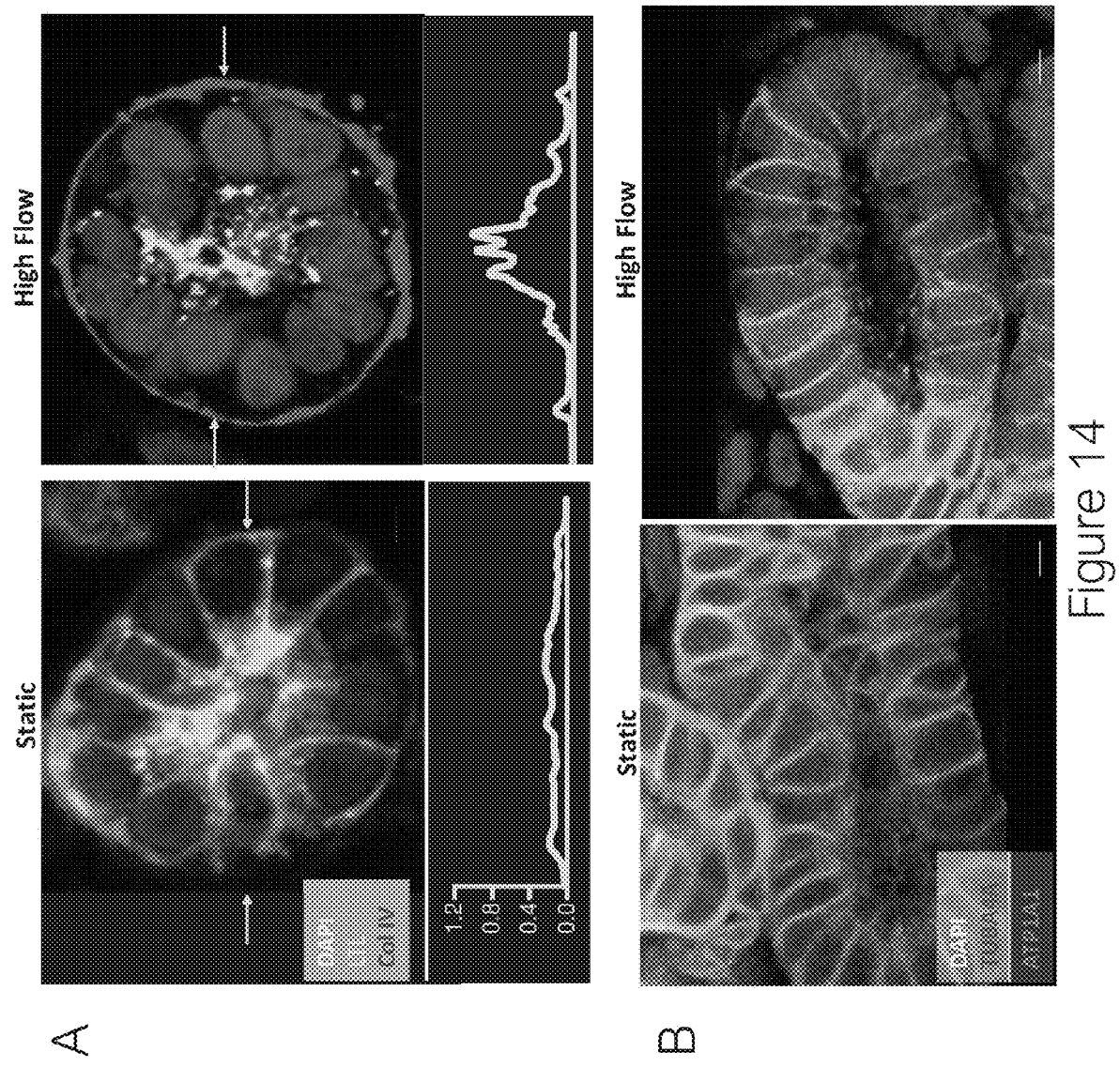
FIG. 14 shows that tubular epithelia mature and undergo morphogenesis to become a polarized, ciliated compartment in contact with vasculature in response to the high flow condition on chip: (A) Tubule cross-sections under static and high flow conditions showing proper basal expression of collagen IV in both cases, and proper apical expression of LTL under high flow at day 21, scale bars=5 μm, the plots in yellow below show the intensity of LTL across a line scan denoted by yellow arrows in the images above; (B) Tubule cross-sections showing apical presence of cilia with higher prevalence (FIG. 27) under high flow versus static conditions on chip and proper basolateral expression of ATP1A1 (Na/K ATPase) on day 21, scale bars=5 μm.
Figure 15:
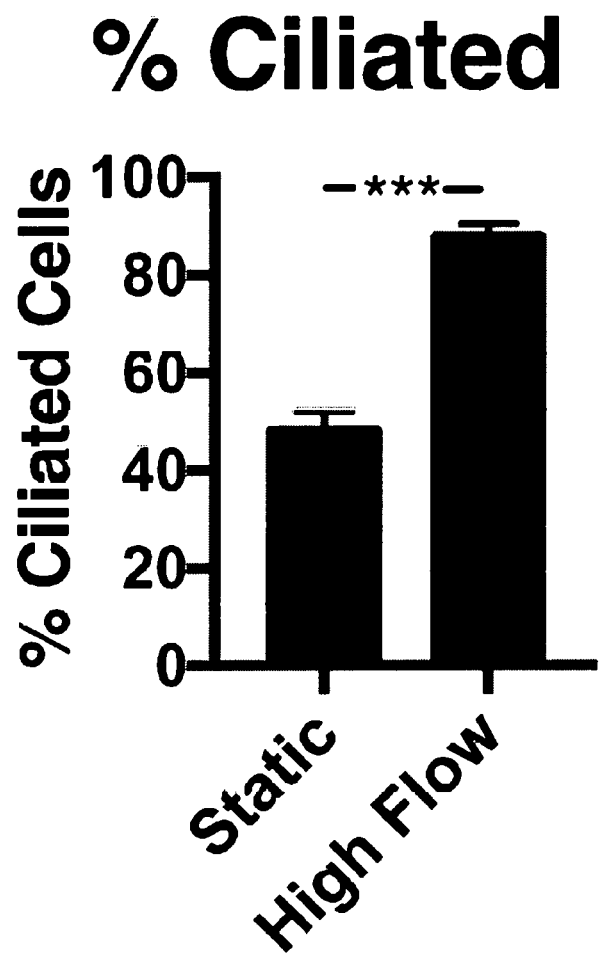
FIG. 15 shows a graph of percent ciliated cells under static and high flow.

Kidney organoids under static conditions manifest limited vasculature which associates with tubular epithelia, demonstrating immature gene expression profiles and morphology analogous to 1$^{st}$ trimester kidney. Following subcapsular transplantation to the mouse kidney, progressive morphogenesis of tubular structures is evident by polarization, formation of a well-developed brush border, and ciliary assembly in vivo (van den Berg, C. W., et al., "Renal Subcapsular Transplantation of PSC-Derived Kidney Organoids Induces Neo-vasculogenesis and Significant Glomerular and Tubular Maturation In Vivo," Stem Cell Reports 10, 751-765 (2018)). The native kidney is a highly fluidic environment with mass fluid transfer occurring between the lumenal and interstitial spaces, as ~98% of the glomerular filtrate is reabsorbed into the interstitium of healthy kidneys. It was hypothesized that similar morphogenesis, as well as maturation of gene expression profiles, may occur in hPSC-derived tubular cells in vitro when subject to high FSS. Surprisingly, the polarity of tubules on chip was shown to be enhanced leading to apical enrichment of the brush border marker, Lotus tetragonolobus lectin (LTL) (FIG. 14(a)) at day 21 after 10 days of high FSS. Similarly, acetylated tubulin demonstrates apical enrichment (FIG. 14(b)) with the presence of primary cilia increasing from 50% to 89% in static to high FSS conditions, respectively (FIG. 15). Consistent with polarization and maturation-associated ciliary assembly, the expression of ciliary proteins (PKD1, PKD2, NPHPI, NPHP6, PKHDI) is upregulated (FIG. 16(a)). Concurrently, expression of tubular epithelial transporters, including AQP1, solute transporters (SLC34A1, ATP1A1, SLC6A19, SLC9A3, SLC2A2), and drug transporters (ABCB1, LRP2) are upregulated when compared to static controls and undifferentiated cells (FIG. 16(b)), which may reflect increased functional potential. The maturation of tubular epithelial cells was evident by the upregulation of adult transcription factors (BNC2, NPAS2, TRPS1) (FIG. 16(c)), which were reported as mature proximal tubule markers by single cell RNA-seq in adult human kidneys (Wu, H., et al., "Comparative analysis of kidney organoid and adult human kidney single cell and single nucleus transcriptomes," bioRxiv, doi:10.1101/232561 (2017)).

Figure 16D:
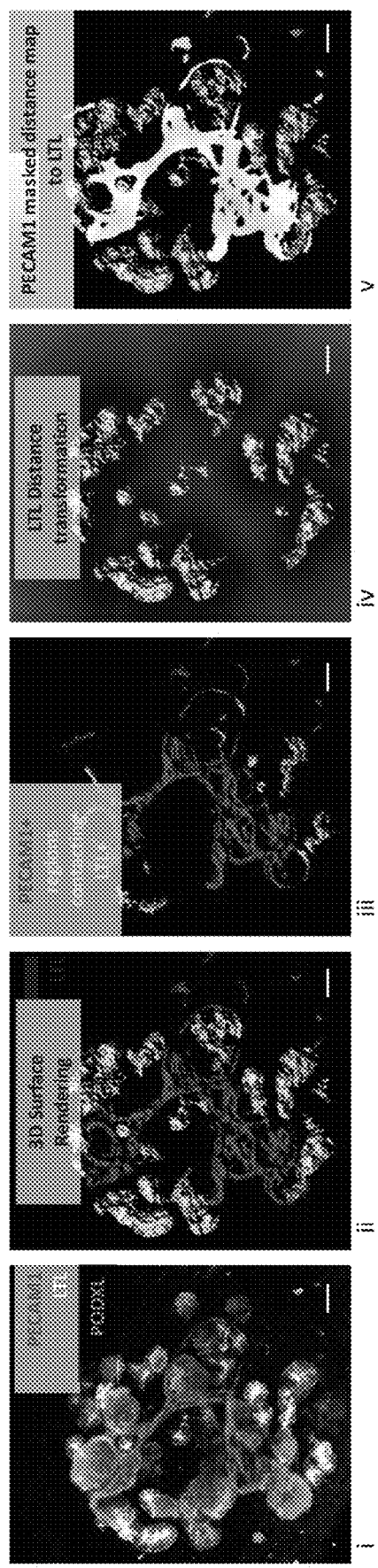
Figure 17:
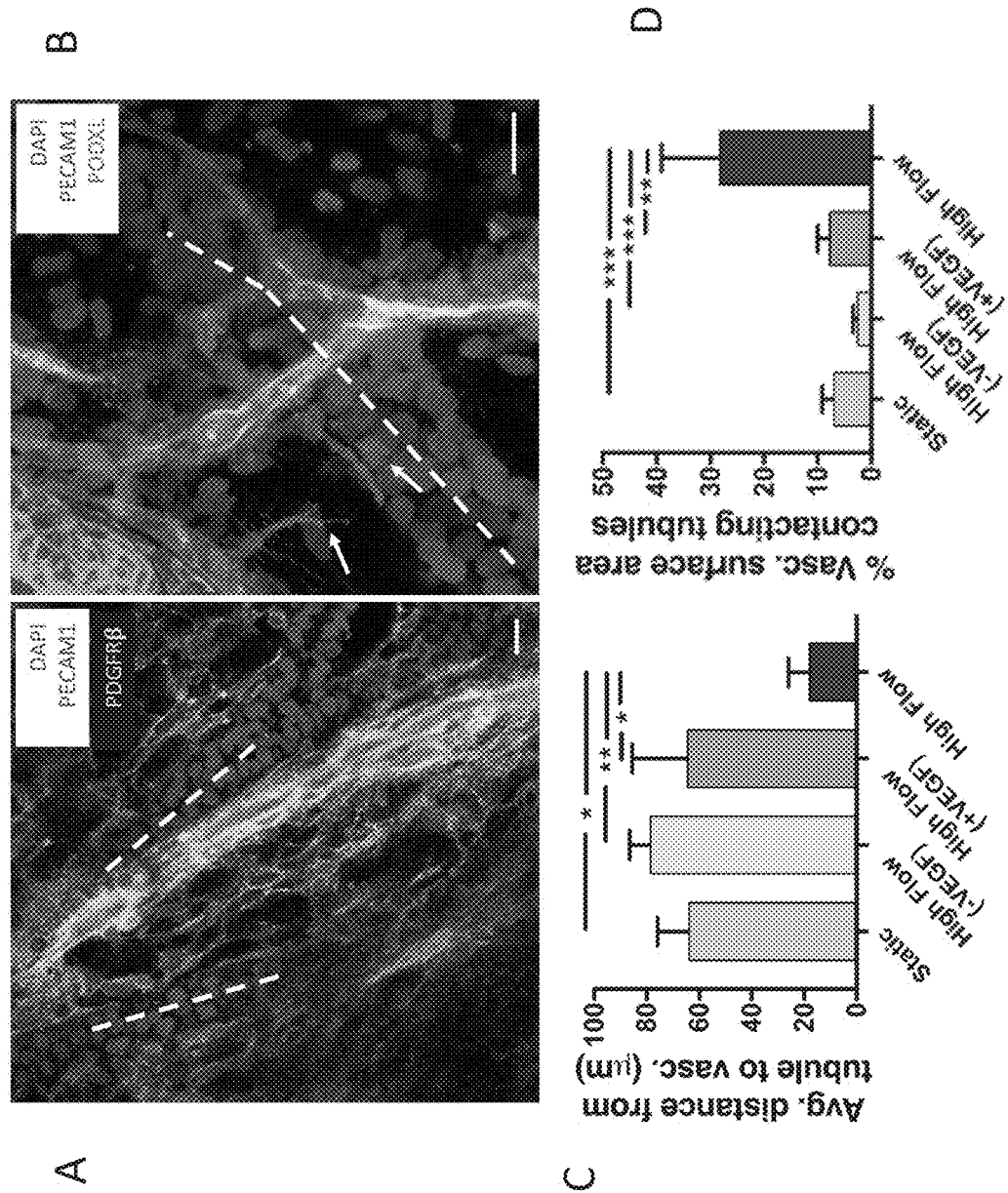
FIG. 17 shows immunostaining showing that PECAM1+ networks associate with tubular structures in both traverse and longitudinal planes in high flow at day 21, scale bars=20 μm (A and B). Whole organoid 3D confocal imaging stacks are used to analyze the association of tubules with vasculature in Imaris 3D surface rendering and distance transformation software to find in (C) that the percent of vasculature surface area overlapping with LTL+ tubules within one voxel is significantly higher under high flow than in static conditions. Further, that tight vasculotubular association can be negated by dosing high amounts of VEGF in the media (C). Similarly, the average distance in 3D between the vasculature and the tubules decreases in the high flow condition (D) but is not statistically significantly different between static and high flow+VEGF conditions. Note the data in (C,D) represents between n=3 and 6 biological whole organoid replicates per condition tested over two independent experiments. DAP1: 4',6-diamidino-2-phenylindole, LTL: lotus tetragonolobus lectin, PECAM1: CD31, PODXL: podocalyxin, TUBA4A: tubulin alpha 4a (also known as acetylated tubulin), AQP1: aquaporin 1, SLC34A1: Na/Phos cotransporter, ATP1A1: Na/K ATPase, ABCB1: MDR1, LRP2: Megalin, BNC2: basonuclin 2, NPAS2: neuronal PAS domain protein 2, TRPS1: transcription repressor GATA binding 1, PKD1: polycystin 1, PKD2: polycystin 2, NPHPI: nephrocystin 1, NPHP6: nephrocystin 6, PKHDI: fibrocystin. *p<0.05, p<0.01, *p<0.001.

Additionally, enhanced PECAM1$^+$ networks under high FSS associate with tubular structures in both transverse and longitudinal orientations (FIG. 16(d) and FIG. 17). The researchers quantified the association between PECAM1$^+$ networks and LTL$^+$ tubules using Imaris surface rendering, distance transformation, and masking tools and reveal that under high flow conditions the percent of vascular surface area in contact with tubules is increased nearly 3 fold in comparison to organoids in static culture (FIG. 17(d)).

Additionally, the mean distance between a tubule and vessels decreased over 3 fold from static to high flow conditions (FIG. 17(a)). Interestingly, addition of 100 ng/mL of VEGF or addition of a VEGF inhibitor to the media during the 10 days of high flow culture decouples these associations and returns values consistent with static culture levels. Thus, maintenance of endogenous VEGF gradients on chip was found to be crucial for vasculotubular interactions, and that epithelial maturation may occur due to interlineage endothelial-epithelial communication during hPSC-derived organoid development. These results surprisingly show that culturing organoids under flow in vitro supports tubular epithelial maturation and morphogenesis in kidney organoids.

In one embodiment, VEGF, or other potent chemoattractants, or gradients of them may be used in tissue constructs to encourage vasculature to pattern in specific directions to link with printed channels or reservoirs that enable or force flow through the nephrons in the organoid. The flow could be of media or of whole blood or blood substitutes with our without growth factors, like VEGF. VEGF could be patterned in the ECM or delivered in the media and could be added continuously in the media or in a specified duration of time, for instance over days 11 through 14 of culture, but any time could be specified. Surprisingly, addition of VEGF causes robust outgrowth of endothelial-like cells, so a temporary outgrowth to enable hook up or angiogenesis with existing or printed vessels could be designed in time and space in the construct. Removal of the exogenously added VEGF would allow the vessel networks to stabilize and couple with the renal structures that would naturally secrete VEGF, like podocytes and tubular cells. Note that while vascular abundance in culture under FSS didn't change with added VEGF in the media or not, adding exogenous VEGF to organoids in static culture did increase their vascular abundance.

Figure 18A:
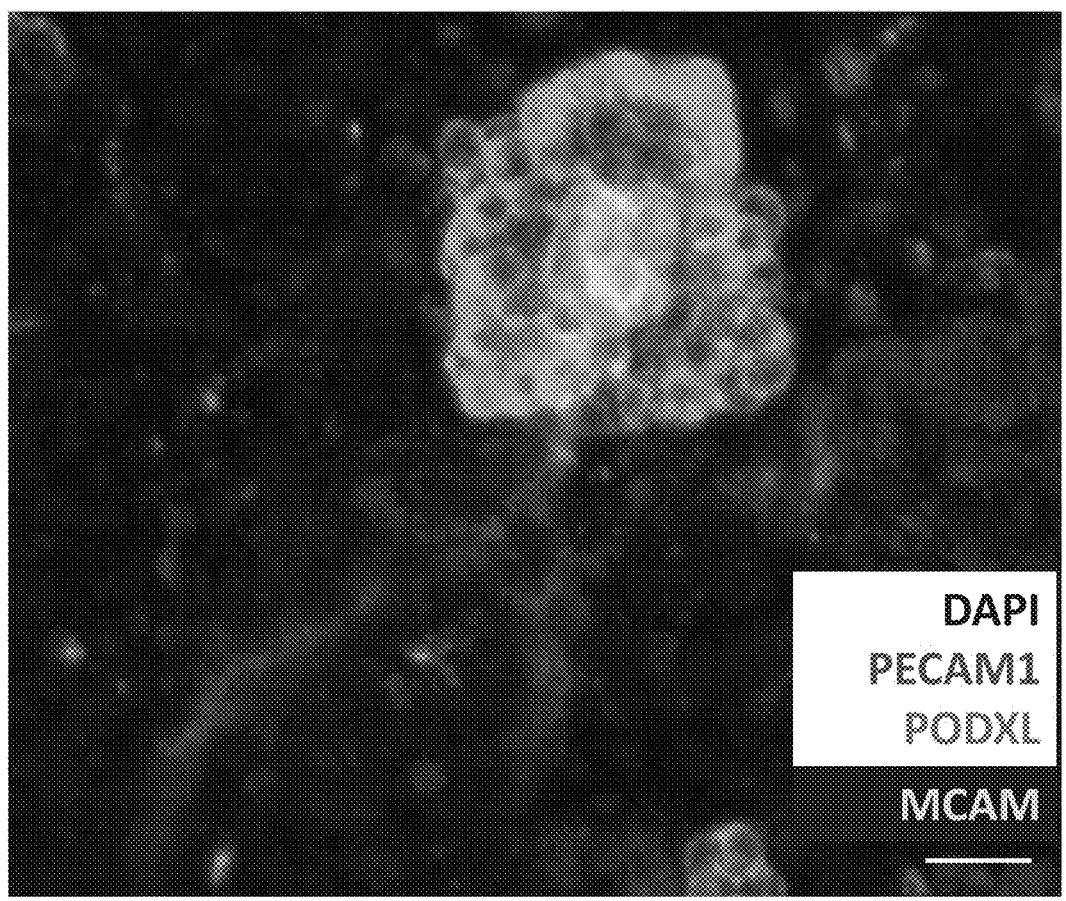
FIG. 18A shows a 3D rendered confocal image of vascular invasion in a PODXL+ cluster showing afferent and efferent vessels, scale bar=40 μm.
Figure 18B:
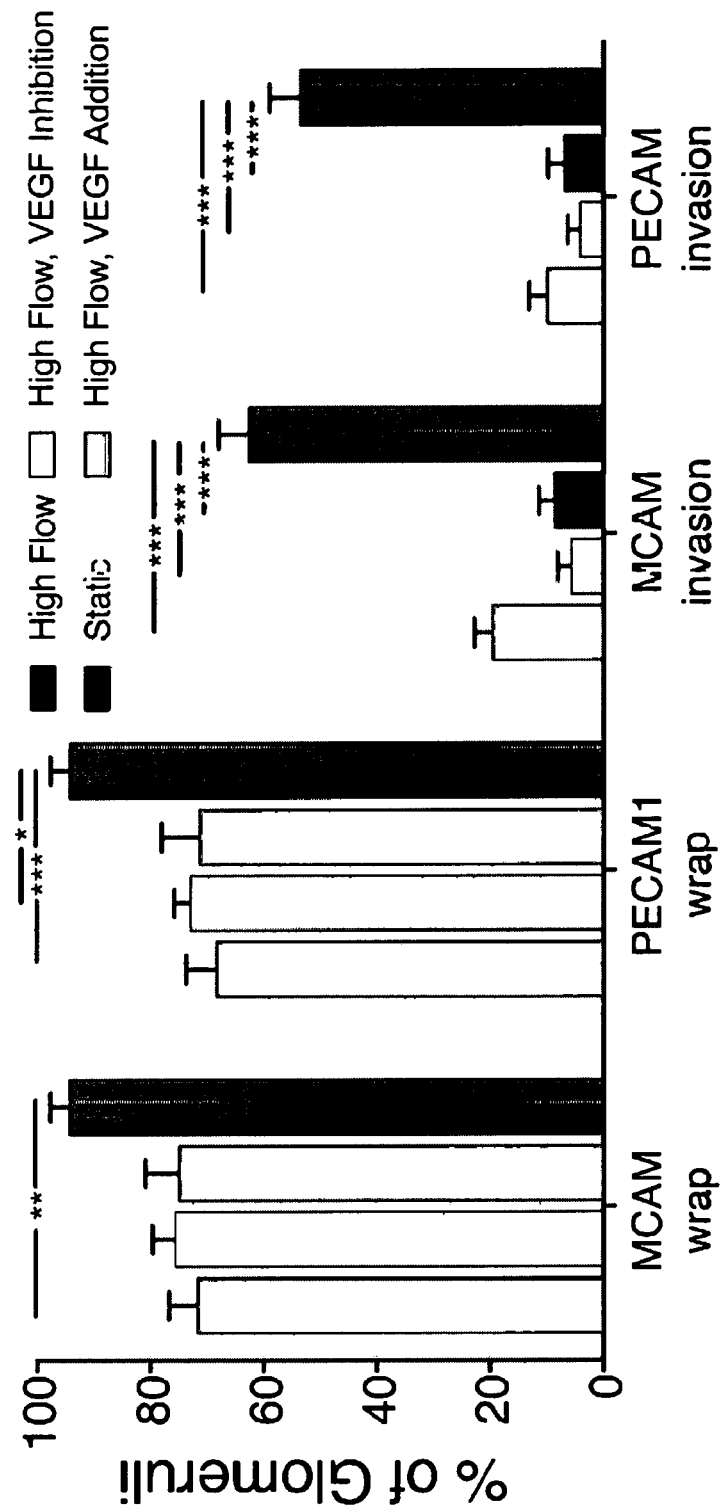
FIG. 18B shows bar graphs showing percent of PODXL+ clusters that exhibit vascular wrapping or invasion in conditions of static and high flow±VEGF addition or inhibition representing n>14 organoids per condition over 4 independent experiments.
Figure 18C:
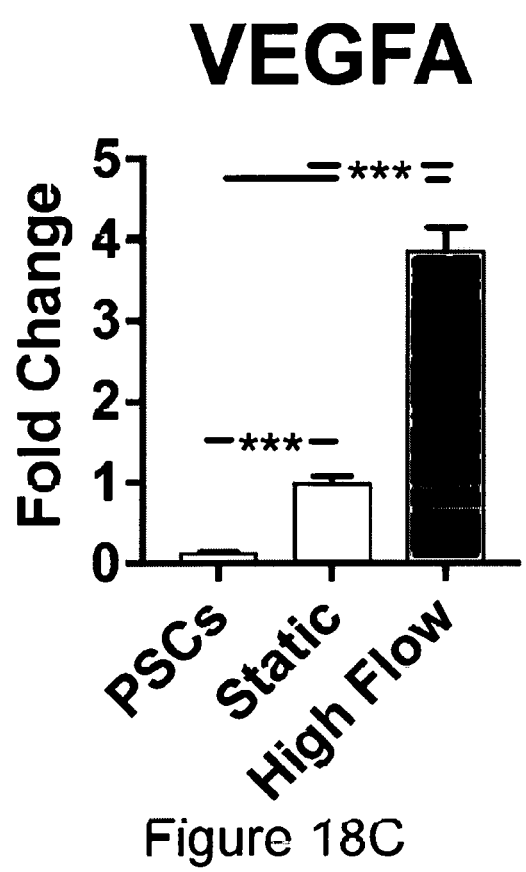
FIG. 18C shows a bar graph showing qPCR of VEGF showing significant upregulation in the high flow condition on chip at day 21.

Glomerular structures of kidney organoids in static culture are largely avascular. Upon animal transplantation, host-derived vascularization of kidney organoids Promotes glomerular vascularization. To determine whether FSS-induced vascularization of organoids in vitro extends to glomerular compartments, $PODXL^+$ podocyte clusters invaded by $MCAM1^+$ $PECAM1^+$ vascular structures were quantified using confocal imaging, in static and high FSS conditions (FIG. 18A and FIG. 18B). Under high FSS, $MCAM^+$ $PECAM1^+$ vascular invasion was significantly increased to greater than 60%, from 10~20% in static controls, while wrapping vascular morphology surrounding $PODXL^+$ clusters is increased to nearly 100% (FIG. 18B), consistent with vascular flow being required for glomerular assembly in animal studies. Given that there is significant upregulation of VEGF-A expression with high FSS (FIG. 18C), organoids cultured under flow can be used to study the role of VEGF in glomerular vascularization in vitro.

Interestingly, both VEGF inhibition (bevacizumab 250 g/mL for 10 days on chip) and VEGF addition (100 ng/mL for 10 days on chip) significantly reduced the incidence of invasion of $PODXL^+$ glomeruli-like compartments by $PECAM1^+MCAM^+$ vascular networks under high FSS (FIG. 18B). As vessel % area is unchanged between endogenous VEGF, VEGF addition, and VEGF inhibition, the difference in glomerular vascularization cannot be attributed to increased abundance of vasculature alone. Meanwhile, the reduced junctional density and increased average vessel length in unperturbed VEGF conditions may be interpreted as vessels growing towards an endogenous VEGF gradient versus more random sporadic growth in the absence of a gradient. Growing with the endogenous VEGF gradient under high flow conditions may allow vessels to reach glomeruli-like compartments in time to invade rather than wrap Bowman's capsule-like structures.

Figure 19:
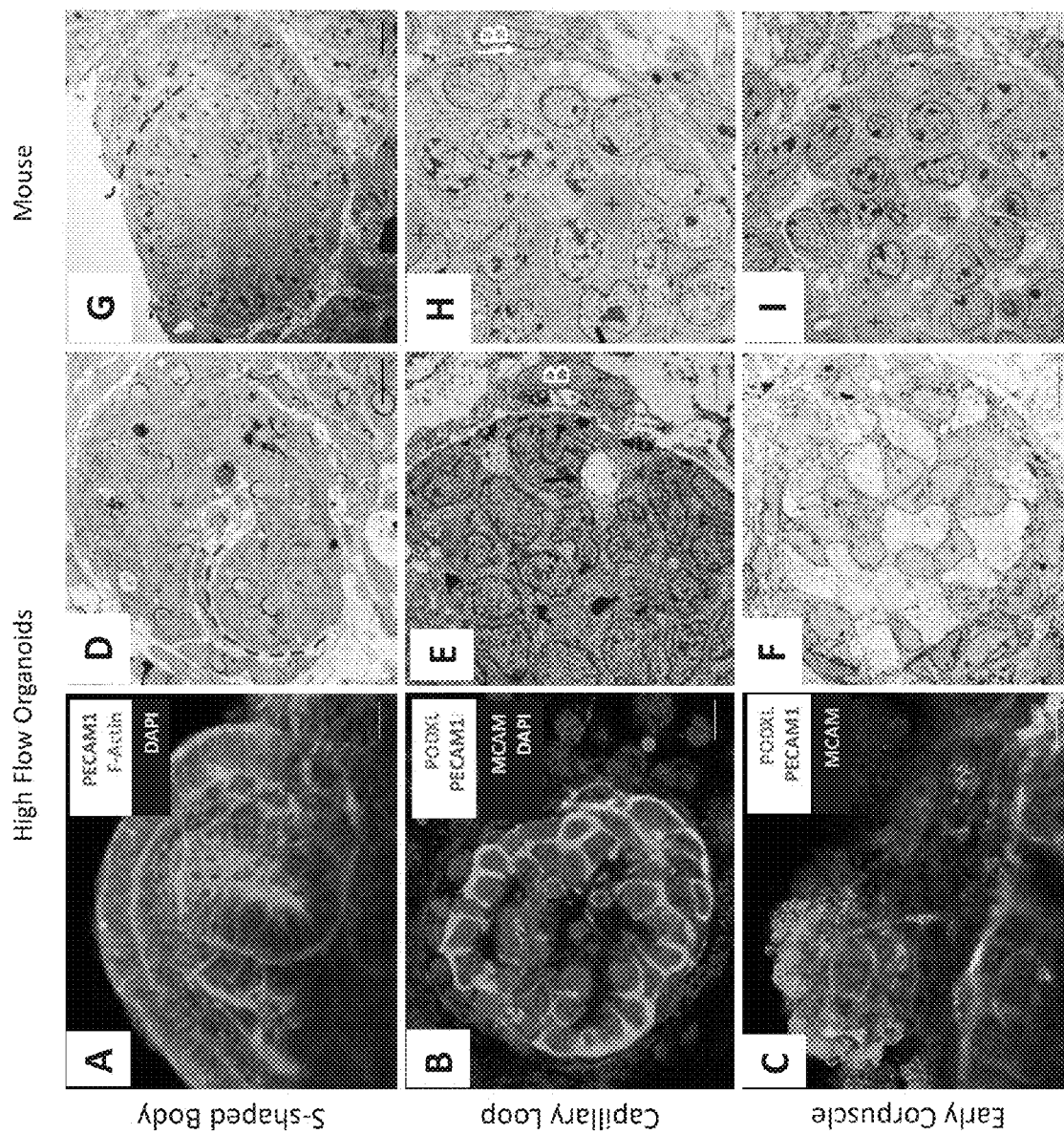
FIG. 19 shows: (A) A 3D rendered confocal image of capillary invasion in an S-shaped body in a vascularized organoid, scale bar=10 μm; (B) Single confocal z-slice showing capillary invasion with PECAM1+MCAM+ cell (white arrow) and MCAM+ vascular precursors (CD146+ cells), scale bar=10 μm; (C) MCAM+PECAM1+ glomerular tuft-like formation shown as a single z-slice from confocal, scale bar=10 μm; (D-F) TEM images of structures correlating with the IF images in kidney organoids at Day 21, scale bars for (D,E)=4 μm and (F)=10 μm; Corresponding stages (G-I) in E14.5 mouse kidneys are shown where red dashed lines depict clefts, white arrows denote capillary invasion, B=Bowman's capsule-like structure, and red plus signs denote RBCs, scale bars for (G,H)=8 μm and (I)=50 μm.
Figure 20:
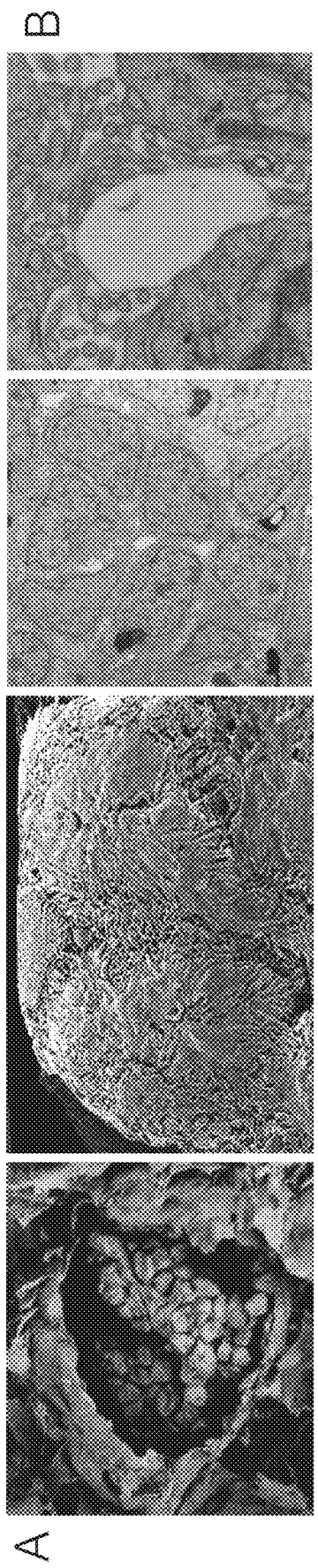
FIG. 20 depicts: (A) TEM images of a glomerular-like structure under high flow on day 21 showing a parietal membrane enclosing a visceral cluster of cells (left), which manifest interdigitating cytoplasmic projections extending across and into the plane of field on higher magnification (right), scale bars=10 µm (left) and 1 µm (right); and (B) TEM images of a glomerulus-like compartment under high flow on day 21 (left) in which higher magnification shows podocyte foot process abutting a glomerular tuft-like formation (right), scale bars=2 µm (left) and 200 nm (left).
Figure 21:
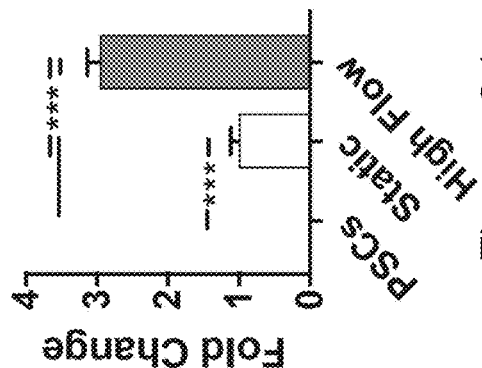
FIG. 21 depicts bar graphs showing results of qPCR depicting significantly upregulated transcripts for podocyte foot process proteins and an adult transcription factor. SSB: S-shaped body, CLS: capillary loop stage, DAP1: 4',6-diamidino-2-phenylindole, MCAM: CD146, PECAM1: CD31, PODXL: podocalyxin, SYNPO: synaptopodin, NPHS1: nephrin, PDGFR-β: platelet derived growth factor receptor beta, VEGFA: vascular endothelial growth factor A, CASZ1: castor zinc finger 1 *p<0.05, p<0.01, *p<0.001.
Figure 21:
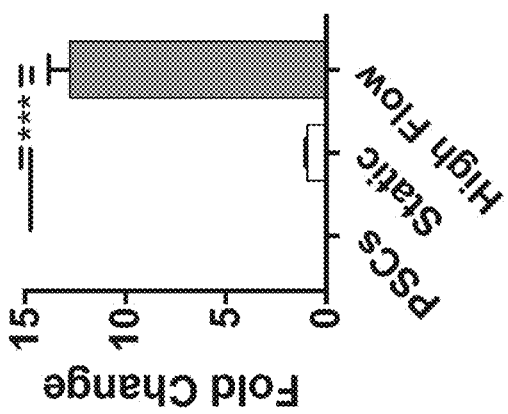
Figure 27:
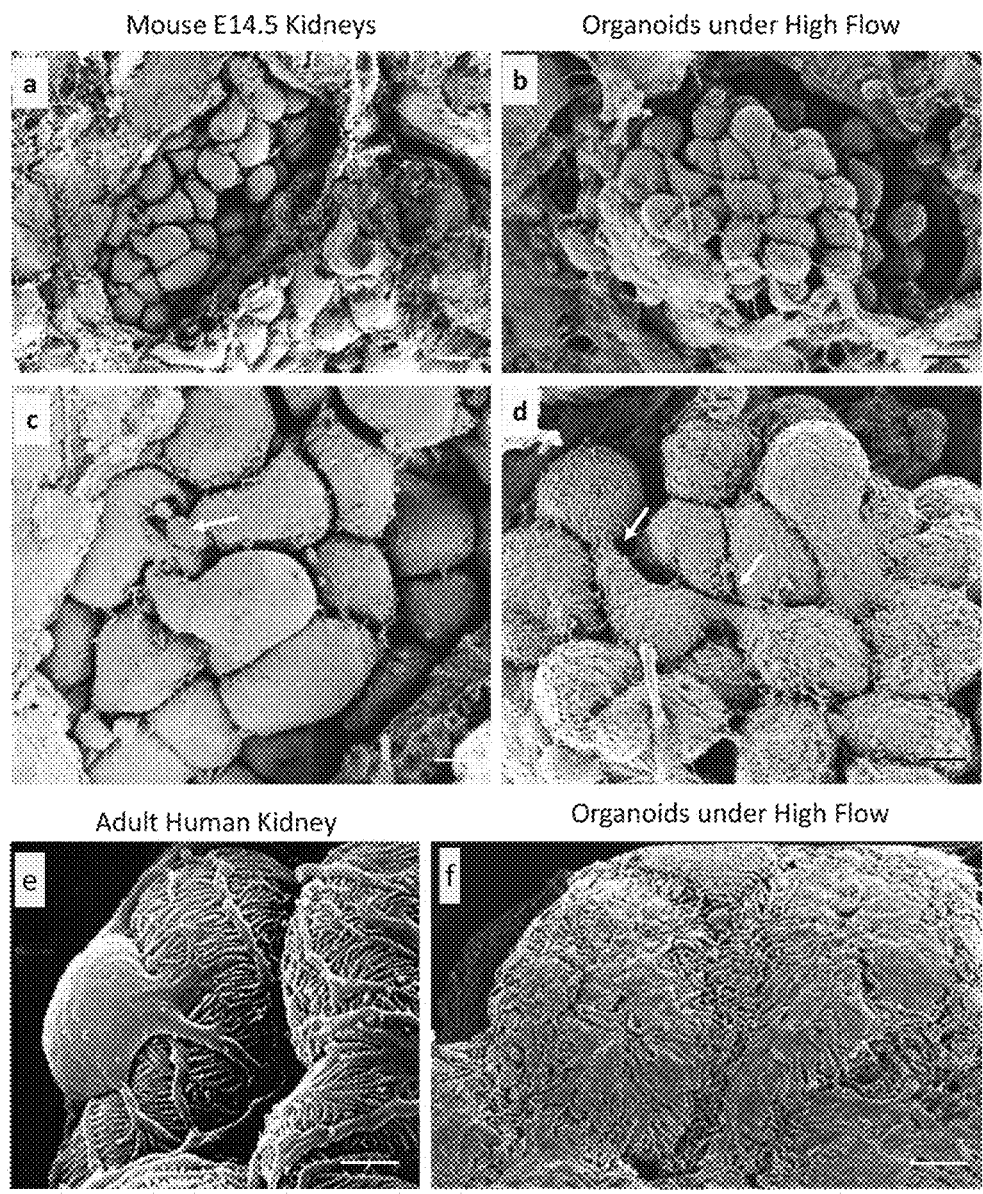
FIG. 27 shows that elongated podocytes with cytoplasmic projections are observed in embryonic mouse kidneys, adult human kidneys, and vascularized kidney organoids cultured under high flow conditions in vitro. SEM images of glomerular regions in a mouse embryonic kidney, day E14.5 (a), and an organoid cultured under high flow conditions (b) show a thin parietal epithelium and nascent podocyte-like cells inside the encasement, scale bars=5 µm. The higher magnification images (c) and (d) show a visceral epithelial layer of podocyte-like cells elongating (white arrows), scale bars=2 µm. (e) Adult human kidney foot processes visualized on SEM, scale bar=200 nm, reprinted with permission (Erlandsen et al., Color Atlas of Histology, Mosby Inc, 1992). (f) An SEM of kidney organoids under high flow where foot processes are interacting between podocytes, scale bar=200 nm.
Figure 28:
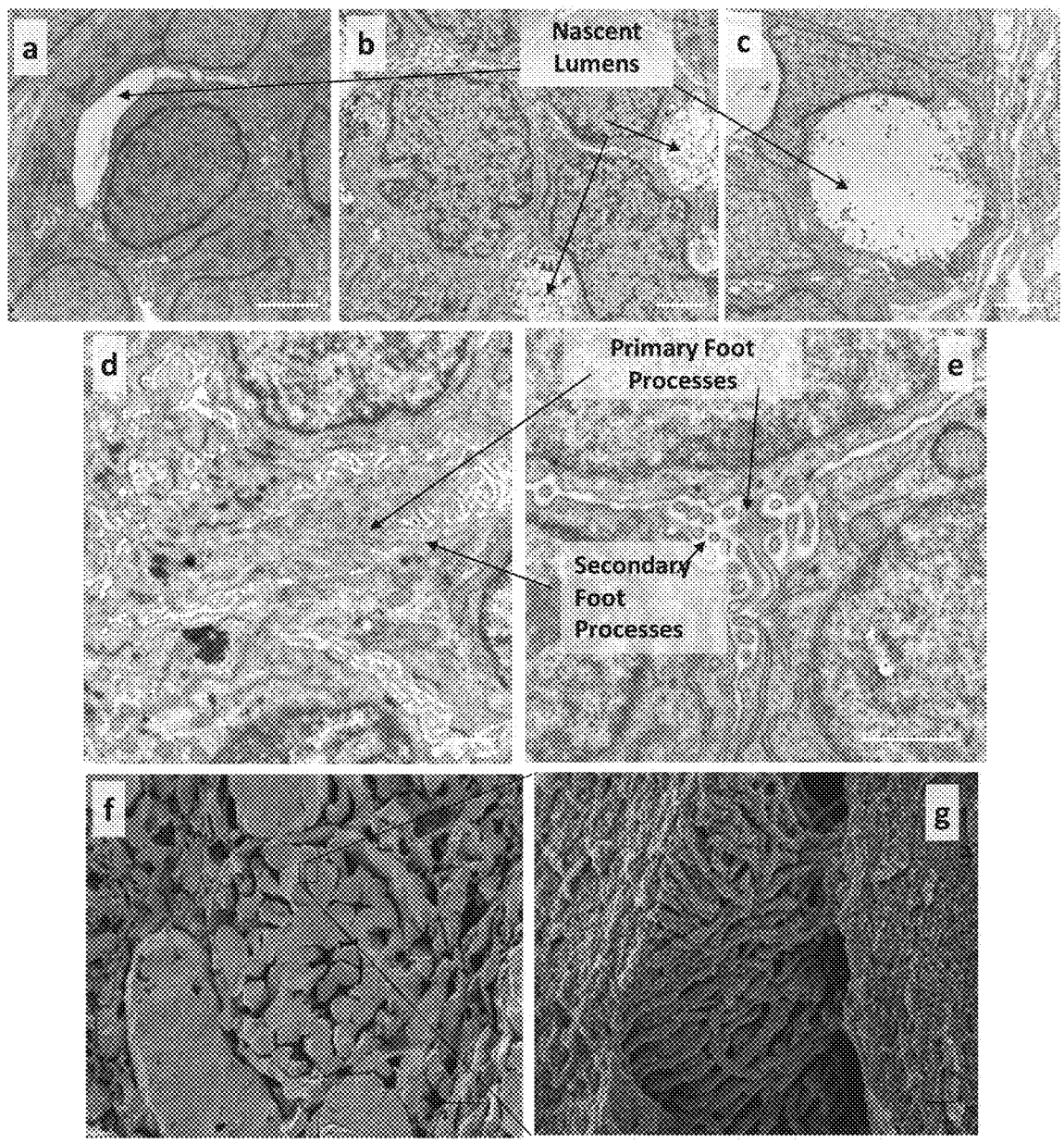
FIG. 28 provides evidence of vascular invasion of glomeruli and podocyte foot processes within vascularized kidney organoids cultured under high flow conditions: (a-c) TEM images of podocyte-like cells under high flow at Day 21 showing several small lumenal openings, scale bars=2 µm, red arrows point to areas of possible endothelial fenestrae formation which manifest as breaks in the thin putative endothelial membrane; (d,e) TEM images of podocytes exhibiting primary and secondary foot process-like structures, scale bars=200 nm; and (f,g) SEM images of a (f) glomerulus-like structure with a parietal membrane encasing clusters of visceral cells, which (g) manifest cytoplasmic projections that interdigitate and align with common directionality, scale bars=10 µm (f) and 200 nm (g).
Figure 29:
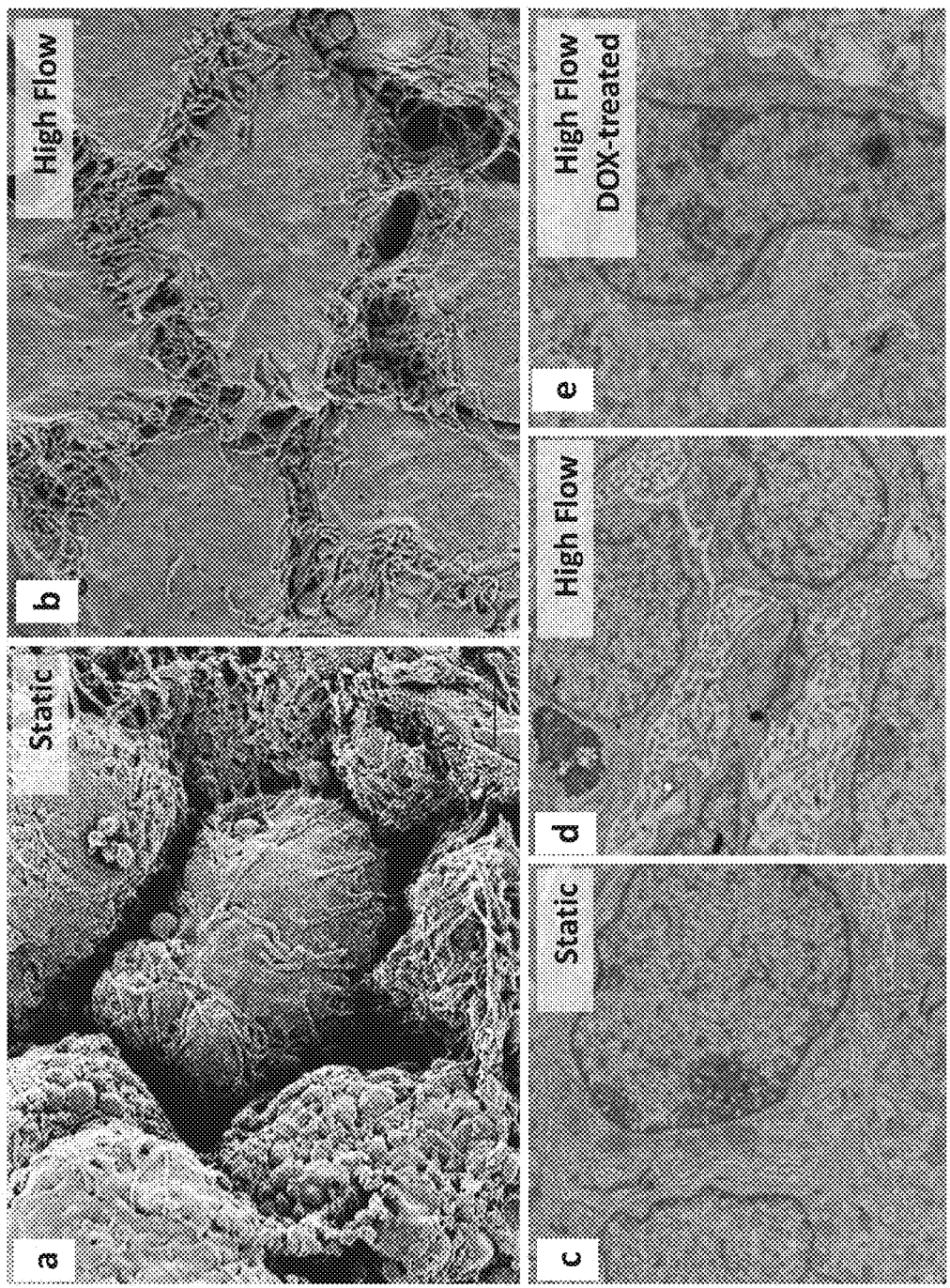
FIG. 29 shows that prominent foot processes form within vascularized kidney organoids cultured under high flow conditions: (a,b) SEM images; and (c,d) TEM images of kidney organoids on day 21 showing that foot process-like formations are more prominent in the high flow condition, compared to static conditions on chip. Furthermore, kidney organoids under high flow that are given 24 h of doxorubicin (DOX) treatment from Day 20 to Day 21 of culture show evidence of glomerular-specific damage including foot process fusion or effacement. All scale bars=1 µm.

Vascularization of glomeruli in vivo commences with invasion of an S-Shaped body (SSB) by a single capillary loop, around which podocytes coalesce with formation of a primitive Bowman's capsule (capillary loop stage, CLS), followed by vascular expansion to form nascent glomerular tufts in early corpuscles. Following 10 days of exposure to high FSS at day 21 of the overall protocol, glomeruli in vitro vary in a spectrum between SSB, CLS, and early corpuscle-like structures. Consistent with vascular invasion of an SSB, a $PECAM1^+$ vessel invades a cleft in an SSB-like structure (FIG. 19(a)). Meanwhile, the 'luminal' feature of an $MCAM^+$ $PECAM1^+$ vessel invading a $PODXL^+$ cellular cluster, surrounded by a putative Bowman's capsule, suggests CLS-like developing glomeruli (FIG. 19(b)). Renal corpuscle-like structures contain $MCAM^+$ $PECAM1^+$ vasculature suggestive of capillary loops (FIG. 19(c)). TEM shows analogous structures between developing glomeruli in high flow organoids and E14.5 mouse kidneys, revealing that organoids on chip may follow in vivo glomerular development through SSB, capillary loop, and early corpuscle stages (FIG. 19(D-I)). Importantly, capillary loop-like structures in organoid glomeruli exhibit open lumens without red blood cells, which are present in capillary loops in mice (FIG. 18(G-I)). Scanning electron microscopy (SEM) shows a thin-layered capsular structure suggestive of a parietal layer of epithelial cells (Bowman's capsule) that contains round cellular bodies with elongated cytoplasmic projections indicative of a visceral layer of epithelialium (podocytes) (FIG. 20(A)). In a manner similar to E14.5 embryonic mouse kidneys and human adult kidneys, grape-like clusters of visceral epithelial cells in organoids under high flow consist of round cellular bodies with interdigitating foot process-like structures (FIG. 27 (a-f)). The cytoplasmic projections, consisting of primary stalks and secondary side branches appear polarized and abut thin-layered membranes of capillary loop-like structures (FIG. 20(b), and FIG. 28(a-g), consistent with foot processes. Compared to static conditions, the foot process-like structures appear more prominent with significant upregulation of NPHS1 (nephrin) and SYNPO (synaptopodin), encoding foot process proteins, under high FSS (FIG. 21, FIG. 29(a-d)). Concurrently, the expression of podocyte adult transcription factors (WT1, CASZ1, CUX1, TEAD1) are significantly enhanced (FIG. 21). Further, these foot process-like structures can be fused or effaced by treatment with doxorubicin for 24 h as is observed in adult human kidneys (FIG. 29(e)). These data surprisingly indicate that culturing organoids on chip promotes glomerular vascularization and foot process maturation, which is required to facilitate functional morphogenesis of podocytes in vitro.

In summary, we have demonstrated that developing kidney organoids subjected to high FSS on a chip exhibit significant enhancement in the abundance and maturity of vasculature with concomitant morphogenesis of tubular epithelial cells and glomeruli in vitro. The ability to create vascularized kidney organoids in vitro will facilitate studies of vascular and kidney development, nephrotoxicity, tubular and glomerular disease, and kidney regeneration. The application of FSS to other organoid types may similarly facilitate their development from embryonic stages to more functional organ equivalents in vitro. The application of FSS to other organoid types in a similar embodiment may also facilitate vascularization and cellular maturation in vitro.

Based on the studies described herein, it was determined that including adult exogenous GMECs does not matter for vasculature to form, in fact, it might be detrimental. VEGF and PMA addition did not help as well, but 1.5 to 2% FBS helped sustain vascular growth. Surprisingly, it was also shown that the age of RV is very important: the earlier (younger) the better, Day 11-14 for perfusion works best for glomerular development, but for vascular development a longer range can also be sufficient. Surprisingly, the effect of perfusion (direct or indirect) was significant: for direct perfusion at shear stresses ~0.01 to 10 $dyn/cm^2$ and possibly greater. Surprisingly, it was also determined that substrate must allow the stromal population to invade.

Certain additional embodiments relate to a kit comprising a vascularized renal tissue construct or organoid produced by the method described herein, and an enclosure with a single inlet and single outlet for media. The kit may also comprise media and/or a perfusion pump, and/or instructions for using the kit.

Certain further embodiments relate to a kit comprising a vascularized renal tissue construct or organoid produced by the methods described herein and an enclosure with a single inlet and two outlets. The kit may also comprise media, and/or a perfusion pump, and/or instructions for using the kit.

EXAMPLES

Figure 2A:
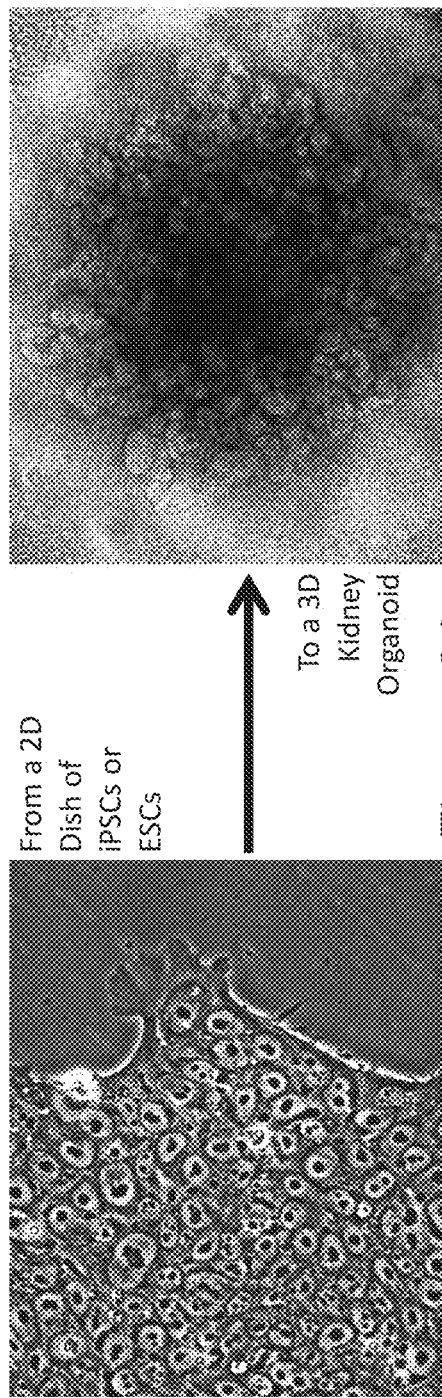
FIG. 2A illustrates how exemplary renal organoids can recapitulate kidney tissue.

Methods:

Early nephron organoids (developing organoids) from both human embryonic stem cells (hESCs) and induced pluripotent stem cells (hiPSCs), as illustrated in FIG. 2A were embedded in and on extracellular matrix (ECM) in 3D perfusable chips (FIG. 3).

Figure 2B:
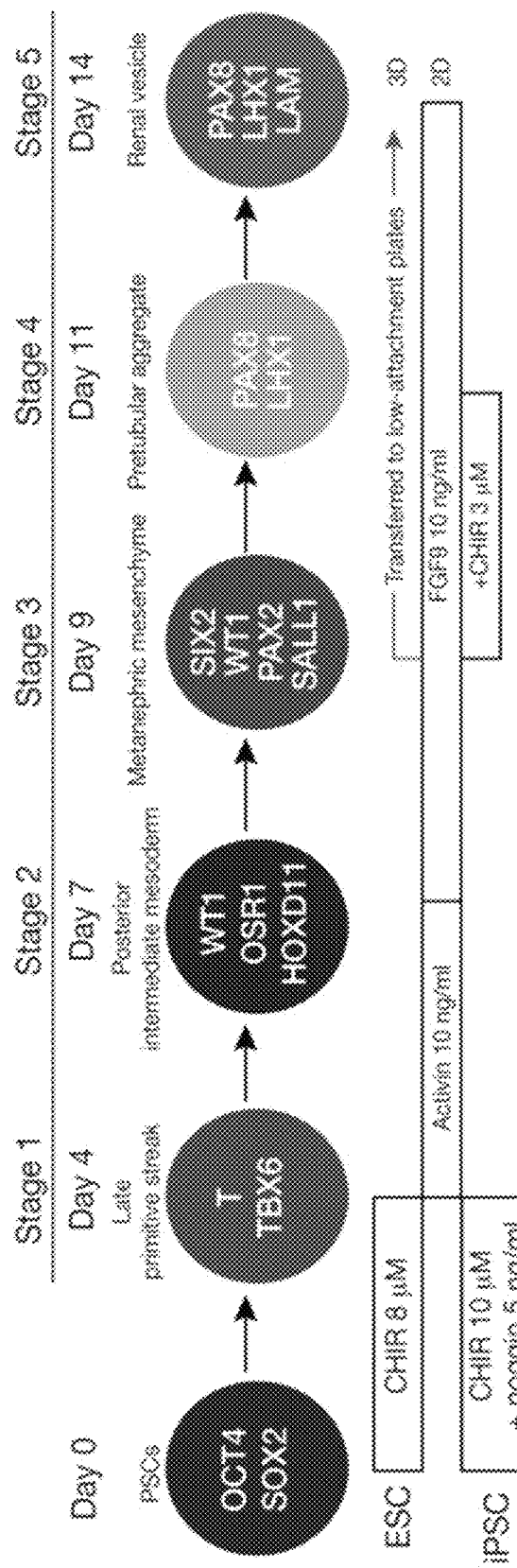
FIG. 2B shows an illustration of the exemplary culturing step of the developing organoids or organoids in the prior art (Morizane et al., Nature Biotechnology, 2015).

Specifically, as illustrated in FIG. 2, pretubular aggregates (day 11-14 of the culturing step) were placed in perfusable chips on top of or in an extracellular matrix material (ECM). FSS was applied for 1 to 55 days or more.

The degree, distribution, and maturation of vascular networks were evaluated by immunostaining, RT-qPCR, and flow cytometry for FLK1, CD146, and CD31 at regular intervals when subject to variable degrees of fluidic shear stress as well as of growth factors including VEGF, as compared to controls in static chips.

Results:

Described herein are results showing that by subjecting renal organoids to the right combination of underlying ECM, medium components, and fluidic shear stress, the abundance of vasculature, the incidence of capillary invasion of glomerular clefts, the number of vascularized glomerular structures as well as peritubular vasculature are significantly enhanced. We also demonstrate that the vasculature contains open lumens which can be visualized with fluorescent beads, indicating that vasculature in the organoids are perfusable.

Example 1: Effects of Chemical Additives on Renal Organoids

Methods: To determine effects of chemical additives on the developing developing organoids, the vesicles (age 11, 12, 13 and 14 Days) were treated with VEGF additives, GMEC media, PMA additives, antibiotics, or FBS or FCS additives and other components in advanced RPMI media as a base in both static and perfused conditions. The extent and abundance of vasculature was studied using immunostaining.

Conclusions: FIG. 22 encapsulates most of the conditions tested (ECM, media additives, day of organoids/age, etc.) There were no measureable effects of the CD31+ population of cells when the cells are treated with antibiotics, VEGF, PMA, or GMEC media. The pronounced effect of adding FBS was clear—the vasculature formed (CD31+ cells) with more abundance in this case. Vasculature can be seen at day 11 RV, as well as at day 14 RV.

Example 2: Comparing the Effects of Perfusion on Different Ages of Renal Vesicles (does the Age of the RV Matter?)

Methods: Developing organoids of different ages (Days 9-14) were attempted to embed on perfused chip using the gelbrin substrate (2 wt % gelatin, 10 mg/mL fibrin, 0.2% TG). They were perfused with advanced RPMI media+1.5% FBS at FSS varying between 0.000001 and 10 dynes/cm$^2$.

Figures 22A, 22B:
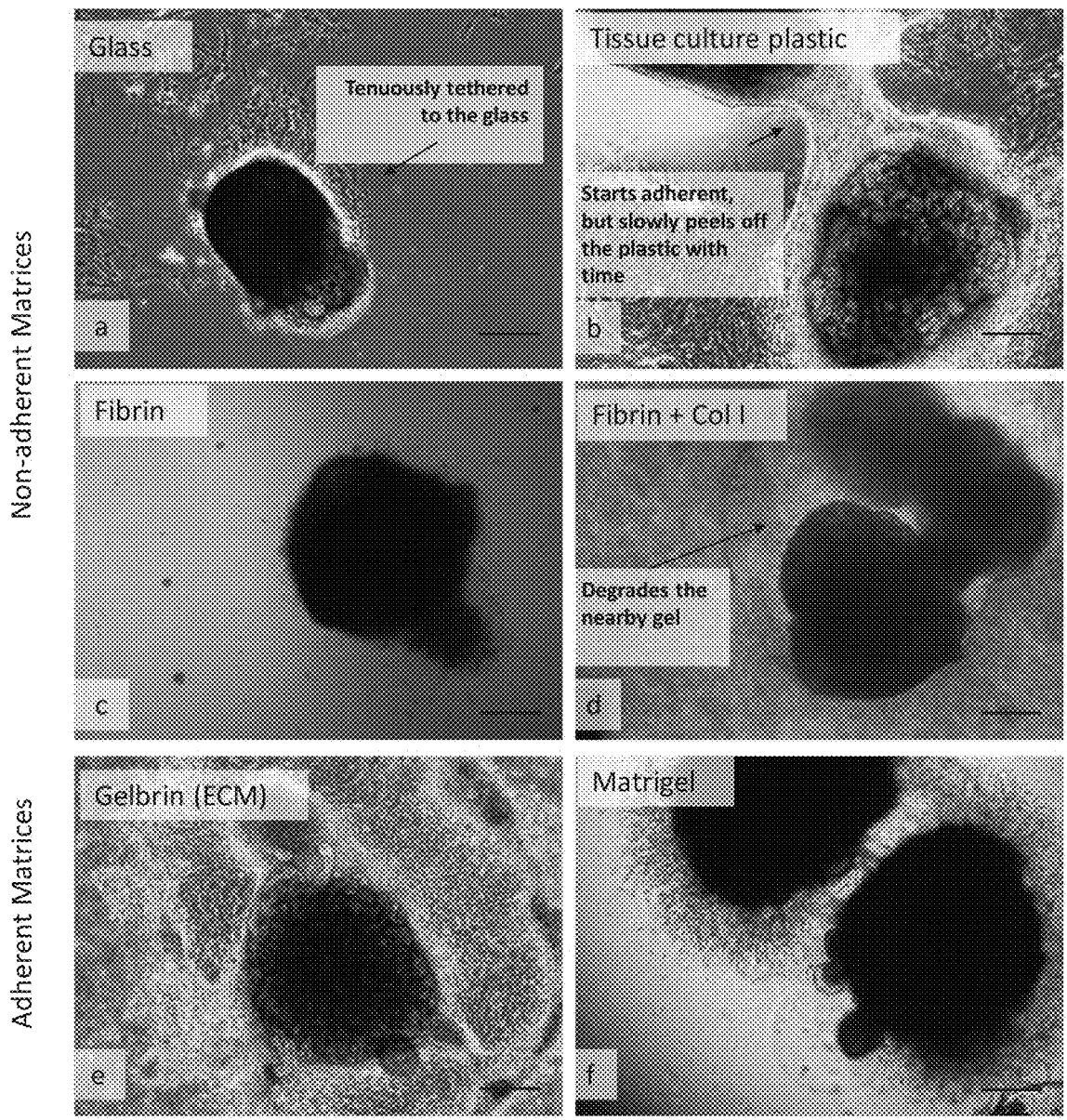
FIG. 22 shows kidney organoid-ECM interactions under static conditions. Developing organoids at Day 14 are placed on different extracellular matrices (ECMs) for one week to study their effect on vascular development. Non-adherent matrices, defined as those where cells from the organoid did not remain attached or did not strongly interact with the substrate include: (a) plasma-treated glass, (b) tissue culture plastic, (c) fibrin, and (d) a fibrin and collagen I network, scale bars=300 µm. On adherent ECM, (e) gelbrin (a gelatin-fibrin network) and (f) Matrigel™, the kidney organoids exhibited strong attachment and remained undisturbed by shaking, perfusion, or rocking, scale bars=300 µm.

Conclusions: Organoids embedded on Days 9 or 10 were too fragile and dissipated or never differentiated under FSS. FIG. 22(b) highlights how if Day 11 developing organoids are used, they have the potential to form highly differentiated structures with capillary invasion of glomerular clefts. Developing organoids at Days 12 and 13 results were similar to Day 11. If embedded on Day 14, vascular invasion of glomerular structures was observed at severely less levels.

Example 3: Effects of Perfusion or FSS on the Development of Renal Organoids

Methods: Developing organoids of different ages (Days 11-14) were embedded on perfused chip using the gelbrin substrate (2 wt % gelatin, 10 mg/mL fibrin, 0.2% TG). They were perfused with advanced RPMI media+1.5% FBS at FSS varying between 0 and 10 dynes/cm$^2$.

Figure 6:
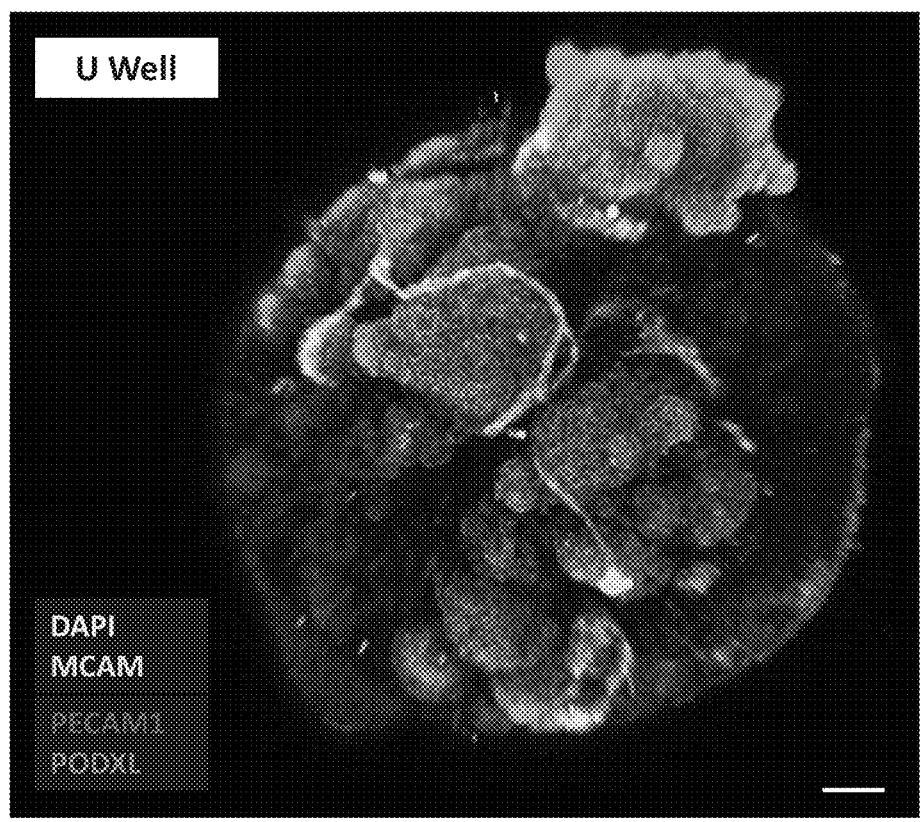
FIG. 6 depicts whole mount confocal 3D renderings for vascular markers in organoids under static U-well conditions, scale bar=100 μm showing that fluidic chip design and culture methods described herein permit nephrogenesis and promote vascularization of renal organoids.

Conclusions: FIG. 6 shows effects of perfusion on the development of renal organoids. FIG. 6 shows the abundance of vasculature is significantly increased under higher FSS conditions (0.01 dyn/cm$^2$ or more).

The RT-qPCR results further corroborate these results. Specifically, qPCR found higher levels of vascular markers and precursors, VEGF, FLK$_1$, CD146, and CD31 in high FSS conditions in comparison to static and low FSS controls.

Example 4: Vascular Development in Organoids with Time

Methods: Developing organoids of different ages (Days 11-14) were embedded on perfused chip using the gelbrin substrate (2 wt % gelatin, 10 mg/mL fibrin, 0.2% TG). The developing organoids were perfused with advanced RPMI media+1.5% FBS at FSS varying between 0 and 10 dynes/cm$^2$.

Conclusions: FIG. 6 depicts vascular development in organoids with time. They transform from a cellular spheroid at Day 12 to differentiated tubular structures with increasing amounts of vasculature with time (see, e.g., increase in vasculature seen on days 16 and 21, as compared to day 12).

Example 5: Effects of the Substrate on the Growth of Organoids

Methods: To determine the optimal substrate for the developing renal organoids, various substrates (e.g., glass, plastic, Fibrin+Collagen I, Gelbrin) were tested in both static and FSS conditions. The substrates, ideally, must allow for adhesion of the organoid and some degree of stromal invasion and remodeling of the matrix.

Conclusions: FIG. 22(a) illustrates organoids grown on various underlying substrates. It was demonstrated that substrates with a nanoporous component with adhesive cell binding sites, like Matrigel™ or gelatin, caused the organoid to adhere strongly and allowed for outgrowth of the stromal and vascular cell population, which ultimately led to the best vascular results (the most enhanced organoid vascularization and maturity).

Surprisingly, macroporous substrates alone with adhesive cell binding sites like Collagen I or Fibrin, or combinations thereof, did not produce enhanced organoids.

Further, placing organoids on preformed beds of vasculature, e.g., combinations of HUVEC and HNDF cells in fibrin, did not yield enhanced organoids.

Also, interestingly, the organoids are excellent at degrading the biomaterial substrates and replacing it with their own cell derived matrices over time.

Further, the amount of nanoporous material matters significantly. It was found that in gelbrin substrates, if gelatin concentrations exceeded 8 wt %, the vasculature would get choked out and not form properly in and around the organoids.

Example 6: Organoids Made with or Embedded Near Adult Vascular Cells has Little to No Effect on the Abundance of Vasculature in the Organoids or Glomerular Development and Glomerular-Vascular Integration Methods: Glomerular microvascular endothelial cells (GMECs) were pelleted with the SIX2+ cells at 1 and 10% at Day 8. Also GMECs were incorporated in the embedding ECM and in bioprinted channels near organoids embedded in ECM, both with and without FSS.

Figure 32:
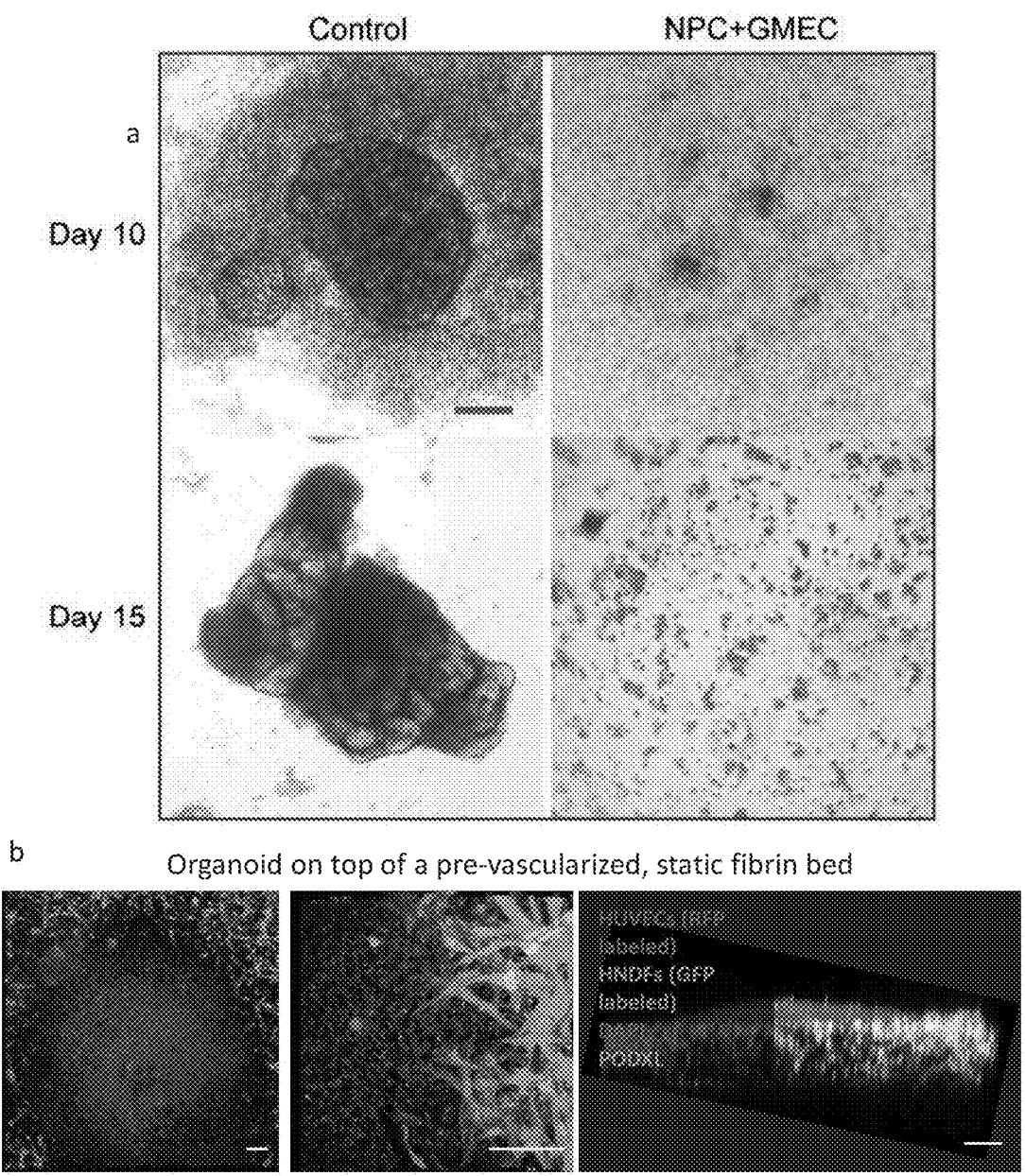
FIG. 32 shows that co-culture with adult human endothelia and fibroblasts inhibits nephrogenesis in developing kidney organoids. (a) NPCs derived from H9 are plated onto 96-well plates at 100,000 cells/well on Day 8 of differentiation. Primary culture of human glomerular endothelial cells (GMECs) are mixed with NPCs at 1,000 or 10,000 cells/well. On Day 10 of differentiation, spheroids start to form in control wells while added GMECs reduce formation of spheroid structures. On Day 15 of differentiation, control samples formed kidney organoids with epithelial structures, while those with added GMECs were inhibited during organoid formation. Scale bar=100 µm. (b) Organoids placed on a pre-formed bed of human umbilical vein endothelial cells (HUVECs) and human neonatal dermal fibroblasts (HNDFs) in 3D inside a fibrin gel, did not lead to enhanced maturity of the kidney organoids. Further, those organoids did not integrate with the ECM and the regular progression of their differentiation was effected, i.e., little to no tubular structures are visible in 3D whole mount confocal imaging, scale bars=100 µm. DAPl: 4',6-diamidino-2-phenylindole, PECAM1: CD31, MCAM: CD146, PODXL: podocalyxin.

Conclusions: FIG. 32 shows that when GMECs are introduced in the pellet at Day 8, it causes the organoids to not form properly; tubular structures are largely absent. GMECs near organoids also make little to no different in the abundance of vasculature and there is no observed hook up between GMECs and $CD31^+$ cells derived from the organoids.

Example 7: Flow-Enhanced Vascularization and Maturation of Kidney Organoids In Vitro Materials and Methods Kidney Organoid Millifluidic Chip Fabrication.

A silicone-based ink was used to 3D print customized perfusion gaskets, in which developing kidney organoids were placed on an engineered ECM layer (1 mm thick) and subjected to a controlled fluidic shear stress environment. The ink was composed of a two-part silicone elastomer (SE 1700, DOW Chemical) with a 10:1 base to catalyst (by weight) that was homogenized using a centrifugal mixer for 2 min (2000 rpm, AE-310, Thinky Corp, Japan). The silicone ink was printed within 2 h of mixing with catalyst. This ink was loaded in a syringe (EFD Inc., East Providence, RI) and centrifuged to remove any air bubbles before printing at room temperature. The chips were fabricated using a custom-designed, multimaterial 3D bioprinter equipped with four independently addressable printheads mounted onto a 3-axis, motion-controlled gantry with a build volume of 725 mm×650 mm×125 mm (AGB 10000, Aerotech Inc., Pittsburgh, PA USA). The silicone (PDMS) ink was housed in a syringe barrel to which a 410 μm diameter nozzles were attached via a luer-lock (EFD Inc., East Providence, RI, USA). Ink was extruded through deposition nozzles by applying air pressure (800 Ultra dispensing system, EFD Inc., East Providence, RI, USA), ranging from 10-90 psi, corresponding to print speeds between 1 mm/s and 5 cm/s. The customized perfusion chip gasket was printed by depositing the silicone ink through a tapered 410 μm nozzle onto 50 mm×75 mm glass slides. The gasket tool-path was created using a custom MATLAB™ script that generates G-code for a final gasket structure. After printing, the perfusion chip was cured at 80° C. in an oven for >1 h, stored at room temperature, and autoclaved prior to use. The organoid chamber was 15 mm wide by 3.6 mm high and 60 mm long; the ECM was placed on the base of the perfusion gasket and was 1 mm thick. The organoids, between 4 and 25 per chip, were placed centrally in an area of 8 mm wide by 3.6 mm high and 20 mm long as shown in FIG. 4(d).
Engineered Extracellular Matrix (ECM) Preparation and Rheology.

The extracellular matrix (ECM) is comprised of a network of gelatin and fibrin (gelbrin). To prepare the ECM components, a 15 wt/v % gelatin solution (Type A, 300 bloom from porcine skin, Sigma) was first produced by adding gelatin powder to a warm solution (70° C.) of DPBS (1×Dulbelco's phosphate buffered saline without calcium and magnesium). The gelatin was processed by stirring for 12 h at 70° C., and the pH was then adjusted to 7.5 using 1 M NaOH. The solution was sterile filtered and stored at 4° C. in aliquots for later usage (<3 months). A fibrinogen solution (50 mg/mL) was produced by dissolving lyophilized bovine blood plasma protein (Millipore) at 37° C. in sterile DPBS without calcium and magnesium. The solution was held at 37° C. without agitation for at least 45 min to allow complete dissolution. The transglutaminase (TG) solution (60 mg/mL) was prepared by dissolving lyophilized powder (Moo Gloo, TI) in DPBS without calcium and magnesium and gently mixing for 20 sec. The solution was then held at 37° C. for 20 min and sterile filtered before using. A $CaCl_2$ stock solution (250 mM) was prepared by dissolving $CaCl_2$ pellets in sterile water. To prepare stock solutions of thrombin, lyophilized thrombin (Sigma Aldrich) was reconstituted at 500 U/mL using sterile water and stored at −20° C. Thrombin aliquots were thawed immediately prior to use.

Prior to casting a layer of engineered ECM within the 3D printed chip, several components were mixed in advance at appropriate concentrations, including 10 mg/mL fibrinogen, 2 wt % gelatin, 2.5 mM $CaCl_2$ and 0.2 wt % TG. This solution was then equilibrated at 37° C. for 15-20 min before use to improve optical clarity of the ECM. Next, the solution was rapidly mixed with stock thrombin solution at a ratio of 250:1, resulting in a final thrombin concentration of 2 U/mL. Within 2 min at 37° C., soluble fibrinogen cured to a fibrin gel. For this reason, the ECM solution must be cast onto the base of the perfusion chip immediately after mixing with thrombin. The gasket with ECM was then placed in a sterile container and kept in the incubator for a minimum of 30 min prior to assembly with housing, media, and pretubular aggregate integration.

A controlled stress rheometer (DHR-3, TA Instruments, New Castle, DE) with a 40 mm diameter, 2° cone and plate geometry was used to measure the rheological properties of the ECM. The shear storage (G') and loss (G") moduli were measured at a frequency of 1 Hz and an oscillatory strain (y) of 0.01. Time sweeps were conducted by rapidly placing a premixed ECM solution that contains thrombin onto the Peltier plate held at 37° C. The G' of the final cured engineered ECM was approximately 800 Pa.

To prepare the ECM formulations shown in Extended Data Fig. S2, fibrin was used at either 10 mg/mL or 25 mg/mL with thrombin at 2 U/mL and 2.5 mM $CaCl_2$. The fibrin/Col 1 ECM was prepared by mixing fibrinogen solution at a final concentration of 25 mg/mL with Collagen I (Rat Tail Collagen I from Corning, 1 mg/mL) at a pH=7.5, a thrombin concentration of 2 U/mL, and 2.5 mM $CaCl_2$. Matrigel™ (Corning) was diluted by 50% with sterile PBS and cured at 37° C.

Another ECM formulation, which included fibrin along with human umbilical vein endothelial cells (HUVEC) and human neonatal dermal fibroblast (HNDF) cells was also made and evaluated. The pre-formed network of HUVECs and HNDFs were prepared by combining HUVECs:HNDFs at a 5:1 ratio at a concentration of 2M cells/mL in 10 mg/mL fibrin gel. The cells were cultured in 1:1 DMEM:EGM-2 (Dulbecco's Modified Eagle Medium, Endothelial Growth Medium 2, Lonza) plus 5% FBS for 3 days to allow for spontaneous tubulogenesis to occur prior to loading pretubular aggregates on top of the fibrin gel supporting the HUVEC:HNDF network. At this point, the media was changed to 1:1 EGM2: ARPMI (Advanced Roswell Park Memorial Institute+1× glutamax) and held in static conditions for 7 days.

Organoid Assembly and Perfusion on Printed Chips.

To assemble the kidney organoids-on-chip, pretubular aggregates (with ages between Day 11 and Day 14) in media were pipetted onto the top of the ECM on gasket in the window/area shown in FIG. 4(d). A large number of organoids can fit on chip and, typically, between 4 and 25 per run were used, but upwards of 100 or more can fit, if needed. The organoids were randomly spaced within the window of 8×20 mm. The gasket was then placed into a machined stainless steel base. Stainless steel pins were pushed through the PDMS at inlet and outlet and positioned such that they are above the ECM surface. Finally, a thick acrylic lid was placed on top (FIG. 4(a-e)). The lid and base were clamped together by four screws, forming a seal around the printed silicone gasket. Next, sterile two-stop peristaltic tubing (PharMed BPT) was filled with media and connected to the outlet of a sterile filter that is attached to a 10 ml syringe barrel (EFD Nordson), which served as a media reservoir. Organoid media (ARPMI+1× glutamax+1.5% FBS and 1% Antimycotic/Antibiotic solution) that was equilibrated for >3 h in an incubator at 37° C., 5% $CO_2$ was added to the media reservoir, and tubing from the reservoir was connected to the inlet of the chip (metal hollow perfusion pin). Tubing was also connected to the outlet of the chip through its respective stainless steel pin. A syringe was then used to exert slight pressure on the media in the barrel, forcing it to enter and completely fill the open gasket area, taking extra care not to disturb the pretubular aggregates. Hose pinch-off clamps were added at the inlet and outlet of the perfusion chip to prevent uncontrolled flow when disconnected from the peristaltic pump. To complete the closed perfusion circuit, tubing from the outlet was connected to the media reservoir. The media reservoir was equilibrated with atmospheric conditions in the incubator at all times by means of a sterile filter on top of the media reservoir. Media was changed every 2 to 3 days. The typical volume of media per organoid on chip and static on ECM was 0.5 to 0.8 mL. The typical volume of media per organoid in U well was 0.2 mL. It was determined that volume of media per organoid in the range of 0.2 mL to 1 mL per organoid had no measurable effect on the resulting vasculature on chip in high flow conditions. Furthermore, organoid height was measured in order to understand the dynamic changes evolving on chip during organoid development.

It was found that kidney organoids under low and high FSS initially flatten, then grow to heights greater than U-well controls. Thus, gross morphologic height changes are not a dominant variable controlling the enhancement in vascularization since the heights were similar in low and high FSS conditions by Day 21, while the vasculature was dramatically enhanced in high FSS only (FIG. 3).

A peristaltic pump was used to direct media into the gasket in a closed loop circuit at volumetric flow rates ranging from 40 μL/min to 4.27 mL/min. During the first 12 to 24 hours of culture on chip, pretubular aggregates were subjected to low flow rates of 40 μL/min or less. These extremely low flow rates provided nutrient supply without high shear stresses that could break the connection forming between the aggregates and the ECM below. After 24 hours, the aggregates were securely bound and the volumetric flow rate (Q) was raised to a value between 1.0 and 4.27 mL/min.

Flow Profile Analysis.

Flow modeling was performed using COMSOL Multiphysics simulation software. The fluid flow velocity profile was calculated by assuming a Stoke's Flow, using a 1 mL/min volumetric flow rate. The channel comprised the curved surface of the gel, the silicone walls at the two sides, and the perfusion chip lid. For direct measurement of fluidic shear stress at the gel-channel interface, fluorescent beads were tracked within the organoid seeding region at various volumetric flow rates. To visualize the flow, perfusion chips were mounted onto a confocal microscope stage, and were perfused with PBS containing 0.4% v/v of a 2% solids solution of 0.5 μm 488 nm fluorescent beads (Thermo Fisher). The pump was connected to the chip via a 60 ft length of silicone tubing to dampen pulsatility to obtain a time-averaged shear-stress. Analysis was performed along an 8 mm long, transverse line centered on the mid-line of the channel and the organoid seeding region at two-thirds of the distance between the inlet and the outlet of the perfusion chip. Confocal videos of bead flow were captured using a window of 600 μm along the channel by 90 μm across. To estimate the velocity gradient for calculating shear stress at the gel-channel interface, four videos were captured at 40 μm-height intervals just above the gel surface. The mean bead velocity was extracted at each height by performing a cross-correlation of the video frames in a direction parallel to the bead flow. The peak location of the cross correlation represents the mean displacement of the beads over the timeframe of the two images used for cross-correlation. The cross-correlation timeframe was increased until the peak in the cross-correlation of the video dropped to below 6 standard deviations of the noise floor. The velocity was calculated as the ratio of the cross-correlation peak displacement and the time difference between the two frames used for cross-correlation. Velocities were calculated for each frame of the video, and averaged. The velocity gradient was measured using linear regression of the mean velocities at the four different heights. The fluidic shear stress was then calculated as the product of the gradient and a dynamic viscosity of 0.78 cP for DMEM at 37° C.[30] To measure the flow pulsatility, a 50 second video was captured at the midline of the channel, two-thirds of the distance between the inlet and the outlet, and the bead velocity was measured over time using the cross-correlation method described above (FIG. 4(e-g)). The predicted flow profile using COMSOL and direct measurements using bead flow were in good agreement, if assumed a rectangular cross-section. Wall fluidic shear stress in flow through a rectangular cross-section (τ, denoted as FSS) was calculated using the equation:

$$\tau = 6\mu Q/bh^2,$$

where μ is the medium viscosity,
b is the channel width, and
h is the channel height (the empty channel through with fluid flows is approximated as a rectangular cross-section (b=14 mm; h=2.6 mm), where the organoids reside.

In this study, the volumetric flow rates were varied to induce a low FSS that ranges from 0.0000001 to 0.0001 $dyn/cm^2$ and a high FSS that ranges from 0.008 to 0.035 $dyn/cm^2$. Note the channel dimensions can be reduced simply by increasing the ECM height, which yields a higher FSS at a given volumetric flow rate. We have constructed channel heights as small as b=0.5 mm, leading to FSS at ~1 $dyn/cm^2$, and organoids cultured on this chip exhibited comparable enhancements in vascularity and tubular/glomerular maturation, as compared to those subjected to an FSS ranging from 0.008 to 0.035 dyn/cm$^2$.

Cell Culture.

Human ESCs, H9 (WiCell) and human iPSCs, BJFF (provided by Prof. Sanjay Jain at Washington University) were maintained in feeder-free culture using StemFit® Basic02 (Ajinomoto Co., Inc.) supplemented with 10 ng/ml FGF2 (Peprotech) as previously reported. Human glomerular microvascular endothelial cells (GMECs), RFP expressing (Angio-Proteomie) were cultured using EGM2 media (Lonza) and used up to passage 9. Human umbilical vein endothelial cells (HUVECs), RFP expressing (Angio-Proteomie) were cultured using EGM-2 media (Lonza) and used up to passage 9. Human neonatal dermal fibroblasts (HNDF), GFP expressing (Angio-Proteomie) were cultured per supplier's instructions and used up to passage 15.

Organoid Preparation and Culture.

Figure 30:
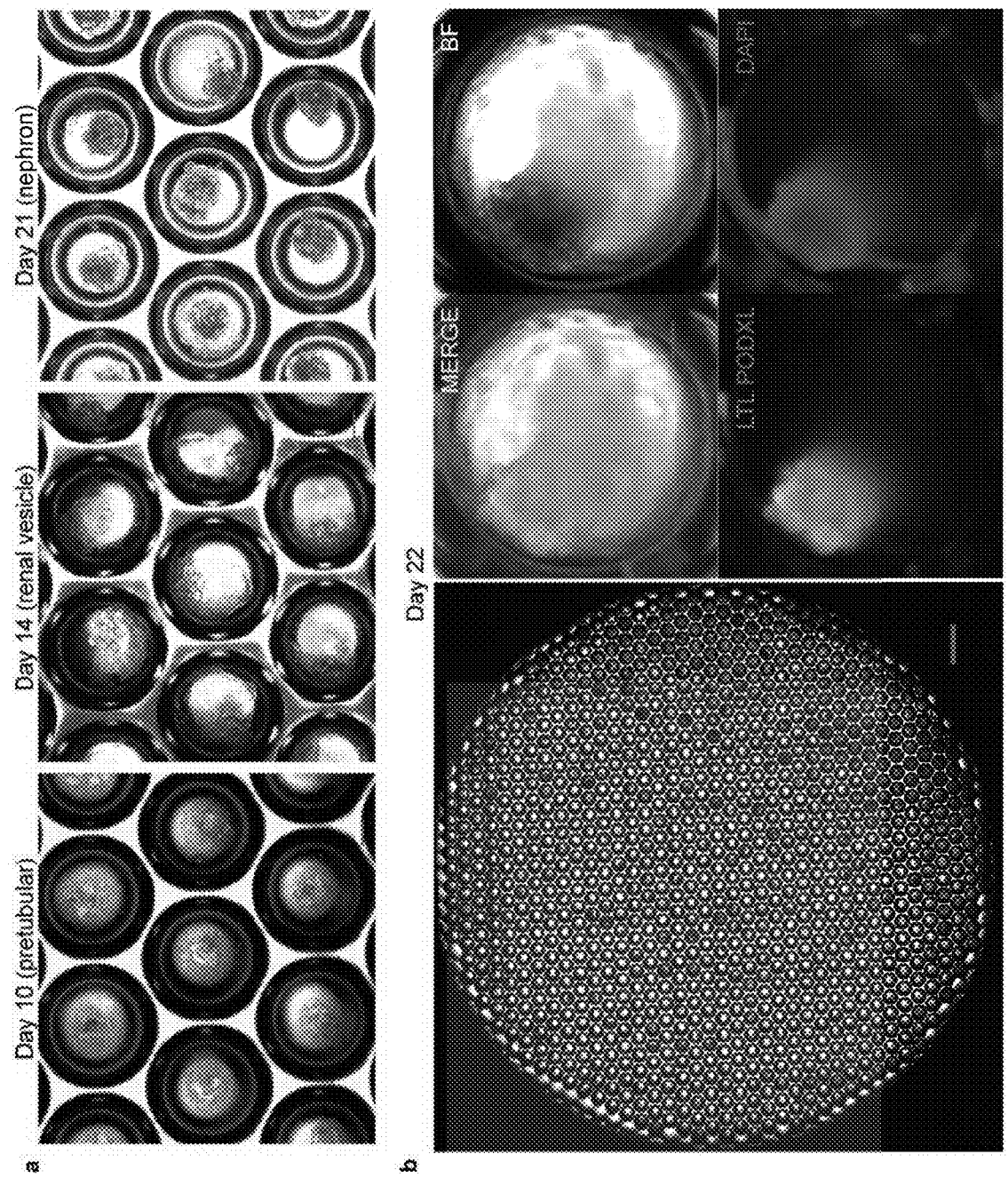
FIG. 30 shows kidney organoid generation in micro-well arrays. Nephron progenitor cells derived from H9 are plated onto 6-well culture plates that have patterned microwell surfaces, on day 8 of differentiation with 5,000 cells/microwell. (a) Bright field images show their morphological change over time. Dates of differentiation are indicated on the top of Brightfield images. Scale bars=200 mm. (b) A bright field image of whole well scanning on day 22 of differentiation (left). Immunofluorescent images of day-22 kidney organoids (right). LTL: lotus tetragonolobus lectin. PODXL: podocalyxin like. DAPl: 4',6-diamidino-2-phenylindole. Scale bars: 5 mm (left) and 200 mm (right).

Organoid preparation was covered in detail elsewhere (Morizane, R. & Bonventre, J. V., "Generation of nephron progenitor cells and kidney organoids from human pluripotent stem cells" Nat Protoc, 12:195-207 (2017)), but briefly hPSCs were differentiated into metanephric mesenchyme cells which included SIX2$^+$ nephron progenitor cells with approximately 80-90% efficiency, by a 3-step directed differentiation protocol (FIG. 3, bottom). Metanephric mesenchyme cells were differentiated into pretubular aggregates in suspension culture, and then the aggregates were transferred onto the chip (FIG. 3, top, anytime between Days 11 and 14 work (FIG. 22B). Further differentiation into kidney organoids were stimulated by the same differentiation protocol, reported previously except that 1.5% FBS (heat inactivated, Gibco) is added (Morizane, R. & Bonventre, J. V., "Generation of nephron progenitor cells and kidney organoids from human pluripotent stem cells," Nat Protoc 12:195-207 (2017)). This same process can be used to massively scale up kidney organoid production using Elplasia™, a culture plate that has patterned microwells (Kuraray) (FIG. 30). Using traditional methods, kidney organoids contain roughly 100,000 cells/aggregate. However, within the same footprint as a single well in a 6-well plate, approximately 1,000 mini-organoids can be produced, which contain approximately 5,000 cells/aggregate. Notably, when these mini-organoids were placed within current engineered microenvironment on chip, they behaved similarly to larger organoids and exhibited enhanced vascularization under high FSS conditions. These mini-organoids are advantageous, as their assembly is highly scalable and they can be imaged through their entire depth by confocal microscopy.

Next, several experimental conditions that did not lead to enhanced vascularization were studied. In particular, adding adult human primary GMECs, either by aggregating them with nephron progenitor cells at Day 8 or placing them in culture on ECM near renal aggregates or vesicles was not successful (FIG. 20). The developing kidney organoids either failed to form properly at Day 8 or HUVECS, HNDFs, and adult GMECs failed to integrate within the forming organoid, respectively (FIG. 32).

Doxorubicin (DOX) Exposure.

The chemotherapeutic drug DOX (Sigma) was dosed at 10 M for 24 h from Day 20 to Day 21 of culture in either static or high FSS conditions.

Bead Perfusion.

Figure 13:
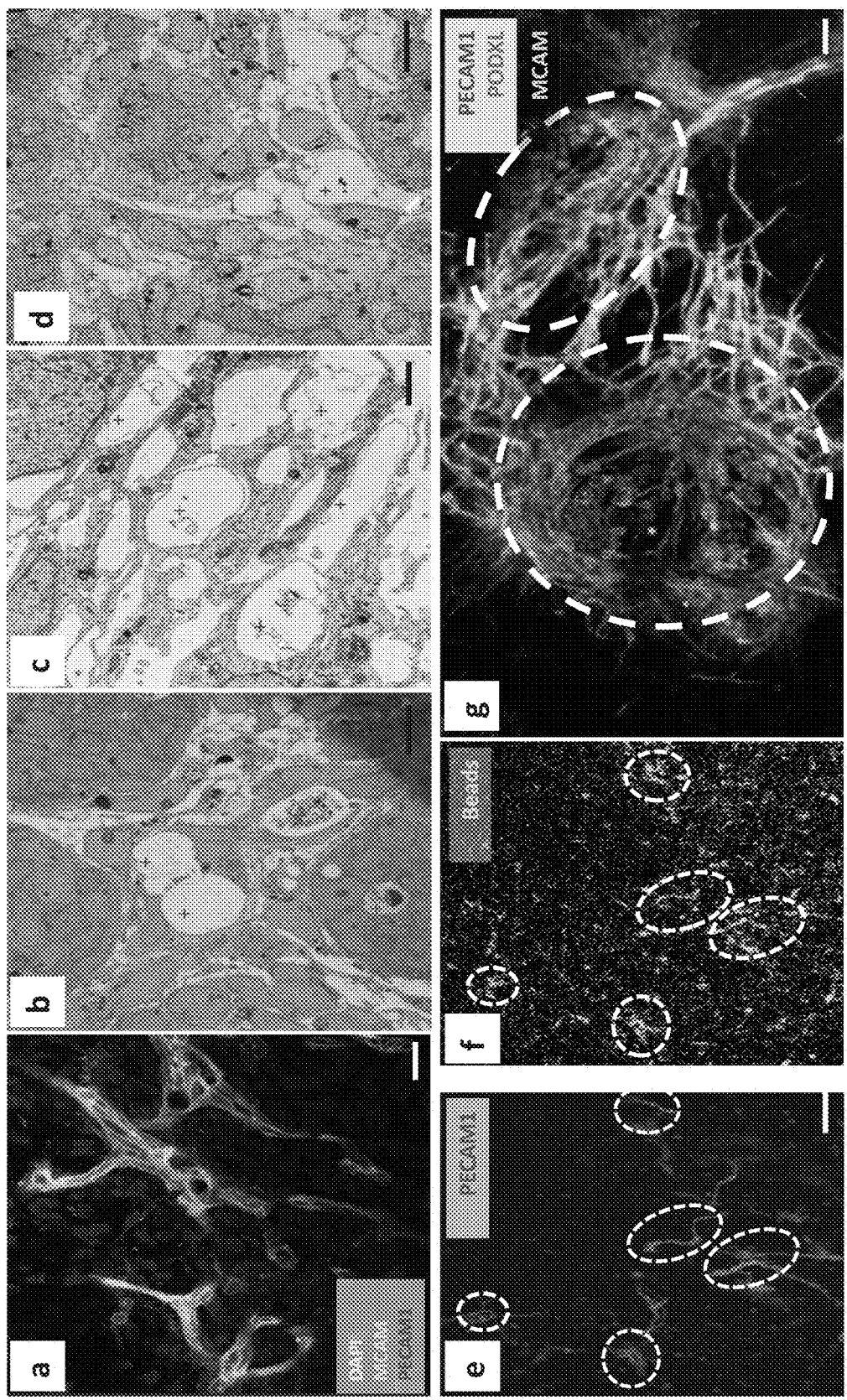
FIG. 13 shows in (a) A single z-slice from FIG. 23 in which white arrows highlight open lumens, scale bar=30 μm. (b-d) TEM images showing circular openings encompassed by a thin membrane that reflect vascular lumens when comparing (b,c) kidney organoids subject to high flow to (d) E 14.5 mouse embryonic kidney in vivo, noting hierarchical luminal diameters that vary from 2 to near 20 μm (red plus signs reflect vascular lumens), scale bars=10 μm for (b,d) and 2 μm for (c). (e,f) A Z-slice at the base of a kidney organoid under high flow, showing in (e) the vascular network and in (f) the accumulation of fluorescent beads within the vascular network, scale bars=100 μm. (g) Whole mount confocal 3D rendering of vasculature bridging between two adjacent organoids (outlined by dashed white lines, scale bar=100 μm. DAP1: 4',6-diamidino-2-phenylindole, PECAM1: CD31, MCAM: CD146, KDR: FLK1, PODXL: podocalyxin, PDGFR-β: platelet derived growth factor receptor beta, *p<0.05, p<0.01, *p<0.001.
Figure 25:
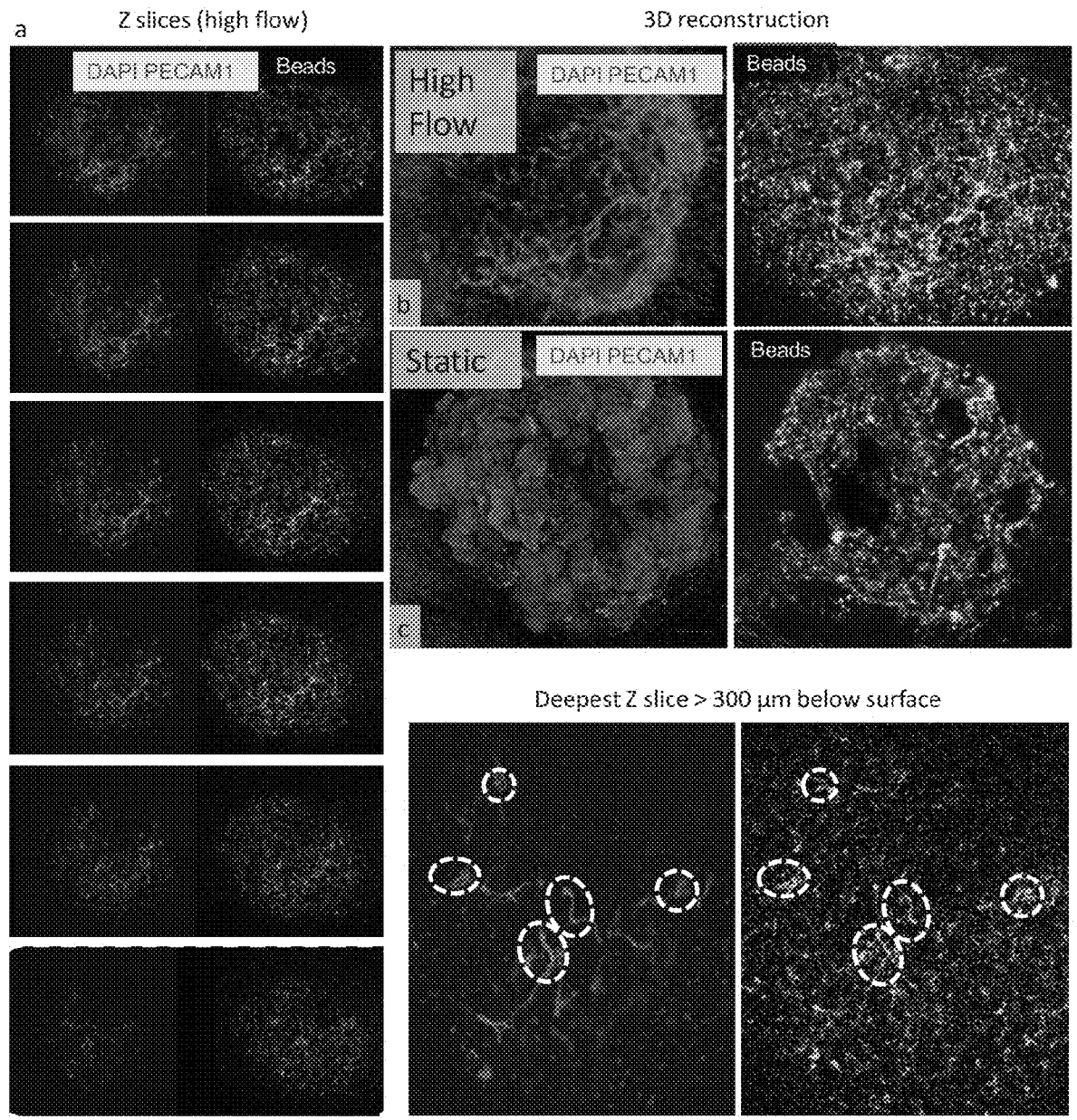
FIG. 25 demonstrates that fluorescent beads perfuse through open lumens in PECAM1+ networks in organoids cultured under high flow. Fluorescent beads (200 µm in diameter) are perfused in the media of organoids cultured under high flow at Day 21; beads are also added to static culture media and rocked for 2 hours. Z-stack confocal images of the beads are captured live in high flow (a,b) and static conditions (c). (d) The organoids are then fixed and stained for DAP1 and PECAM1 and confocal z-stacks are rendered of the same area (a) and 3D rendered (b,c) which show a pervasive PECAM1+ network under high flow. Further, the slice deepest in the Z-stack for the high flow condition (>300 µm below the top organoid surface) shows accumulation of beads in PECAM1+ regions (white dotted circles), confirming that beads can traverse the organoid thickness and accumulate in PECAM1+ lumenal vessels through the depth of the organoid. Scale bars=100 µm. DAP1: 4',6-diamidino-2-phenylindole, PECAM1: CD31, MCAM: CD146.
Figure 26:
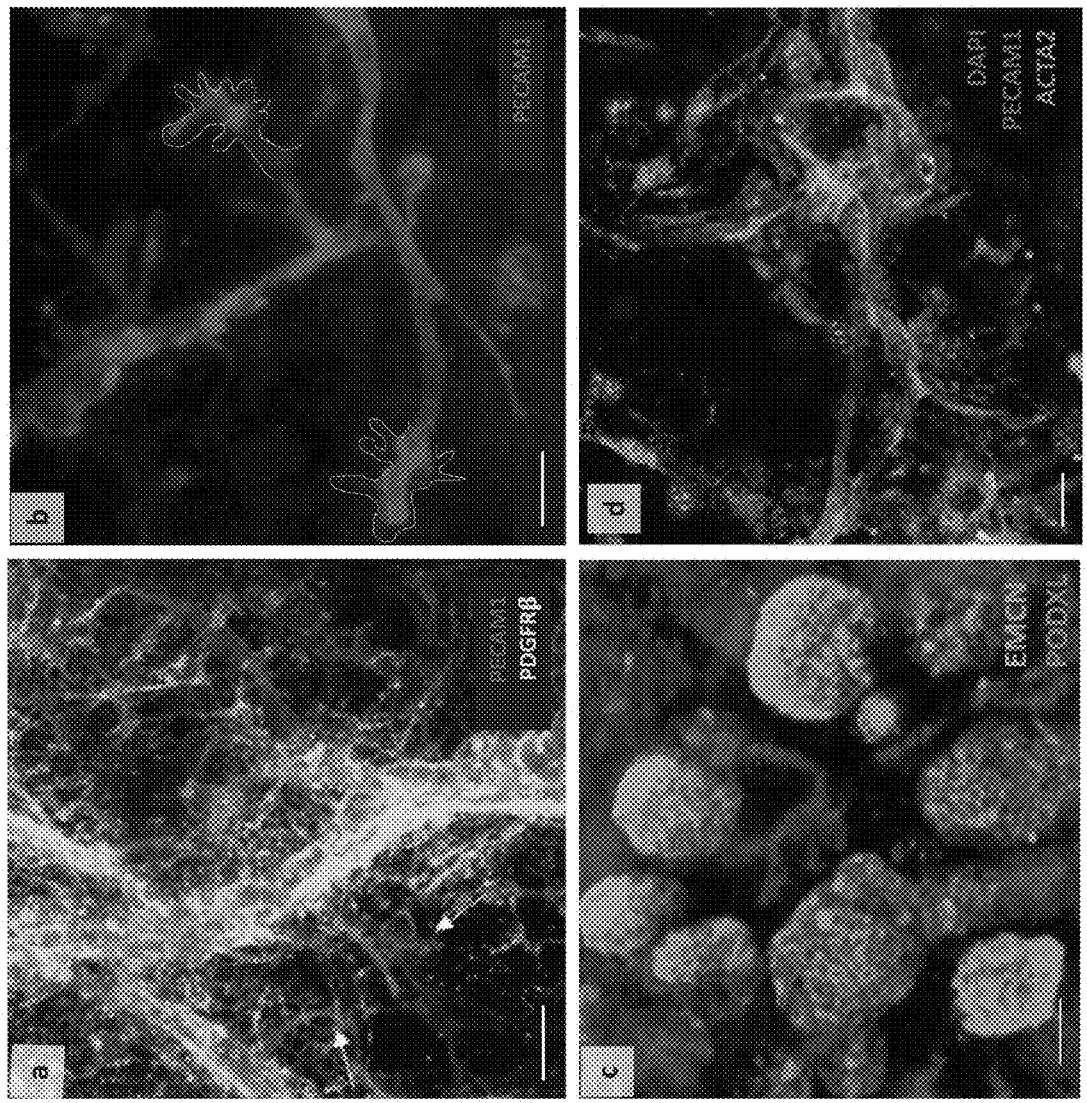
FIG. 26 shows that vascular networks in kidney organoids cultured under high flow conditions exhibit features suggestive of angiogenesis and induction of venous and arterial lineages: (a) Immunostaining of kidney organoids in the high flow condition on day 21 of differentiation depicting PECAM1$^+$ sprout-like structures (white arrow) that lack a lining of PDGFR-β$^+$ mural cells, which is seen in higher caliber vascular networks from which the sprout-like structures arise, scale bars=15 µm. (b) Immunostaining of similar samples to (a) showing that the terminal portion of PECAM1$^+$ networks adopt a tip cell morphology (outlined in dashed white lines), suggesting angiogenesis, scale bar=20 µm. (c,d) Immunostaining of kidney organoids in the high flow condition on day 21 of differentiation showing regions of vasculature stain for the (c) venous marker, EMCN$^+$, and associate with (d) smooth muscle-like ACTA2$^+$ cells consistent with arterial induction, scale bars=40 µm (c) and 20 µm (d). DAP1: 4',6-diamidino-2-phenylindole, PECAM1: CD31. PODXL: podocalyxin, EMCN: endomucin, ACTA2: alpha smooth muscle actin (αSMA).

At Day 21 of differentiation in either static or perfused conditions, 100 nm fluorescent beads were added to the media (FluoSpheres™ from ThermoFisher, carboxylate terminated) at a dilution of 1:1000. For the static case, the organoids were gently shaken in the incubator for 2 h in the presence of bead-laden media. For the perfused conditions, the kidney organoids-on-chip were perfused with bead-laden media under high FSS conditions for 2 h in the incubator. The kidney organoids were then imaged using confocal microscopy to determine the distribution of the fluorescent beads within them. Fiduciary markers in the sample were used to ensure that after fixing, washing, and staining for PECAM1 (CD31), the same confocal Z-stack was collected with endothelial markers and can be properly correlated with bead location. Note, the beads were nearly completely flushed out during the washing and primary and secondary staining process. Z-stack images and reconstructions were rendered (FIGS. 13 and 25).

While it was found that the beads non-specifically bind to both static and perfused organoids, they concentrated in larger luminal CD31$^+$ structures and were observed in those luminal spaces throughout the entire depth of those organoids under high FSS conditions.

To obtain a live perfusion bead movie, slightly different techniques were used. First, live imaging required a very bright and lasting stain of the vasculature. Live tagging of CD31 and CD146 was tried using fluorophore conjugated antibodies, but the signal was not strong. Instead, a rhodamine-conjugated agglutinin (ULEX: Ulex europaeus Agglutinin 1 (UEA 1) from Vector Laboratories) was used as the signal overlaps with both CD31 and CD146 and was bright. As scattering from thick organoid tissue and non-specific deposition of beads from superfusion alone were known problems, imaging the vessels live within the first 15 minutes of starting bead perfusion was performed instead. We imaged near the bottom of the organoid, close to the glass where perfusion was likely limited in comparison to the top of the organoid, but so was non-specific bead uptake. Before imaging the organoid was perfused in ULEX at a 1:200 dilution in media. ULEX was quickly rinsed away with fresh media at a 3× volume dilution and replaced with media+beads at a 1:1000 dilution. The imaging was taken for 900 frames at 400 ms between frames and half way through the ULEX laser was turned off in order to capture the bead flow alone on chip. The video was rendered at 20 frames per second.

Flow Cytometry.

To prepare live cells for flow cytometry, several digestion steps were required. First, the organoids (10 to 15 per condition) were cut away from the ECM and placed in a 15 mL Falcon™ tube. Excess media was removed and the sample was washed with PBS without $Ca^{+2}$ and $Mg^{+2}$. Next 100 μL of 2.5% trypsin (Corning) in 10 mM EDTA (Sigma-Aldrich) was added for 2 min at 37° C. Then 1.9 mL of PBS without $Ca^{+2}$ and $Mg^{+2}$ was added and the tube was centrifuged at 300×g for 4 min. The supernatant was aspirated and 200 μL of collagenase IV (STEMCELL Technologies) was added and the suspension was pipetted to further break up the organoid. The samples were incubated for 10 min at 37° C. After more pipetting, 5 mL of PBS was added and samples were centrifuged at 300×g for 4 min. The supernatants were aspirated and the cells were incubated on ice for 30 min with FLK 1-555 (Bioss) at a 1:10 dilution in PBS without $Ca^{+2}$ and $Mg^{+2}$. The samples were washed 3× with PBS without $Ca^{+2}$ and $Mg^{+2}$ and then suspended in stains, either DAPI (Sigma) or SYTOX™ Red (ThermoFisher 1:1000 dilution) in BD FACS Flow Buffer in a total of 300 μL of fluid. Samples were sent through a Falcon 70 m filter prior to imaging in flow cytometry. Cells were analyzed by flow cytometry (BD LSR Fortessa) and data was collected from n=100,000 cells per sample. All gates used to ensure live, homogenous cells were counted are shown in FIG. 31.

Figure 31:
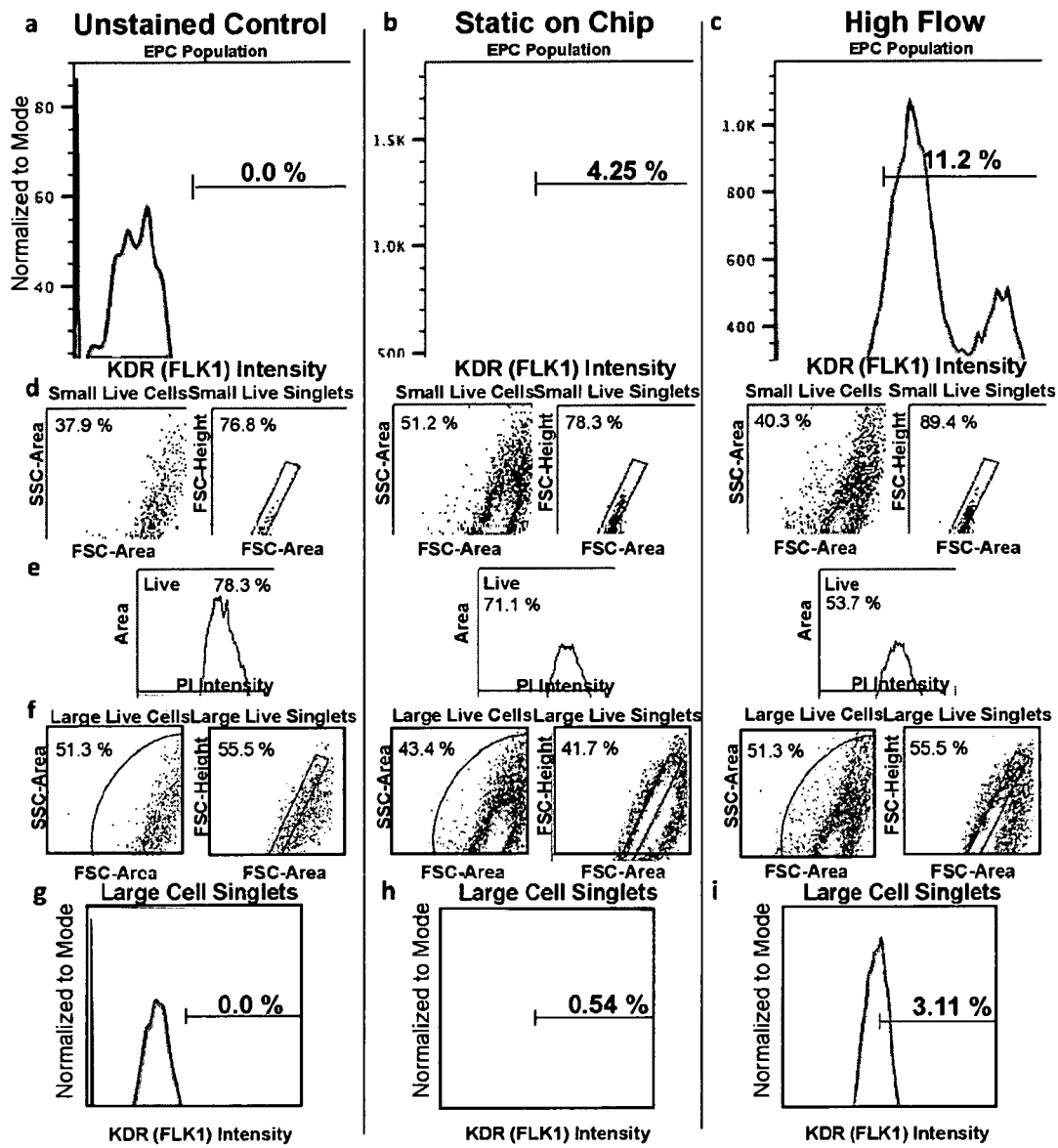
FIG. 31 shows flow effects on vascular precursor cells KDR+(FLK+). Flow cytometry data showing that KDR+ cells represent (a) 0.0% in unstained controls, (b) 4.25% in static organoids on chip, and (c) 11.2% under high flow of total live cells in dissociated organoids at Day 21, compared to and (a). (d-f) Gating strategy to fractionate live cells into small cell and large cell fractions of kidney organoids. In the large singlet cells, (g) 0.0% in unstained controls, (h) 0.54% in static conditions on chip compared to (i) 3.11% under high flow are KDR+ cells.

Note that in FIG. 31(d,f) a bimodal population of large and small cells sizes for Day 21 heterogenous kidney organoids was observed. Expectedly, KDR+ EPCs were found predominantly in the small fraction. Presumably, the KDR+ cells that persist in the large cell fraction were due to endothelial differentiation with morphologic changes.

qRT-PCR.

Kidney organoids are manually extracted from perfusable chips by pipette. RNA is isolated from kidney organoid samples using an acid-guanidinium-phenol based reagent, TRIzol® (Invitrogen) according to manufacturer's protocol. A minimum of 6 organoids are used per sample. cDNA is synthesized using a High-capacity cDNA Reverse Transcription kit (Applied Biosystems). Quantitative Real-time PCR is performed using a concentrated, ready-to-use reaction master mix, iTaq™ SYBR® Universal Green Supermix (Bio-Rad) and a BioRad® iQ™5 Multicolor Real-time PCR Detection System. Primer sequences are designed using FASTA sequences (Pubmed) and verified using Primer3, and one of the primers from the pairs of primers is designed to include an exon-exon junction. Target genes are normalized to Glyceraldehyde 3-phosphate dehydrogenase (GAPDH) expression. The mRNA expression is calculated using the $2^{-\Delta\Delta Ct}$ method, expressed as an n-fold difference relative to the control group, and reported with standard error bars. Of note, cDNA quality was confirmed by DNA gel electrophoresis of the housekeeping gene, GAPDH, across samples.

Primers

| SEQ ID NO | Gene | Forward | SEQ ID NO | Reverse |
|---|---|---|---|---|
| 1 | ABCB1 | CCATGCTCAGACAGGATGTG | 2 | TTCCTGTCCCAAGATTTGCT |
| 3 | AQP1 | GTCCAGGACAACGTGAAGGT | 4 | GAGGAGGTGATGCCTGAGAG |
| 5 | ATPIA1 | CCAATTGTGTTGAAGGCACC | 6 | CCGTGATGATGTGGATAAAATGT |
| 7 | BNC2 | CTATGTTCTAGCCCAGACCCC | 8 | TATGTTGGCACTGTGTCTGTCT |
| 9 | CASZ1 | CACTGTCAAGAACGGACTGC | 10 | ACGTCCTGCTTACTCGTGAA |
| 11 | CUX1 | GCTGAAGTGAAAATCAAGAGGTTA | 12 | GCTTTGAGGTGGTGACATC |
| 13 | GAPDH | CAATGACCCCTTCATTGACC | 14 | GACAAGCTTCCCGTTCTCAG |
| 15 | KDR | AGGACTTCCAGGGAGGAAATAA | 16 | AAAGTAATTTCAGGACCCCTGG |
| 17 | LRP2 | TGTGATGCAGCCATCGAACT | 18 | TGCATTTGGGGAGGTCAGTC |
| 19 | MCAM | CGTCTCGTAAGAGCGAACTTG | 20 | CGATGTATTTCTCTCCCTGGTC |
| 21 | NFIA | ACAGGTGGGGTTCCTCAATC | 22 | TGGGTGTCGAGTAGGTTGG |
| 23 | NPAS2 | TTTTGCAGAAACACAATGAAGTC | 24 | CCAAGGAGAGGCGTGATAC |
| 25 | NPHP1 | ACCGGTGAAGAATACATCGCT | 26 | TATAAGGCTCTAGGTAGGTTCTGGG |
| 27 | NPHP6 | AGGATACCAAAGGAGCCCAA | 28 | TCTTCAAGACTGCTGATTGTACG |
| 29 | NPHS1 | GACCCAGCTTCCCATCACTA | 30 | GCATTGGAGAGGAGCAGAAG |
| 31 | PECAM1 | TCATTACGGTCACAATGACGA | 32 | GAGTATCTGCTTTCCACGGC |
| 33 | PDGFR-β | ATACCCCCGCAAAGAAAGTG | 34 | CACTCTCCGTCACATTGCAG |
| 35 | PKD1 | AACAAGTCTTTGGCCATCAC | 36 | TACTCGTTCAGCACGGTGAC |
| 37 | PKD2 | TCTTGGCAATTTCAGCCTTT | 38 | GCACAACGATCACAACATCC |
| 39 | PKHD1 | CCATTCTCTGCCAGGTTAGC | 40 | ACCCCTAATCAGCACAGTGG |
| 41 | SLC2A2 | GCTGCTGAATAAGTTCTCTTGGA | 42 | CTAAAGCAGCAGGACGTGGT |
| 43 | SLC6A19 | ACAACTGCGAGAAGGACTCG | 44 | GTGCTGAAGCAGTCGTCGTA |
| 45 | SLC9A3 | GGCAGGAGTACAAGCATCTGT | 46 | CCCGGTCCTGTTTCTCGTC |
| 47 | SLC34A1 | TCACGAAGCTCATCATCCAG | 48 | TTCCTCAGGGACTCATCACC |
| 49 | SYNPO | GCCGCAAATCCATGTTTACT | 50 | CTCATCCGCTGTCTGTACCA |
| 51 | TEAD1 | CAAGGTTTGAGAATGGCCG | 52 | TCCCTGTTTGTTACCACCAAT |
| 53 | TRPS1 | TTTCCCGACACTACAGGAGAG | 54 | CCGTTGGCTGTAGTGATGTC |
| 55 | VEGFA | GTCCAACATCACCATGCAGATTA | 56 | GCTGTAGGAAGCTCATCTCTC |
| 57 | WT1 | GGGTACGAGAGCGATAACCA | 58 | TCTCACCAGTGTGCTTCCTG |

Obtaining Mouse Embryonic Kidneys.

All procedures were in accordance with the NIH Guide for the Care and Use of Laboratory Animals and were approved by Institutional Animal Care and Use Committees at Brigham and Women's Hospital. Embryonic kidneys at stage E14.5 (day of plug=E0.5) were isolated from timed pregnant females (Charles River).

Electron Microscopy.

For transmission electron microscopy (TEM), kidney organoids or mouse embryonic kidneys were fixed in place using 2.5% glutaraldehyde, 1.25% paraformaldehyde, and 0.03% picric acid in 0.1 M sodium cacodylate buffer (pH 7.4) for a minimum of several hours. Small samples (1 mm×1 mm) were excised and washed in 0.1 M cacodylate buffer and bathed in 1% osmiumtetroxide ($OsO_4$) (EMS) and 1.5% potassium ferrocyanide ($KFeCN_6$) (Sigma) for 1 h, washed in water 3× and incubated in 1% aqueous uranyl acetate (EMS) for 1 h followed by 2 washes in water and subsequent dehydration in varying grades of alcohol (10 min each; 50%, 70%, 90%, 2×10 min 100%). The organoids or mouse kidneys were then put in propyleneoxide (EMS) for 1 h and incubated overnight in a 1:1 mixture of propylene-oxide and TAAB Epon™ (Marivac Canada Inc. St. Laurent, Canada). The following day the samples were embedded in embedding low viscosity epoxy resin, TAAB Epon™ and polymerized at 60° C. for 48 h. Ultrathin sections (about 60 nm) were cut on a Reichert Ultracut-S microtome, placed on copper grids, stained with lead citrate, and examined in a JEOL™ 1200EX Transmission electron microscope and images were recorded with an AMT 2k CCD camera.

For scanning electron microscopy (SEM), kidney organoids or mouse kidneys were again fixed in place using 2.5% glutaraldehyde, 1.25% paraformaldehyde, and 0.03% picric acid in 0.1 M sodium cacodylate buffer (pH 7.4) for a minimum of several hours. They were then washed 3× with PBS until picric acid (yellow color) was washed out. Organoids/mouse kidneys were placed in a 30% sucrose in PBS solution for 1 h. Then that solution was removed and replaced with a 1:1 mixture of 30% sucrose solution in PBS: optimal cutting temperature (OCT) freezing medium (Electron Microscopy Science) for 30-45 min at room temperature. Organoids were then set in a cryomold for freezing, excess fluid was removed and OCT was placed on top to fill in the mold. The organoids were frozen and placed in the −20° C. freezer overnight. The samples were then cut in a cryotome in 5 m sections (ThermoFisher), mounted on glass slides, and stained using hematoxylin and eosin. Once the opening to Bowman's capsules was visible, sectioning was ceased. The organoids were then unembedded from OCT by heating the samples to 40° C., physically removing them from OCT, washing extensively with water and then dehydrating the tissue. Subsequent dehydration in varying grades of ethanol was required (20 min each; 30%, 50%, 70%, 90%, 3×20 min 100%). The samples were then placed in 50% ethanol and 50% hexamethyldisilazane (HMDS) for 30 min followed by 100% HMDS 3×30 min. All steps were performed in a closed glass container. After the final washing with HMDS, the samples were removed and placed in an open container in the fume hood to dry. Dried samples were mounted to aluminum pin mounts using conductive carbon tape, sputter coated with 5 nm of gold or platinum, and imaged with a UltraPlus Field Emission SEM (Zeiss) at 1 keV.

Immunostaining.

Immunostaining followed by confocal microscopy was used to assess the localization of cellular or extracellular proteins within or adjacent to organoids. Prior to immunostaining, each organoid sample was washed with PBS and then fixed for 1 h using 10% buffered formalin. The fixative was removed using several washes in PBS for several hours and then blocked overnight using 1 wt % donkey serum in PBS with 0.125 wt % t-Octylphenoxypolyethoxyethanol (Triton X™-100). Primary antibodies to the protein or biomarker of interest were incubated with the constructs for 2 days at 4° C. at the dilutions listed in the table below in a solution of 0.5 wt % BSA and 0.125 wt % Triton X™-100. Removal of unbound primary antibodies was accomplished using a wash step against a solution of PBS or 0.5 wt % BSA and 0.125 wt % Triton X™-100 in PBS for 1 day. Secondary antibodies were incubated with the constructs for several hours at 1:500 dilution in a solution of 0.5 wt % BSA and 0.125 wt % Triton X™-100 in PBS. Samples were counterstained with DAP1 and then washed for at least several hours in PBS prior to imaging.

| Antibodies | | | | |
|---|---|---|---|---|
| Antibody or stain: | Source | Catalog # | Host Species & Reactivity | Concentration |
| MCAM | Abcam | ab75769 | Rabbit anti-human | 1:250 |
| PODXL | R&D Systems | AF1658 | Goat anti-human | 1:250 |
| PECAM1 | Abcam | ab9498 | Mouse anti-human | 1:250 |
| EMCN | Sigma-Aldrich | SAB4502163 | Rabbit anti-human | 1:250 |
| PDGFR-β | Abcam | ab32570 | Rabbit anti-human | 1:250 |
| LTL | Vector Labs | B-1325 | N/A | 1:250 |
| Col IV | Abcam | ab52235 | Rabbit anti-human | 1:250 |
| ATP1A1 | Abcam | ab76020 | Rabbit anti-human | 1:250 |
| TUBA4A | Abcam | ab24610 | Mouse anti-human | 1:250 |
| F-Actin (488) | Abcam | ab176753 | Human | 1:1000 |
| F-Actin (647) | ThermoFisher | A22287 | Human | 1:1000 |
| SIX2 | Proteintech | 11562 | Rabbit anti-human | 1:500 |
| SALL1 | R&D Systems | PP-K9814-00 | Mouse anti-human | 1:100 |
| PAX2 | Covance | PRB-276P | Rabbit anti-human | 1:500 |
| αSMA | Abcam | Ab5964 | Rat anti-human | 1:250 |
| Ulex-Rhodamine | Vector Labs | RL-1062 | N/A | 1:1000 |

Image Rendering and Analysis.

Phase contrast microscopy was performed using an inverted Leica DM 1 L scope with objectives ranging from 1.25× to 40×. Confocal microscopy was performed using an upright Zeiss LSM 710 with water immersion objectives ranging from 5× to 40× employing spectral lasers at 405, 488, 514, 561, and 633 nm wavelengths. Image reconstructions of z-stacks were performed in Imaris using the z-projection function with the maximum pixel intensity setting. Any increases in brightness were performed uniformly across an entire z-projected image. 3D image reconstructions and rotating movies were also performed using Imaris software. The live cell imaging system, CytoSMART™ (Lonza) in incubator system was used to capture time-lapse imaging. Confocal z-stacks were used to count the percent of ciliated cells (FIG. 15), >64 counts per condition including 4 biological replicates, and the amount of PODXL+ clusters that were invaded or wrapped by vascular cells (FIG. 18B), n>14 biological replicates per condition, over 4 independent experiments for high flow and static conditions and n between 6 and 16 biological replicates (whole organoids) per conditions over 2 independent experiments for VEGF inhibition and addition.

Angiotool Analysis

Confocal Z-stacks of PECAM1 were taken of fixed whole mount organoids, both iPSC and ESC derived, in the various culture conditions. The Z-stacks were taken at the limit of the confocal depth with each sample, roughly 250 m per sample which represents approximately the same volume per organoid analyzed. Those z-stacks were then flattened using ImageJ to a 2D max intensity projection (as required by the Angiotool for input). The default settings were employed on the Angiotool for analysis and vessel diameters of 4, 7, 10, and 14 were analyzed for each organoid. In all cases, the whole organoid was used for analysis.

Imaris Analysis

Confocal Z-stacks of PECAM1 and LTL were taken of fixed whole mount organoids, both iPSC and ESC derived, in the various culture conditions. The Z-stacks were taken at the limit of the confocal depth with each sample, roughly 250 m per sample which represents approximately the same volume per organoid analyzed. Those z-stacks were then opened in Imaris imaging software. The confocal 3D rendering was turned into a vascular surface and a tubule surface. Then the Imaris surface on surface area contact tool was used to quantify the percent overlap between the vascular and tubular surfaces in 3D, values were reported in FIG. 17(d). In order to assess the average distance the vasculature was away from a tubule, first an Imaris distance transformation was performed on the tubule surface. Then the resulting channel was masked by the vascular surface to create a new masked distance transformation channel. That masked distance transformation channel was opened in Fiji (ImageJ) to retrieve a histogram of all the 3D points, from which we obtained a geometric mean for each sample which is reported in FIG. 17(c).

Statistical Analysis.

Data in all plots were expressed as means±standard error. Statistical analysis was performed using a programming platform, MATLAB™ and GraphPad Prism 7 and statistical significance was determined at a value of $p<0.05$ as determined by an ANOVA using Tukey's multiple pairwise comparison test. Different significance levels (p values) were indicated with asterisks as such: *$p<0.05$, $p<0.01$, *$p<0.001$.

Throughout this specification, various indications have been given as to preferred and alternative embodiments of the claimed invention. However, the foregoing detailed description is to be regarded as illustrative rather than limiting and the invention is not limited to any one of the provided embodiments. It should be understood that it is the appended claims, including all equivalents, are intended to define the spirit and scope of this invention.

The invention claimed is:

1. A method of generating a vascularized renal tissue construct or renal organoid, comprising:
   providing a developing renal tissue construct or renal organoid; and
   exposing at least a portion of at least the outer surface of the developing renal tissue construct or renal organoid to fluid perfusion to impart fluidic shear stress (FSS) to induce vascularization and glomerular and tubular maturation in the developing renal tissue construct or renal organoid,
   wherein the FSS is pulsed to mimic blood pressure changes during regular heart beats or wherein the FSS is intermittent;
   thereby producing the vascularized renal tissue construct or renal organoid.

2. The method of claim 1, wherein the developing renal tissue construct or renal organoid comprises at least one of: pluripotent stem cells, multipotent stem cells, progenitor cells, nephron progenitor cells, terminally differentiated cells, endothelial cells, endothelial progenitor cells, immortalized cell lines, or primary cells.

3. The method of claim 1, wherein the developing renal tissue construct or renal organoid comprises at least one of human embryonic stem cells (hESCs) or induced pluripotent stem cells (hiPSCs).

4. The method of claim 1, wherein the exposing takes place on a perfusable chip with a substrate, on a rocker with a substrate, or by using a spinning bioreactor.

5. The method of claim 4, wherein the substrate is plasma treated or coated with a layer of at least one of a solubilized basement membrane matrix secreted by Engelbreth-Holm-Swarm (EHS) mouse sarcoma cells, poly L-lysine, reduced growth factor basement membrane matrix, gelatin, fibronectin, collagen I, collagen IV, or any other biomaterial.

6. The method of claim 4, wherein the substrate is gelatin, gelatin methacrylate, fibrin, collagen methacrylate, or a combination thereof, or any combination of gelatin, fibrin, and collagen I.

7. The method of claim 1, further comprising embedding the developing renal tissue construct or renal organoid in an extracellular matrix material (ECM), wherein the ECM is selected from the group consisting of a solubilized basement membrane matrix secreted by EHS mouse sarcoma cells, poly L-lysine, reduced growth factor basement membrane matrix, gelatin, nitrogen, fibronectin, collagen I, collagen IV, fibrinogen, gelatin metacrylate, fibrin, silk, pegylated gels, collagen methacrylate, basement membrane proteins, or any other biomaterial, or a combination thereof.

8. The method of claim 7, wherein embedding comprises at least one of: placing the developing renal tissue construct or renal organoid on top of the ECM, or partially or fully embedding the developing renal tissue construct or organoid within the ECM.

9. The method of claim 1, wherein the fluid perfusion is at FSS from about 0.001 dyn/cm$^2$ to about 50 dyn/cm$^2$.

10. The method of claim 1, wherein the perfusion is at FSS from about 0.01 dyn/cm$^2$ to about 10 dyn/cm$^2$.

11. The method of claim 1, wherein the exposing step comprises a continuous or constant imparting of the FSS for anywhere from 1 to 200 days.

12. The method of claim 1, further comprising exposing the developing renal tissue construct or renal organoid to one or more of biological agents, a biological agent gradient, a pressure gradient, an oxygen tension gradient, thereby inducing angiogenesis of capillary vessels to and/or from the developing organoid.

13. The method of claim 12, wherein the one or more biological agents, the biological agent gradient, the pressure gradient, or the oxygen tension gradient further direct development, differentiation, and/or functioning of the developing organoid.

14. The method of claim 1, further comprising embedding the developing renal tissue construct or renal organoid in a different tissue construct, wherein the embedding comprises:
   depositing one or more sacrificial filaments on the substrate to form a vascular pattern, each of the sacrificial filaments comprising a fugitive ink;
   depositing the developing renal tissue construct or renal organoid within the vascular pattern;
   at least partially surrounding the vascular pattern and/or the developing renal tissue construct or renal organoid with an extracellular matrix composition; and
   removing the fugitive ink,
   thereby forming tissue construct comprising the developing renal tissue construct or renal organoid embedded therein.

15. The method of claim 1, wherein the type of exposure to the FSS can be pre-programmed.

* * * * *

UNITED STATES PATENT AND TRADEMARK OFFICE
CERTIFICATE OF CORRECTION

PATENT NO. : 12,281,332 B2  
APPLICATION NO. : 16/620225  
DATED : April 22, 2025  
INVENTOR(S) : Kimberly A. Homan et al.

Page 1 of 1

It is certified that error appears in the above-identified patent and that said Letters Patent is hereby corrected as shown below:

In the Specification

In Column 17, Line 15, insert --.-- after "(FIG. 11)".

In Column 19, Line 32, insert --µ-- in front of "g/mL".

In Column 27, Line 60, insert --µ-- in front of "M".

In Column 28, Line 63, insert --µ-- in front of "m".

In Column 31, Line 26, insert --µ-- in front of "m".

In Column 32, Line 60, insert --µ-- in front of "m".

In Column 33, Line 6, insert --µ-- in front of "m".

In the Claims

In Column 52, Claim 7, Line 16, delete "metacrylate" and replace with --methacrylate--.

Signed and Sealed this  
Sixteenth Day of September, 2025

Coke Morgan Stewart  
*Acting Director of the United States Patent and Trademark Office*